US011136401B2

(12) United States Patent
Epstein et al.

(10) Patent No.: US 11,136,401 B2
(45) Date of Patent: Oct. 5, 2021

(54) CAR T-CELL THERAPY DIRECTED TO LHR FOR THE TREATMENT OF SOLID TUMORS

(71) Applicant: University of Southern California, Los Angeles, CA (US)

(72) Inventors: Alan L. Epstein, Pasadena, CA (US); Peisheng Hu, Covina, CA (US); Jacek K. Pinski, La Canada, CA (US)

(73) Assignee: University of Southern California, Los Angeles, CA (US)

( * ) Notice: Subject to any disclaimer, the term of this patent is extended or adjusted under 35 U.S.C. 154(b) by 812 days.

(21) Appl. No.: 15/561,967

(22) PCT Filed: Mar. 25, 2016

(86) PCT No.: PCT/US2016/024354
§ 371 (c)(1),
(2) Date: Sep. 26, 2017

(87) PCT Pub. No.: WO2016/160618
PCT Pub. Date: Oct. 6, 2016

(65) Prior Publication Data
US 2018/0112003 A1    Apr. 26, 2018

Related U.S. Application Data

(60) Provisional application No. 62/139,623, filed on Mar. 27, 2015.

(51) Int. Cl.
| C07K 16/28 | (2006.01) |
| G01N 33/574 | (2006.01) |
| C07K 16/30 | (2006.01) |
| A61P 35/00 | (2006.01) |
| A61K 35/17 | (2015.01) |
| C07K 14/725 | (2006.01) |
| C07K 14/705 | (2006.01) |
| A61K 35/12 | (2015.01) |
| A61K 39/00 | (2006.01) |
| G01N 33/76 | (2006.01) |

(52) U.S. Cl.
CPC .......... *C07K 16/2869* (2013.01); *A61K 35/17* (2013.01); *A61P 35/00* (2018.01); *C07K 14/7051* (2013.01); *C07K 14/70517* (2013.01); *C07K 14/70578* (2013.01); *C07K 16/2809* (2013.01); *C07K 16/3007* (2013.01); *C07K 16/3069* (2013.01); *G01N 33/57415* (2013.01); *G01N 33/57434* (2013.01); *G01N 33/57449* (2013.01); *G01N 33/76* (2013.01); *A61K 2035/124* (2013.01); *A61K 2039/505* (2013.01); *C07K 2317/24* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/76* (2013.01); *C07K 2319/02* (2013.01); *C07K 2319/03* (2013.01); *G01N 2800/52* (2013.01)

(58) Field of Classification Search
CPC ............ C07K 16/2869; C07K 14/7051; C07K 2317/24; C07K 2317/56; C07K 2317/622; C07K 2319/03; C07K 2319/00; C07K 2319/33; G01N 33/76; A61P 35/00; A61K 35/17; A61K 2039/5256
See application file for complete search history.

(56) References Cited

U.S. PATENT DOCUMENTS

| 7,892,753 B1 | 2/2011 | Banerjee |
| 8,580,257 B2 | 11/2013 | Tremblay et al. |
| 2002/0015973 A1 | 2/2002 | Librach et al. |
| 2005/0064518 A1 | 3/2005 | Albone et al. |
| 2005/0196397 A1 | 9/2005 | Scheiflinger et al. |
| 2006/0063209 A1 | 3/2006 | Meares et al. |
| 2008/0131912 A1 | 6/2008 | Tu et al. |
| 2008/0175835 A1 | 7/2008 | Acton et al. |
| 2011/0027270 A1 | 2/2011 | Garcia-Sastre et al. |
| 2012/0164136 A1* | 6/2012 | Pinski ................ G01N 33/5011 424/130.1 |
| 2012/0177664 A1 | 7/2012 | Yokoseki et al. |
| 2013/0280220 A1* | 10/2013 | Ahmed .................. C07K 16/32 424/93.21 |
| 2013/0287748 A1 | 10/2013 | June et al. |
| 2014/0241984 A1 | 8/2014 | El-Agnaf |

(Continued)

FOREIGN PATENT DOCUMENTS

| CN | 1737011 A | 2/2006 |
| CN | 103492406 A | 1/2014 |

(Continued)

OTHER PUBLICATIONS

Klimka A, Human anti-CD30 recombinant antibodies by guided phage antibody selection using cell panning. British Journal of Cancer (2000) 83(2), 252-260 (Year: 2000).*

(Continued)

*Primary Examiner* — Amy E Juedes
*Assistant Examiner* — Brian Hartnett
(74) *Attorney, Agent, or Firm* — Foley & Lardner LLP

(57) ABSTRACT

Provided herein are novel anti-LHR chimeric antigen receptor (CAR), cells or compositions comprising the same, vector or plasmid encoding anti-LHR CAR, and methods for producing the same, or using the same for detecting or treating ovarian cancer or prostate cancer. Also provided herein are anti-LHR antibody, compositions comprising the same, nucleic acid sequence encoding the same, and a kit for detecting LHR.

16 Claims, 15 Drawing Sheets

Specification includes a Sequence Listing.

(56) References Cited

U.S. PATENT DOCUMENTS

| | | | |
|---|---|---|---|
| 2014/0348744 | A1 | 11/2014 | Pinski |
| 2014/0370017 | A1 | 12/2014 | June et al. |
| 2015/0017141 | A1 | 1/2015 | June et al. |
| 2015/0030600 | A1 | 1/2015 | Marks et al. |
| 2015/0118202 | A1 | 4/2015 | June et al. |
| 2016/0202265 | A1 | 7/2016 | Kurosawa et al. |
| 2016/0272724 | A1 | 9/2016 | Loustau et al. |
| 2018/0112003 | A1 | 4/2018 | Epstein et al. |

FOREIGN PATENT DOCUMENTS

| | | |
|---|---|---|
| CN | 104159917 A | 11/2014 |
| CN | 104379179 A | 2/2015 |
| JP | 2014-504294 A | 2/2014 |
| WO | WO-2004/081199 A2 | 9/2004 |
| WO | WO-2007/058725 A2 | 5/2007 |
| WO | WO-2010/060186 A1 | 6/2010 |
| WO | WO-2012/079000 A1 | 6/2012 |
| WO | WO-2013/154760 A1 | 10/2013 |
| WO | WO-2014/059028 A1 | 4/2014 |
| WO | WO-2015/025825 A1 | 2/2015 |
| WO | WO-2015/133817 A1 | 9/2015 |
| WO | WO-2016/160618 A2 | 10/2016 |
| WO | WO-2016/174652 A1 | 11/2016 |
| WO | WO-2018/154386 A1 | 8/2018 |

OTHER PUBLICATIONS

U.S. Appl. No. 16/335,570, filed Sep. 22, 2017, University of Southern California.

Agaugué, et al., "Role of HLA-G in tumor escape through expansion of myeloid-derived suppressor cells and cytokinic balance in favor of Th2 versus Th1/Th17", Blood, Jun. 30, 2011, vol. 117, No. 26.

Alvaro Gonzalez et al: "The immunosuppressive molecule HLA-G and its clinical implications", Critical Reviews in Clinical Laboratory Sciences, vol. 49, No. 3, Jun. 26, 2012 (Jun. 26, 2013), pp. 63-84, XP055499681, US ISSN: 1040-8363, DOI: 10.3109/10408363. 2012.677947 *abstract; table 2*.

Anonymous, "Immunotherapy—MVR-CAR", Sep. 10, 2013 (Sep. 10, 2013), XP055528952, Retrieved from the Internet: URL:https://www.google.de/url?sa=t&rct=j&q=&esrc=s&source=web&cd=I4&ved=2ahUKEwiZI46N5PveAhUJJ1AKHYIpAHMQFjANegQIAhAC&url=http%3A%2F%2Fedu.ncc.re.kr%2Fdownload%3Ffn%3D2013%2F9%F1588828777125444.pdf, p. 49-p. 52.

Arias, et al. "RA8, A Human Anti-CD25 Antibody Against Human Treg Cells", Hybridoma, 2007, vol. 26, No. 3, pp. 119-130.

Catherine Menier et al: "Characterization of monoclonal antibodies recognizing HLA-G or HLA-E: new tools to analyze the expression of nonclassical HLA class I molecules", Human Immunology, vol. 64, No. 3, Mar. 1, 2003, (Mar. 1, 2003), pp. 315-326, XP055365555, US ISSN: 0198-8859, DOI: 10.1016/S0198-8856(02)00821-2 *p. 317, col. 1, para 2—p. 318, col. 1, para 1; fig 1-3, 5, 8-9*.

Chungyong Han et al, "Desensitized chimeric antigen receptor T cells selectively recognize target cells with enhanced antigen expression", Nature Communications, vol. 9, No. 1, Feb. 1, 2018 (Feb. 1, 2018), XP055528807,DOI: 10.1038/541467-018-02912-x.

Chungyong Han et al, "Impact of the affinity of chimeric antigen receptor on immune activation profiles of T cells Cancer Research", Jul. 1, 2018 (Jul. 1, 2018), XP055528821, Retrieved from the Internet: URL:http://cancerres.aacrjournals.org/content/78/13_Supplement/3563.

Chungyong Han et al, "Selective killing of malignant B cells using T cells redirected against malignancy variant receptor", Journal for Immunotherapy of Cancer, Biomed Central LTD, London, UK, vol. 2, No. Suppl 3, Nov. 6, 2014 (2Nov. 6, 2014), p. P16, XP 021202422, ISSN: 2051-1426, DOI: 10.1186/2051-1426-2-S3-P16.

Colman, et al. "Effects of amino acid sequence changes on antibody-antigen interactions Research in Immunology", 145:33-36, 1994.

Contini, P. et al. (2003) "Soluable HLA-A, -B, -C and -G molecules induce apoptosis in T and NK CD8 cells and inhibit cytotoxic T cell activity through CD8 ligation," Eur. J. Immunol. 33:125-134.

Dotti, et al., "Design and Development of Therapies using Chimeric Antigen Receptor-Expressing T cells", Immunol. Rev., Jan. 2014; 257(1).

Inaguma, et al., "Construction and molecular characterization of a T-cell receptor-like antibody and CAR-T cells specific for minor histocompatibility antigen HA-1H", Gene Therapy (2014) 21, 575-584.

International Search Report and Written Opinion dated Feb. 13, 2018, from application No. PCT/US2017/052974.

Kennell, et al., "Principles and Practices of Nucleic Acid Hybridization Progress in Nucleic Acid Research and Molecular Biology", vol. 11, 1971, pp. 259-301.

Khawli, et al., "Stable, Genetically Engineered F(ab')2 Fragments of Chimeric TNT-3 Expressed in Mammalian Cells", Hybridoma and Hybridomics, vol. 21, No. 1, Jul. 7, 2004.

Kumar, et al., "Critical role of OX40 signaling in the TCR-independent phase of human and murine thymic Treg generation", Cellular and Molecular Immunology, 2019, 16, pp. 138-153.

Larissa Mesquita Nunes et al: "Association between the HLA-G molecule and lymph node metastatis in papillary thyroid cancer", Human Immunology, vol. 74, No. 4, Apr. 1, 2013 (Apr. 1, 2013), pp. 447-451, XP055499684, US ISSN: 0198-8859, DOI: 10.1016/j.humimm.2012.12.012 *abstract; p. 448, col. 1, para 2.2; Fig 1-2*.

MacCallum, et al., "Antibody-antigen Interactions: Contact Analysis and Binding Site Topography", J. Mol. Biol., (1996) 262, pp. 732-745.

McKay Brown et al, "Tolerance to single, but not multiple, amino acid replacements in antibody V-H CDR2: A means of minimizing B cell wastage from somatic hypermutation?", The Journal of Immunology, The American Association of Immunologists, US, vol. 156, No. 9, Jan. 1, 1996 (Jan. 1, 1996), pp. 3285-3291, XP002649029, ISSN: 0022-1767.

Nathalie Rouas-Freiss et al: "The Dual Role of HLA-G in Cancer", Journal of Immunology Research, vol. 56, No. 3, Jan. 1, 2014 (Jan. 1, 2014), pp. 135-10, XP055227090, ISSN: 2314-8861, DOI: 10.1155/2014/359748, p. 2, col. 1, last para; p. 3, col. 1, para 1: *abstract*.

Niedojadlo, et al., "The perichromatin region of the plant cell nucleus is the area with the strongest co-localisation of snRNA and SR proteins", Planta, 2012, 236, pp. 715-726.

Panka, et al., "Variable region framework differences result in decreased or increased affinity of variant anti-digoxin antibodies", Proceedings of the National Academy of Sciences USA, vol. 85, May 1988, pp. 3080-3084.

Paul, William E., M.D., Fundamental Immunology, Third Edition, 1993, pp. 292-295.

Product Datasheet, HLA G Antibody (www.novusbio.com), retrieved on Sep. 28, 2016 from www.novusbio.com/PDFs/NBP1-43123-0.1mg.pdf, updated Mar. 1, 2016 v.20.1.

Rudikoff, et al., "Single amino acid substitution altering antigen-binding specificity", Proceedings of the National Academy of Sciences USA, vol. 79, Mar. 1982, pp. 1979-1983.

Single-chain variable fragment—Wikipedia Single-chain variable fragment pp. 1-3, downloaded Oct. 2, 2019.

UniProt, P17693 (2014), retrieved Sep. 28, 2016 from www.uniprot.org/uniprot/P17693.

Vajdos, et al., "Comprehensive Functional Maps of the Antigen-binding Site of an Anti-ErbB2 Antibody Obtained with Shotgun Scanning Mutagenesis", J. Mol. Biol., (2002) 320, pp. 415-428.

Winkler K et al, "Changing the antigen binding specificity by single point mutations of an anti-p24 (HIV-1) antibody", The Journal of Immunology, The American Association of Immunologists, US, vol. 165, No. 8, Oct. 15, 2000 (Oct. 15, 2000), pp. 4505-4514, XP002579393, ISSN: 0022-1767.

Bukovsky et al., "Multiple luteinizing hormone receptor (LHR) protein variants, interspecies reactivity of anti-LHR mAb clone 3B5, subcellular localization of LHR in human placenta, pelvic floor and brain, and possible role for LHR in the development of abnormal pregnancy, pelvic floor disorders and Alzheimer's disease", Reproductive Biology and Endocrinology, vol. 1, No. 46, Jun. 3, 2003, 18 pages.

(56) References Cited

OTHER PUBLICATIONS

Extended European Search Report dated Jul. 16, 2020, from application No. 17853995.3.
Funaro et al., "Functional Structural, and Distribution Analysis of the Chorionic Gonadotropin Receptor Using Murine Monoclonal Antibodies", The Journal of Clinical Endocrinology and Metabolism, vol. 88, No. 11, Nov. 2003, pp. 5537-5548.
Journal of Japan Obstetrics and Gynecology, vol. 54, No. 2, 2002, pp. 296, 1 page (Machine Translation).
Journal of Japan Obstetrics and Gynecology, vol. 54, No. 2, 2002, pp. 296, 1 page (No English Translation).
Liu et al., "Effects of Smad3 on the Proliferation and Steroidogenesis in Human Ovarian Luteinized Granulosa Cells", International Union of Biochemistry and Molecular Biology, vol. 66, No. 6, Jun. 30, 2014, pp. 424-437.
International Preliminary Report on Patentability dated Oct. 12, 2017, from application No. PCT/US2016/024354.
A. A. Chekmasova et al: "Successful Eradication of Established Peritoneal Ovarian Tumors in SCIO-Beige Mice following Adoptive Transfer of T Cells Genetically Targeted to the MUC16 Antigen", Clinical Cancer Research, vol. 16, No. 14, Jul. 13, 2010 (Jul. 13, 2010), pp. 3594-3606, XP055344554, US, ISSN: 1078-0432, DOI: 10.1158/1078-0432.CCR-10-0192.
Database Medline [Online] US National Library of Medicine (NLM), Bethesda, MD, US; Jun. 3, 2003 (Jun. 3, 2003), Bukovsky Antonin et al: "Multiple luteinizing hormone receptor (LHR) protein variants, interspecies reactivity of anti-LHR mAb clone 3B5, subcellular localization of LHR in human placenta, pelvic floor and brain, and possible role for LHR in the development of abnormal pregnancy, pelvic floor disorders and Alzheimer's disea", XP002783241, Database accession No. NLM12816543, *abstract* & Bukovsky Antonin et al: "Multiple luteinizing hormone receptor (LHR) protein variants, interspecies reactivity of anti-LHR mAb clone 3B5, subcellular localization of LHR in human placenta, pelvic floor and brain, and possible role for LHR in the development of abnormal pregnancy, pelvic floor disorders and Alzheimer's disea", Reproductive Biology and Endocrinology: RB&E Jun. 3, 2003, vol. I, Jun. 3, 2003 (Jun. 3, 2003), p. 46, ISSN: 1477-7827.
Database Medline [Online] US National Library of Medicine (NLM), Bethesda, MD, US; Nov. 2003 (Nov. 2003), Funaro Ada et al: "Functional, structural, and distribution analysis of the chorionic gonadotropin receptor using murine monoclonal antibodies.", XP002783240, Database accession No. NLM14602802, *abstract* & Funaro Ada et al: "Functional, structural, and distribution analysis of the chorionic gonadotropin receptor using murine monoclonal antibodies", The Journal of Clinical Endocrinology and Metabolism Nov. 2003, vol. 88, No. 11, Nov. 2003 (Nov. 2003), pp. 5537-5546, ISSN: 0021-972X.
Extended European Search Report dated Aug. 8, 2018, from application No. 16773871.5.
International Search Report and Written Opinion (ISA/US) in International Application No. PCT/US2016/024354, dated Oct. 4, 2016.

* cited by examiner

Heavy Chain Alignment

```
5F4-21       1  ...
4A7-4        1  ...
8B7-3        1  ...
13B-2        1  ...
consensus    1  VqLq SGpylVkP q8l luCt sGysits ygmhWvrQ pg gLeWmgyIw sgstt 5F4-21      60  ...
4A7-4       59  ...                                      ----SLFA
8B7-3       60  ...                                ERGLYQLPA
13B-2       60  ...                                         NLSHPI
consensus   61     Yn slk risisrhnsk vflqlnsltvtsdtstyYcargs      lry-wgqgtl 5F4-21     109    111  113
4A7-4      111    114  115
8B7-3      117    118  121
13B-2      104  --- 103---
consensus  121  vtv     ss
```

Light Chain Alignment

```
5F4-21       1  ...
13B-2        1  ...
4A7-4        1  ...
8B7-3        1  ...
consensus    1  DIVmTQtP sls spGdkvtitChsSqsinn     ylhWYQQKpgnsPKLLIy asnl 5F4-21      54  SDAF...                                     106
13B-2       55  S4 ...                                      107
4A7-4       61  6Q ...                                      113
8B7-3       55  S4 ...                                      107
consensus   61    lsGvPsrFsGSGSGTdftLtIsSv sED s YfCqq qSyPyTFGsGTKLEIK
```

FIG. 7

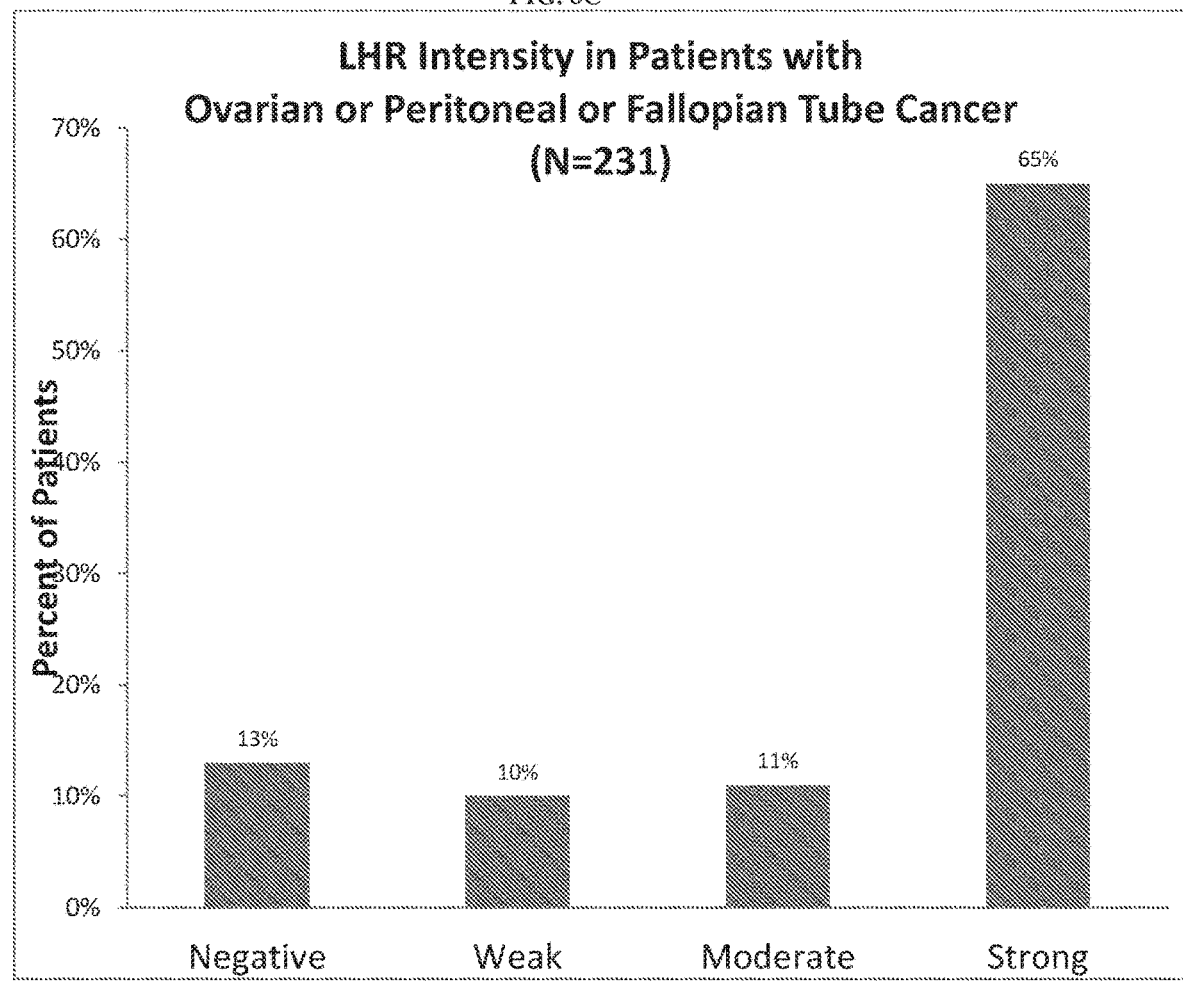

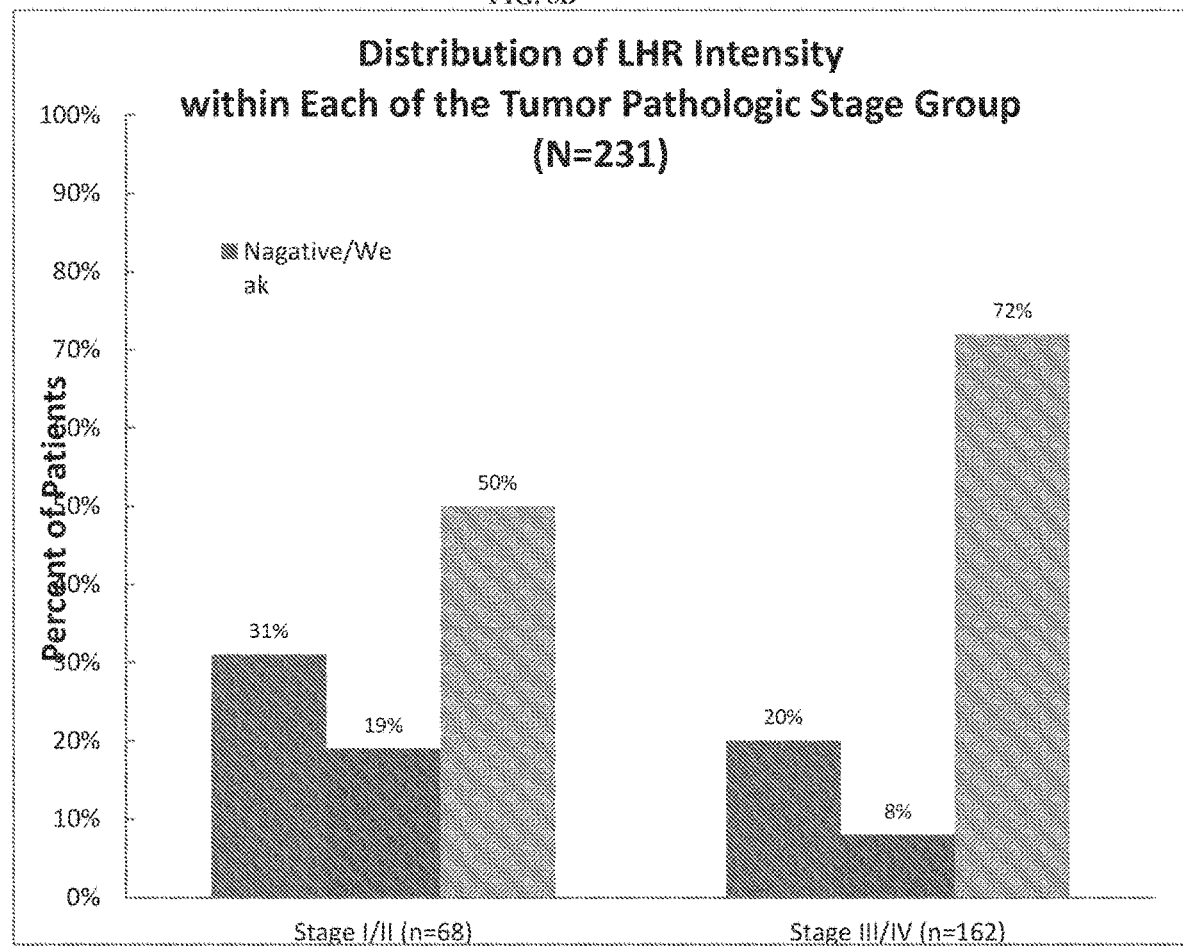

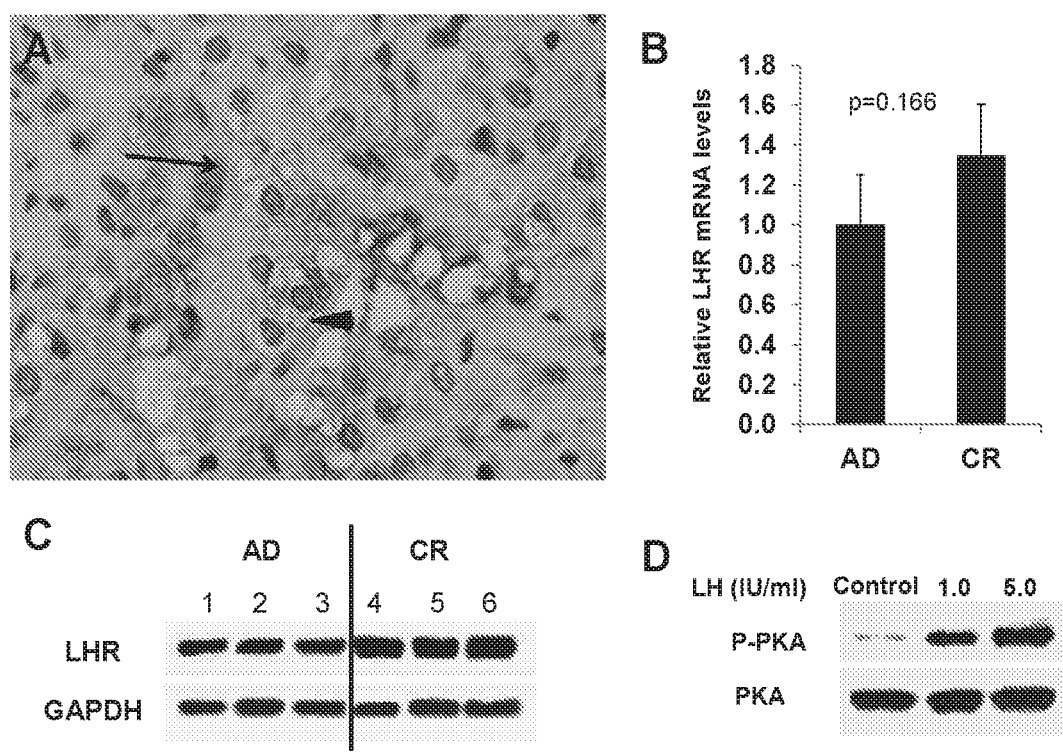
FIG. 9A-D

SEQUENCE LISTING

```
<160> NUMBER OF SEQ ID NOS: 77

<210> SEQ ID NO 1
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Gly Trp His Trp Ile Arg Gln Phe Pro Gly Asn Lys Leu Glu Trp
        35                  40                  45

Met Gly Tyr Ile His Tyr Ser Gly Ser Thr Thr Tyr Asn Pro Ser Leu
    50                  55                  60

Lys Ser Arg Ile Ser Ile Ser Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Ser Leu Arg Tyr Trp Gly Gln Gly Thr Thr Leu Thr Val Ser
            100                 105                 110

Ser
```

```
<210> SEQ ID NO 2
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Tyr Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Glu Gly Ser Ser Leu Phe Ala Tyr Trp Gly Gln Gly Thr Leu Val Thr
            100                 105                 110

Val Ser Ala
        115

<210> SEQ ID NO 3
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Glu Gln Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Leu His Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Lys Leu Pro Ser Leu Cys Tyr Gly Leu Leu Gly Ser Arg
                85                  90                  95

Asn Leu Ser His Arg Leu Leu
            100

<210> SEQ ID NO 4
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Lys Leu Gln Gln Ser Gly Pro Glu Leu Val Lys Pro Gly Ala
```

```
1               5                   10                  15
Ser Val Lys Ile Ser Cys Lys Ala Ser Gly Tyr Ser Phe Thr Gly Tyr
            20                  25                  30

Tyr Met His Trp Val Lys Gln Ser His Gly Asn Ile Leu Asp Trp Ile
            35                  40                  45

Gly Tyr Ile Tyr Pro Tyr Asn Gly Val Ser Ser Tyr Asn Gln Lys Phe
            50                  55                  60

Lys Gly Lys Ala Thr Leu Thr Val Asp Lys Ser Ser Ser Thr Ala Tyr
65                      70                  75                  80

Met Glu Leu Arg Ser Leu Thr Ser Glu Asp Ser Ala Val Tyr Tyr Cys
            85                  90                  95

Ala Arg Glu Arg Gly Leu Tyr Gln Leu Arg Ala Met Asp Tyr Trp Gly
            100                 105                 110

Gln Gly Thr Ser Val Thr Val Ser Ser
            115                 120
```

<210> SEQ ID NO 5
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Asp Ile Val Met Thr Gln Thr Pro Ala Ile Met Ser Ala Ser Pro Gly
1               5                   10                  15

Gln Lys Val Thr Ile Thr Cys Ser Ala Ser Ser Ser Val Asn Tyr Met
            20                  25                  30

His Trp Tyr Gln Gln Lys Leu Gly Ser Ser Pro Lys Leu Trp Ile Tyr
            35                  40                  45

Asp Thr Ser Lys Leu Ala Pro Gly Val Pro Ala Arg Phe Ser Gly Ser
            50                  55                  60

Gly Ser Gly Thr Ser Tyr Ser Leu Thr Ile Ser Ser Met Glu Ala Glu
65                      70                  75                  80

Asp Ala Ala Ser Tyr Phe Cys His Gln Trp Ser Ser Tyr Pro Tyr Thr
            85                  90                  95

Phe Gly Ser Gly Thr Lys Leu Glu Ile Lys
            100                 105
```

<210> SEQ ID NO 6
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (89)..(89)
<223> OTHER INFORMATION: Any amino acid

<400> SEQUENCE: 6

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
            35                  40                  45
```

```
Pro Pro Lys Leu Leu Ile Tyr Trp Ala Ser Thr Arg Gln Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Xaa Ala Val Tyr Tyr Cys Gln Asn
                85                  90                  95

Asp Tyr Ser Tyr Pro Leu Thr Phe Gly Ser Gly Thr Lys Leu Glu Ile
                100                 105                 110

Lys

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Val Leu Thr Gln Thr Pro Ser Ser Leu Ser Ala Ser Leu Gly
1               5                   10                  15

Asp Thr Ile Thr Ile Thr Cys His Ala Ser Gln Asn Ile Asn Val Trp
                20                  25                  30

Leu Phe Trp Tyr Gln Gln Lys Pro Gly Asn Ile Pro Lys Leu Leu Ile
            35                  40                  45

Tyr Lys Ala Ser Asn Leu Leu Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Phe Pro Trp
                85                  90                  95

Thr Phe Gly Gly Gly Thr Lys Leu Glu Ile Lys
                100                 105

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Val Leu Thr Gln Thr Pro Ala Thr Leu Ser Val Thr Pro Gly
1               5                   10                  15

Asp Ser Val Ser Leu Ser Cys Arg Ala Ser Gln Ser Ile Ser Asn Asn
                20                  25                  30

Leu His Trp Tyr Gln Gln Lys Ser His Glu Ser Pro Arg Leu Leu Ile
            35                  40                  45

Lys Asn Ala Ser Gln Ser Ile Ser Gly Ile Pro Ser Lys Phe Ser Gly
    50                  55                  60

Ser Gly Ser Gly Thr Asp Phe Thr Leu Arg Ile Asn Ser Val Glu Thr
65                  70                  75                  80

Glu Asp Phe Gly Met Tyr Phe Cys Gln Gln Ser Asn Ser Trp Pro Tyr
                85                  90                  95

Thr Phe Gly Ser Gly Thr Lys Leu Glu Ile Lys
                100                 105
```

```
<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Ser Ile Ser Arg Asp Asn Ser Lys
1               5

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Phe Leu Gln Leu Asn Ser Leu Thr Thr Glu Asp Thr Ala Thr Tyr
1               5                   10                  15

Tyr Cys Ala Arg Gly Ser
            20

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Arg Tyr Trp Gly Gln Gly Thr Leu Val Thr Val
1               5                   10

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Pro Gly Asp Lys Val Thr Ile Thr Cys His Ala Ser Gln Ser Ile
1               5                   10                  15

Asn Asn

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Leu His Trp Tyr Gln Gln Lys Pro Gly Asn Ser Pro Lys Leu Leu
1               5                   10                  15

Ile Tyr

<210> SEQ ID NO 14
<211> LENGTH: 24
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Ser Gly Val Pro Ser Arg Phe Ser Gly Ser Gly Ser Gly Thr Asp
1               5                   10                  15

Phe Thr Leu Thr Ile Ser Ser Val
            20

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Ser Tyr Pro Tyr Thr Phe Gly Ser Gly Thr Lys Leu Glu Ile Lys
1               5                   10                  15

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Tyr Ser Ile Thr Ser Gly Tyr Gly
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Phe Ser Leu Thr Thr Tyr Gly
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Tyr Ser Phe Thr Gly Tyr Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 19

Ile His Tyr Ser Gly Ser Thr
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Trp Gly Asp Gly Ser Thr
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Tyr Pro Tyr Asn Gly Val Ser
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Arg Ser Leu Arg Tyr
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Glu Gly Ser Ser Leu Phe Ala Tyr
1               5

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Arg Glu Arg Gly Leu Tyr Gln Leu Arg Ala Met Asp Tyr
1               5                   10

<210> SEQ ID NO 25
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 25

Ser Ser Val Asn Tyr
1               5

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Ser Leu Leu Asn Ser Gly Asn Gln Lys Asn Tyr
1               5                   10

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Ser Ile Ser Asn Asn
1               5

<210> SEQ ID NO 28
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Thr Ser
1

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Trp Ala Ser
1

<210> SEQ ID NO 30
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asn Ala Ser
1
```

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

His Gln Trp Ser Ser Tyr Pro Tyr Thr
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Gln Asn Asp Tyr Ser Tyr Pro Leu Thr
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Gln Gln Ser Asn Ser Trp Pro Tyr Thr
1               5

<210> SEQ ID NO 34
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34
gaagtgcagc tgcaggagtc aggacctgac ctggtgaaac cttctcagtc actttcactc      60
acctgcactg tcaccggcta ctccatcacc agtggttatg ctggcactg gatccggcag     120 tttccaggaa acaaactgga gtggatgggc tacatacact acagtggtag cactacctac     180
aacccatctc tcaaaagtcg aatctctatc tctcgagaca catccaagaa tcagttcttc     240
ctgcagttga attctgtgac tactgaggac acagccacat attactgtgc aagatcctta     300
cgctactggg gccaaggcac cactctcaca gtctcctca                            339

<210> SEQ ID NO 35
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35
gatattgtga tgacacagac tccagcaatc atgtctgcat ctccagggca gaaagtcacc      60

```
ataacctgca gtgccagttc aagtgtaaat tacatgcact ggtaccagca gaagctagga    120
tcctccccca aactctggat ttatgacaca tccaaactgg ctcctggagt ccctgctcgc    180
ttcagtggca gtgggtctgg gacctcttac tctctcacaa tcagcagcat ggaggctgaa    240
gatgctgcct cttatttctg ccatcagtgg agtagttacc catatacgtt cggatcgggg    300
accaagctgg aaataaaa                                                  318
```

<210> SEQ ID NO 36
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
caggtgcagc tgaaggagtc aggacctggc ctggtggcgc cctcacagag cctgtccatc    60
acatgcactg tctcagggtt ctcattaacc acctatggtg taagctgggt tcgccagcct    120
ccaggaaagg gtctggagtg gctgggagta atatgggtg acgggagcac atattatcat    180
tcagctctca tatccagact gagcatcagc aaggataact ccaagagcca agttttctta    240
aaactgaaca gtctgcaaac tgatgacaca gccacttact actgtgcgga aggtagtagc    300
ctctttgctt actggggcca agggactctg gtcactgtct ctgcg                    345
```

<210> SEQ ID NO 37
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (266)..(266)
<223> OTHER INFORMATION: a, c, t, g, unknown or other

<400> SEQUENCE: 37

```
gacattgtga tgacacagtc tccatcctcc ctgactgtga cagcaggaga gaaggtcact    60
atgagctgca gtccagtca gagtctgtta acagtggaa atcaaaagaa ctacttgacc     120
tggtaccaac agaaaccagg gcagcctcct aaactgttga tctactgggc atccactagg    180
caatctgggg tccctgatcg cttcacaggc agtggatctg gaacagactt cactctcacc    240
atcagcagtg tgcaggctga agaccnggca gtttattact gtcagaatga ttatagttat    300
cctctcacgt tcggatcggg gaccaagctg gaaataaaa                           339
```

<210> SEQ ID NO 38
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
gaggtgcagc tggagcagtc tggggaggc ttagtgcagc ctggagggtc ccggaaactc     60
tcctgtgcag cctctggatt cactttcagt agctttggaa tgcactgggt tcgtcaggct    120
ccagagaagg ggctggagtg ggtcgcatac attagtagtg gcagtagtac cctccactat    180
gcagacacag tgaagggccg attcaccatc tccagagaca atcccaagaa caccctgttc    240
```

```
ctgcaaatga aactaccctc actatgctat ggactactgg ggtcaaggaa cctcagtcac      300
cgtctcctc                                                              309

<210> SEQ ID NO 39
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gacattgtgc tgacacagac tccatccagt ctgtctgcat cccttggaga cacaattacc      60
atcacttgcc atgccagtca gaacattaat gtttggttat ctggtacca gcagaaacca     120 ggaaatattc ctaaactttt gatctataag gcttccaatt tgctcacagg cgtcccatca     180
aggtttagtg gcagtggatc tggaacaggt ttcacattaa ccatcagcag cctgcagcct     240
gaagacattg ccacttacta ctgtcaacag ggtcaaagtt ttccgtggac gttcggtgga    300
ggcaccaagc tggaaatcaa a                                               321

<210> SEQ ID NO 40
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
caggttaagc tgcagcagtc tggacctgag ctggtgaagc ctggggcttc agtgaagata      60
tcctgcaagg cttctggtta ctcattcact ggctactaca tgcactgggt gaagcagagc     120
catggaaata tcctcgattg gattggatat atttatcctt acaatggtgt ttctagctac     180
aaccagaaat tcaagggcaa ggccacattg actgtagaca gtcctctag cacagcctac      240 atggagctcc gcagcctgac atctgaggac tctgcagtct attactgtgc aagagagagg     300
ggattatatc aactacgggc tatggactac tggggtcaag gaacctcagt caccgtctcc     360
tca                                                                    363

<210> SEQ ID NO 41
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gacattgtgc tgacacagac tccagccacc ctgtctgtga ctccaggaga tagcgtcagt      60
ctttcctgca gggccagcca agtattagc aacaacctac actggtatca acaaaaatca     120
catgagtctc caaggcttct catcaagaat gcttcccagt ccatctctgg gatcccctcc    180
aagttcagtg gcagtggatc agggacagat ttcactctca gaatcaacag tgtggagact    240
gaagattttg gaatgtattt ctgtcaacag agtaacagct ggccgtatac gttcggatcg    300
gggaccaagc tggaaataaa a                                               321

<210> SEQ ID NO 42
<211> LENGTH: 84
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 42

Arg Glu Ala Leu Cys Pro Glu Pro Cys Asn Cys Val Pro Asp Gly Ala
1               5                   10                  15

Leu Arg Cys Pro Gly Pro Thr Ala Gly Leu Thr Arg Leu Ser Leu Ala
                20                  25                  30

Tyr Leu Pro Val Lys Val Ile Pro Ser Gln Ala Phe Arg Gly Leu Asn
            35                  40                  45

Glu Val Ile Lys Ile Glu Ile Ser Gln Ile Asp Ser Leu Glu Arg Ile
    50                  55                  60

Glu Ala Asn Ala Phe Asp Asn Leu Leu Asn Leu Ser Glu Ile Leu Ile
65                  70                  75                  80

Gln Asn Thr Lys

<210> SEQ ID NO 43
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Arg Ala Leu Arg Glu Ala Leu Cys Pro Glu Pro Cys Asn Cys Val Pro
1               5                   10                  15

Asp Gly Ala Leu Arg Cys Pro Gly Pro Thr Ala Gly Leu Thr Arg Leu
                20                  25                  30

Ser Leu Ala Tyr Leu Pro Val Lys Val Ile Pro Ser Gln Ala Phe Arg
            35                  40                  45

Gly Leu Asn Glu Val Ile Lys Ile Glu Ile Ser Gln Ile Asp Ser Leu
    50                  55                  60

Glu Arg Ile Glu Ala Asn Ala Phe Asp Asn Leu Leu Asn Leu Ser Glu
65                  70                  75                  80

Ile Leu Ile Gln Asn Thr Lys Asn Leu Arg Tyr Ile Glu Pro Gly Ala
                85                  90                  95

Phe Ile Asn Leu Pro Arg Leu Lys Tyr Leu Ser Ile Cys Asn Thr Gly
            100                 105                 110

Ile Arg Lys Phe Pro Asp Val Thr Lys Val Phe Ser Ser Glu Ser Asn
        115                 120                 125

Phe Ile Leu Glu Ile Cys Asp Asn Leu His Ile Thr Thr Ile Pro Gly
    130                 135                 140

Asn Ala Phe Gln Gly Met Asn Asn Glu Ser Val Thr Leu Lys Leu Tyr
145                 150                 155                 160

Gly Asn Gly Phe Glu Glu Val Gln Ser His Ala Phe Asn Gly Thr Thr
                165                 170                 175

Leu Thr Ser Leu Glu Leu Lys Glu Asn Val His Leu Glu Lys Met His
            180                 185                 190

Asn Gly Ala Phe Arg Gly Ala Thr Gly Pro Lys Thr Leu Asp Ile Ser
        195                 200                 205

Ser Thr Lys Leu Gln Ala Leu Pro Ser Tyr Gly Leu Glu Ser Ile Gln
    210                 215                 220

Arg Leu Ile Ala Thr Ser Ser Tyr Ser Leu Lys Lys Leu Pro Ser Arg
225                 230                 235                 240
```

Glu Thr Phe Val Asn Leu Leu Glu Ala Thr Leu Thr Tyr Pro Ser
            245                 250                 255

<210> SEQ ID NO 44
<211> LENGTH: 384
<212> TYPE: PRT
<213> ORGANISM: Homo sapiens

<400> SEQUENCE: 44

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
        195                 200                 205

Lys Val Pro Thr Gly Gly Val Glu Glu Gly Leu Leu Glu Arg His Ser
    210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
        275                 280                 285

Ala Ser Trp Leu Leu Cys Glu Val Ser Gly Phe Ser Pro Pro Asn Ile
    290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
                325                 330                 335

Trp Ser Val Leu Arg Val Pro Ala Pro Pro Ser Pro Gln Pro Ala Thr
            340                 345                 350

Tyr Thr Cys Val Val Ser His Glu Asp Ser Arg Thr Leu Leu Asn Ala

```
                   355                 360                 365
Ser Arg Ser Leu Glu Val Ser Tyr Val Thr Asp His Gly Pro Met Lys
    370                 375                 380

<210> SEQ ID NO 45
<211> LENGTH: 330
<212> TYPE: PRT
<213> ORGANISM: Homo sapiens

<400> SEQUENCE: 45

Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 46
<211> LENGTH: 326
```

<212> TYPE: PRT
<213> ORGANISM: Homo sapiens

<400> SEQUENCE: 46

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 47
<211> LENGTH: 377
<212> TYPE: PRT
<213> ORGANISM: Homo sapiens

<400> SEQUENCE: 47

Ala Ser Thr Lys Gly Pro Ser Val Phe Pro Leu Ala Pro Cys Ser Arg
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 48
<211> LENGTH: 452
<212> TYPE: PRT
<213> ORGANISM: Homo sapiens

<400> SEQUENCE: 48

Gly Ser Ala Ser Ala Pro Thr Leu Phe Pro Leu Val Ser Cys Glu Asn
1               5                   10                  15
```

```
Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
            35                  40                  45

Asp Ile Ser Ser Thr Arg Gly Phe Pro Ser Val Leu Arg Gly Gly Lys
 50                  55                  60

Tyr Ala Ala Thr Ser Gln Val Leu Leu Pro Ser Lys Asp Val Met Gln
 65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
            115                 120                 125

Lys Ser Lys Leu Ile Cys Gln Ala Thr Gly Phe Ser Pro Arg Gln Ile
            130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
            195                 200                 205

Asn Ala Ser Ser Met Cys Val Pro Asp Gln Asp Thr Ala Ile Arg Val
210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
            245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
            275                 280                 285

Ser Ile Cys Glu Asp Asp Trp Asn Ser Gly Glu Arg Phe Thr Cys Thr
            290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
            355                 360                 365

Gly Gln Pro Leu Ser Pro Glu Lys Tyr Val Thr Ser Ala Pro Met Pro
            370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
            420                 425                 430
```

```
Gly Lys Pro Thr Leu Tyr Asn Val Ser Leu Val Met Ser Asp Thr Ala
            435                 440                 445

Gly Thr Cys Tyr
    450

<210> SEQ ID NO 49
<211> LENGTH: 327
<212> TYPE: PRT
<213> ORGANISM: Homo sapiens

<400> SEQUENCE: 49

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 50
```

<211> LENGTH: 353
<212> TYPE: PRT
<213> ORGANISM: Homo sapiens

<400> SEQUENCE: 50

```
Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr
```

<210> SEQ ID NO 51
<211> LENGTH: 340
<212> TYPE: PRT
<213> ORGANISM: Homo sapiens

<400> SEQUENCE: 51

```
Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Cys Cys His Pro
            100                 105                 110

Arg Leu Ser Leu His Arg Pro Ala Leu Glu Asp Leu Leu Leu Gly Ser
            115                 120                 125

Glu Ala Asn Leu Thr Cys Thr Leu Thr Gly Leu Arg Asp Ala Ser Gly
130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
            195                 200                 205

Ser Gly Asn Thr Phe Arg Pro Glu Val His Leu Leu Pro Pro Pro Ser
210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
            275                 280                 285

Ala Glu Asp Trp Lys Lys Gly Asp Thr Phe Ser Cys Met Val Gly His
290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 52
<211> LENGTH: 106
<212> TYPE: PRT
<213> ORGANISM: Homo sapiens

<400> SEQUENCE: 52

Thr Val Ala Ala Pro Ser Val Phe Ile Phe Pro Pro Ser Asp Glu Gln
1               5                   10                  15
```

```
Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 53
<211> LENGTH: 699
<212> TYPE: PRT
<213> ORGANISM: Homo sapiens

<400> SEQUENCE: 53

```
Met Lys Gln Arg Phe Ser Ala Leu Gln Leu Leu Lys Leu Leu Leu Leu
1               5                   10                  15

Leu Gln Pro Pro Leu Pro Arg Ala Leu Arg Glu Ala Leu Cys Pro Glu
            20                  25                  30

Pro Cys Asn Cys Val Pro Asp Gly Ala Leu Arg Cys Pro Gly Pro Thr
        35                  40                  45

Ala Gly Leu Thr Arg Leu Ser Leu Ala Tyr Leu Pro Val Lys Val Ile
    50                  55                  60

Pro Ser Gln Ala Phe Arg Gly Leu Asn Glu Val Ile Lys Ile Glu Ile
65                  70                  75                  80

Ser Gln Ile Asp Ser Leu Glu Arg Ile Glu Ala Asn Ala Phe Asp Asn
                85                  90                  95

Leu Leu Asn Leu Ser Glu Ile Leu Ile Gln Asn Thr Lys Asn Leu Arg
            100                 105                 110

Tyr Ile Glu Pro Gly Ala Phe Ile Asn Leu Pro Arg Leu Lys Tyr Leu
        115                 120                 125

Ser Ile Cys Asn Thr Gly Ile Arg Lys Phe Pro Asp Val Thr Lys Val
    130                 135                 140

Phe Ser Ser Glu Ser Asn Phe Ile Leu Glu Ile Cys Asp Asn Leu His
145                 150                 155                 160

Ile Thr Thr Ile Pro Gly Asn Ala Phe Gln Gly Met Asn Asn Glu Ser
                165                 170                 175

Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220

Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
                245                 250                 255

Lys Lys Leu Pro Ser Arg Glu Thr Phe Val Asn Leu Leu Glu Ala Thr
            260                 265                 270

Leu Thr Tyr Pro Ser His Cys Cys Ala Phe Arg Asn Leu Pro Thr Lys
```

```
                    275                 280                 285
Glu Gln Asn Phe Ser His Ser Ile Ser Glu Asn Phe Ser Lys Gln Cys
290                 295                 300
Glu Ser Thr Val Arg Lys Val Asn Asn Lys Thr Leu Tyr Ser Ser Met
305                 310                 315                 320
Leu Ala Glu Ser Glu Leu Ser Gly Trp Asp Tyr Glu Tyr Gly Phe Cys
                325                 330                 335
Leu Pro Lys Thr Pro Arg Cys Ala Pro Glu Pro Asp Ala Phe Asn Pro
                340                 345                 350
Cys Glu Asp Ile Met Gly Tyr Asp Phe Leu Arg Val Leu Ile Trp Leu
            355                 360                 365
Ile Asn Ile Leu Ala Ile Met Gly Asn Met Thr Val Leu Phe Val Leu
        370                 375                 380
Leu Thr Ser Arg Tyr Lys Leu Thr Val Pro Arg Phe Leu Met Cys Asn
385                 390                 395                 400
Leu Ser Phe Ala Asp Phe Cys Met Gly Leu Tyr Leu Leu Leu Ile Ala
                405                 410                 415
Ser Val Asp Ser Gln Thr Lys Gly Gln Tyr Tyr Asn His Ala Ile Asp
                420                 425                 430
Trp Gln Thr Gly Ser Gly Cys Ser Thr Ala Gly Phe Phe Thr Val Phe
            435                 440                 445
Ala Ser Glu Leu Ser Val Tyr Thr Leu Thr Val Ile Thr Leu Glu Arg
450                 455                 460
Trp His Thr Ile Thr Tyr Ala Ile His Leu Asp Gln Lys Leu Arg Leu
465                 470                 475                 480
Arg His Ala Ile Leu Ile Met Leu Gly Gly Trp Leu Phe Ser Ser Leu
                485                 490                 495
Ile Ala Met Leu Pro Leu Val Gly Val Ser Asn Tyr Met Lys Val Ser
                500                 505                 510
Ile Cys Phe Pro Met Asp Val Glu Thr Thr Leu Ser Gln Val Tyr Ile
            515                 520                 525
Leu Thr Ile Leu Ile Leu Asn Val Val Ala Phe Phe Ile Ile Cys Ala
        530                 535                 540
Cys Tyr Ile Lys Ile Tyr Phe Ala Val Arg Asn Pro Glu Leu Met Ala
545                 550                 555                 560
Thr Asn Lys Asp Thr Lys Ile Ala Lys Lys Met Ala Ile Leu Ile Phe
                565                 570                 575
Thr Asp Phe Thr Cys Met Ala Pro Ile Ser Phe Phe Ala Ile Ser Ala
                580                 585                 590
Ala Phe Lys Val Pro Leu Ile Thr Val Thr Asn Ser Lys Val Leu Leu
            595                 600                 605
Val Leu Phe Tyr Pro Ile Asn Ser Cys Ala Asn Pro Phe Leu Tyr Ala
        610                 615                 620
Ile Phe Thr Lys Thr Phe Gln Arg Asp Phe Phe Leu Leu Leu Ser Lys
625                 630                 635                 640
Phe Gly Cys Cys Lys Arg Arg Ala Glu Leu Tyr Arg Arg Lys Asp Phe
                645                 650                 655
Ser Ala Tyr Thr Ser Asn Cys Lys Asn Gly Phe Thr Gly Ser Asn Lys
                660                 665                 670
Pro Ser Gln Ser Thr Leu Lys Leu Ser Thr Leu His Cys Gln Gly Thr
            675                 680                 685
Ala Leu Leu Asp Lys Thr Arg Tyr Thr Glu Cys
690                 695
```

<210> SEQ ID NO 54
<211> LENGTH: 700
<212> TYPE: PRT
<213> ORGANISM: Mus musculus

<400> SEQUENCE: 54

```
Met Gly Arg Arg Val Pro Ala Leu Arg Gln Leu Val Leu Ala Met
1               5                   10                  15

Leu Val Leu Lys Gln Ser Gln Leu His Ser Pro Glu Leu Ser Gly Ser
            20                  25                  30

Arg Cys Pro Glu Pro Cys Asp Cys Ala Pro Asp Gly Ala Leu Arg Cys
        35                  40                  45

Pro Gly Pro Arg Ala Gly Leu Ala Arg Leu Ser Leu Thr Tyr Leu Pro
    50                  55                  60

Val Lys Val Ile Pro Ser Gln Ala Phe Arg Gly Leu Asn Glu Val Val
65                  70                  75                  80

Lys Ile Glu Ile Ser Gln Ser Asp Ser Leu Glu Arg Ile Glu Ala Asn
                85                  90                  95

Ala Phe Asp Asn Leu Leu Asn Leu Ser Glu Ile Leu Ile Gln Asn Thr
            100                 105                 110

Lys Asn Leu Leu Tyr Ile Glu Pro Gly Ala Phe Thr Asn Leu Pro Arg
        115                 120                 125

Leu Lys Tyr Leu Ser Ile Cys Asn Thr Gly Ile Arg Thr Leu Pro Asp
    130                 135                 140

Val Ser Lys Ile Ser Ser Ser Glu Phe Asn Phe Ile Leu Glu Ile Cys
145                 150                 155                 160

Asp Asn Leu Tyr Ile Thr Thr Ile Pro Gly Asn Ala Phe Gln Gly Met
                165                 170                 175

Asn Asn Glu Ser Ile Thr Leu Lys Leu Tyr Gly Asn Gly Phe Glu Glu
            180                 185                 190

Val Gln Ser His Ala Phe Asn Gly Thr Thr Leu Ile Ser Leu Glu Leu
        195                 200                 205

Lys Glu Asn Ile Tyr Leu Glu Lys Met His Ser Gly Thr Phe Gln Gly
    210                 215                 220

Ala Thr Gly Pro Ser Ile Leu Asp Val Ser Ser Thr Lys Leu Gln Ala
225                 230                 235                 240

Leu Pro Ser His Gly Leu Glu Ser Ile Gln Thr Leu Ile Ala Thr Ser
                245                 250                 255

Ser Tyr Ser Leu Lys Thr Leu Pro Ser Arg Glu Lys Phe Thr Ser Leu
            260                 265                 270

Leu Val Ala Thr Leu Thr Tyr Pro Ser His Cys Cys Ala Phe Arg Asn
        275                 280                 285

Leu Pro Lys Lys Glu Gln Asn Phe Ser Phe Ser Ile Phe Glu Asn Phe
    290                 295                 300

Ser Lys Gln Cys Glu Ser Thr Val Arg Glu Ala Asn Asn Glu Thr Leu
305                 310                 315                 320

Tyr Ser Ala Ile Phe Glu Glu Asn Glu Leu Ser Gly Trp Asp Tyr Asp
                325                 330                 335

Tyr Asp Phe Cys Ser Pro Lys Thr Leu Gln Cys Thr Pro Glu Pro Asp
            340                 345                 350

Ala Phe Asn Pro Cys Glu Asp Ile Met Gly Tyr Ala Phe Leu Arg Val
        355                 360                 365

Leu Ile Trp Leu Ile Asn Ile Leu Ala Ile Phe Gly Asn Leu Thr Val
```

```
                    370                 375                 380
Leu Phe Val Leu Leu Thr Ser Arg Tyr Lys Leu Thr Val Pro Arg Phe
385                 390                 395                 400

Leu Met Cys Asn Leu Ser Phe Ala Asp Phe Cys Met Gly Leu Tyr Leu
                405                 410                 415

Leu Leu Ile Ala Ser Val Asp Ser Gln Thr Lys Gly Gln Tyr Tyr Asn
            420                 425                 430

His Ala Ile Asp Trp Gln Thr Gly Ser Gly Cys Ser Ala Ala Gly Phe
        435                 440                 445

Phe Thr Val Phe Ala Ser Glu Leu Ser Val Tyr Thr Leu Thr Val Ile
    450                 455                 460

Thr Leu Glu Arg Trp His Thr Ile Thr Tyr Ala Val Gln Leu Asp Gln
465                 470                 475                 480

Lys Leu Arg Leu Arg His Ala Ile Pro Ile Met Leu Gly Gly Trp Ile
                485                 490                 495

Phe Ser Thr Leu Met Ala Thr Leu Pro Leu Val Gly Val Ser Ser Tyr
                500                 505                 510

Met Lys Val Ser Ile Cys Leu Pro Met Asp Val Glu Ser Thr Leu Ser
                515                 520                 525

Gln Val Tyr Ile Leu Ser Ile Leu Leu Leu Asn Ala Val Ala Phe Val
                530                 535                 540

Val Ile Cys Ala Cys Tyr Val Arg Ile Tyr Phe Ala Val Gln Asn Pro
545                 550                 555                 560

Glu Leu Thr Ala Pro Asn Lys Asp Thr Lys Ile Ala Lys Lys Met Ala
                565                 570                 575

Ile Leu Ile Phe Thr Asp Phe Thr Cys Met Ala Pro Ile Ser Phe Phe
                580                 585                 590

Ala Ile Ser Ala Ala Phe Lys Val Pro Leu Ile Thr Val Thr Asn Ser
                595                 600                 605

Lys Val Leu Leu Val Leu Phe Tyr Pro Val Asn Ser Cys Ala Asn Pro
                610                 615                 620

Phe Leu Tyr Ala Val Phe Thr Lys Ala Phe Gln Arg Asp Phe Phe Leu
625                 630                 635                 640

Leu Leu Ser Arg Phe Gly Cys Cys Lys His Arg Ala Glu Leu Tyr Arg
                645                 650                 655

Arg Lys Glu Phe Ser Ala Cys Thr Phe Asn Ser Lys Asn Gly Phe Pro
                660                 665                 670

Arg Ser Ser Lys Pro Ser Gln Ala Ala Leu Lys Leu Ser Ile Val His
                675                 680                 685

Cys Gln Gln Pro Thr Pro Pro Arg Val Leu Ile Gln
                690                 695                 700

<210> SEQ ID NO 55
<211> LENGTH: 700
<212> TYPE: PRT
<213> ORGANISM: Rattus norvegicus

<400> SEQUENCE: 55

Met Gly Arg Arg Val Pro Ala Leu Arg Gln Leu Leu Val Leu Ala Val
1               5                   10                  15

Leu Leu Leu Lys Pro Ser Gln Leu Gln Ser Arg Glu Leu Ser Gly Ser
                20                  25                  30

Arg Cys Pro Glu Pro Cys Asp Cys Ala Pro Asp Gly Ala Leu Arg Cys
                35                  40                  45
```

```
Pro Gly Pro Arg Ala Gly Leu Ala Arg Leu Ser Leu Thr Tyr Leu Pro
 50                  55                  60

Val Lys Val Ile Pro Ser Gln Ala Phe Arg Gly Leu Asn Glu Val Val
 65                  70                  75                  80

Lys Ile Glu Ile Ser Gln Ser Asp Ser Leu Glu Arg Ile Glu Ala Asn
                     85                  90                  95

Ala Phe Asp Asn Leu Leu Asn Leu Ser Glu Leu Leu Ile Gln Asn Thr
                100                 105                 110

Lys Asn Leu Leu Tyr Ile Glu Pro Gly Ala Phe Thr Asn Leu Pro Arg
                115                 120                 125

Leu Lys Tyr Leu Ser Ile Cys Asn Thr Gly Ile Arg Thr Leu Pro Asp
    130                 135                 140

Val Thr Lys Ile Ser Ser Glu Phe Asn Phe Ile Leu Glu Ile Cys
145                 150                 155                 160

Asp Asn Leu His Ile Thr Thr Ile Pro Gly Asn Ala Phe Gln Gly Met
                165                 170                 175

Asn Asn Glu Ser Val Thr Leu Lys Leu Tyr Gly Asn Gly Phe Glu Glu
                180                 185                 190

Val Gln Ser His Ala Phe Asn Gly Thr Thr Leu Ile Ser Leu Glu Leu
        195                 200                 205

Lys Glu Asn Ile Tyr Leu Glu Lys Met His Ser Gly Ala Phe Gln Gly
    210                 215                 220

Ala Thr Gly Pro Ser Ile Leu Asp Ile Ser Ser Thr Lys Leu Gln Ala
225                 230                 235                 240

Leu Pro Ser His Gly Leu Glu Ser Ile Gln Thr Leu Ile Ala Leu Ser
                245                 250                 255

Ser Tyr Ser Leu Lys Thr Leu Pro Ser Lys Glu Lys Phe Thr Ser Leu
                260                 265                 270

Leu Val Ala Thr Leu Thr Tyr Pro Ser His Cys Cys Ala Phe Arg Asn
            275                 280                 285

Leu Pro Lys Lys Glu Gln Asn Phe Ser Phe Ser Ile Phe Glu Asn Phe
            290                 295                 300

Ser Lys Gln Cys Glu Ser Thr Val Arg Lys Ala Asp Asn Glu Thr Leu
305                 310                 315                 320

Tyr Ser Ala Ile Phe Glu Glu Asn Glu Leu Ser Gly Trp Asp Tyr Asp
                325                 330                 335

Tyr Gly Phe Cys Ser Pro Lys Thr Leu Gln Cys Ala Pro Glu Pro Asp
                340                 345                 350

Ala Phe Asn Pro Cys Glu Asp Ile Met Gly Tyr Ala Phe Leu Arg Val
                355                 360                 365

Leu Ile Trp Leu Ile Asn Ile Leu Ala Ile Phe Gly Asn Leu Thr Val
            370                 375                 380

Leu Phe Val Leu Leu Thr Ser Arg Tyr Lys Leu Thr Val Pro Arg Phe
385                 390                 395                 400

Leu Met Cys Asn Leu Ser Phe Ala Asp Phe Cys Met Gly Leu Tyr Leu
                405                 410                 415

Leu Leu Ile Ala Ser Val Asp Ser Gln Thr Lys Gly Gln Tyr Tyr Asn
                420                 425                 430

His Ala Ile Asp Trp Gln Thr Gly Ser Gly Cys Gly Ala Ala Gly Phe
            435                 440                 445

Phe Thr Val Phe Ala Ser Glu Leu Ser Val Tyr Thr Leu Thr Val Ile
450                 455                 460

Thr Leu Glu Arg Trp His Thr Ile Thr Tyr Ala Val Gln Leu Asp Gln
```

```
                465                 470                 475                 480

Lys Leu Arg Leu Arg His Ala Ile Pro Ile Met Leu Gly Gly Trp Leu
                    485                 490                 495

Phe Ser Thr Leu Ile Ala Thr Met Pro Leu Val Gly Ile Ser Asn Tyr
                500                 505                 510

Met Lys Val Ser Ile Cys Leu Pro Met Asp Val Glu Ser Thr Leu Ser
            515                 520                 525

Gln Val Tyr Ile Leu Ser Ile Leu Ile Leu Asn Val Val Ala Phe Val
        530                 535                 540

Val Ile Cys Ala Cys Tyr Ile Arg Ile Tyr Phe Ala Val Gln Asn Pro
545                 550                 555                 560

Glu Leu Thr Ala Pro Asn Lys Asp Thr Lys Ile Ala Lys Lys Met Ala
                565                 570                 575

Ile Leu Ile Phe Thr Asp Phe Thr Cys Met Ala Pro Ile Ser Phe Phe
                580                 585                 590

Ala Ile Ser Ala Ala Phe Lys Val Pro Leu Ile Thr Val Thr Asn Ser
            595                 600                 605

Lys Ile Leu Leu Val Leu Phe Tyr Pro Val Asn Ser Cys Ala Asn Pro
        610                 615                 620

Phe Leu Tyr Ala Ile Phe Thr Lys Ala Phe Gln Arg Asp Phe Leu Leu
625                 630                 635                 640

Leu Leu Ser Arg Phe Gly Cys Cys Lys Arg Arg Ala Glu Leu Tyr Arg
                645                 650                 655

Arg Lys Glu Phe Ser Ala Tyr Thr Ser Asn Cys Lys Asn Gly Phe Pro
                660                 665                 670

Gly Ala Ser Lys Pro Ser Gln Ala Thr Leu Lys Leu Ser Thr Val His
            675                 680                 685

Cys Gln Gln Pro Ile Pro Pro Arg Ala Leu Thr His
        690                 695                 700

<210> SEQ ID NO 56
<211> LENGTH: 51
<212> TYPE: PRT
<213> ORGANISM: Homo sapiens

<400> SEQUENCE: 56

Pro Ala Lys Pro Thr Thr Thr Pro Ala Pro Arg Pro Pro Thr Pro Ala
1               5                   10                  15

Pro Thr Ile Ala Ser Gln Pro Leu Ser Leu Arg Pro Glu Ala Cys Arg
            20                  25                  30

Pro Ala Ala Gly Gly Ala Val His Thr Arg Gly Leu Asp Phe Ala Cys
        35                  40                  45

Asp Ile Tyr
    50

<210> SEQ ID NO 57
<211> LENGTH: 49
<212> TYPE: PRT
<213> ORGANISM: Mus musculus

<400> SEQUENCE: 57

Lys Val Asn Ser Thr Thr Thr Lys Pro Val Leu Arg Thr Pro Ser Pro
1               5                   10                  15

Val His Pro Thr Gly Thr Ser Gln Pro Gln Arg Pro Glu Asp Cys Arg
            20                  25                  30

Pro Arg Gly Ser Val Lys Gly Thr Gly Leu Asp Phe Ala Cys Asp Ile
```

```
            35                  40                  45

Tyr

<210> SEQ ID NO 58
<211> LENGTH: 51
<212> TYPE: PRT
<213> ORGANISM: Felis catus

<400> SEQUENCE: 58

Pro Val Lys Pro Thr Thr Thr Pro Ala Pro Arg Pro Pro Thr Gln Ala
1               5                   10                  15

Pro Ile Thr Thr Ser Gln Arg Val Ser Leu Arg Pro Gly Thr Cys Gln
            20                  25                  30

Pro Ser Ala Gly Ser Thr Val Glu Ala Ser Gly Leu Asp Leu Ser Cys
        35                  40                  45

Asp Ile Tyr
    50

<210> SEQ ID NO 59
<211> LENGTH: 21
<212> TYPE: PRT
<213> ORGANISM: Homo sapiens

<400> SEQUENCE: 59

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 60
<211> LENGTH: 21
<212> TYPE: PRT
<213> ORGANISM: Mus musculus

<400> SEQUENCE: 60

Ile Trp Ala Pro Leu Ala Gly Ile Cys Val Ala Leu Leu Leu Ser Leu
1               5                   10                  15

Ile Ile Thr Leu Ile
            20

<210> SEQ ID NO 61
<211> LENGTH: 21
<212> TYPE: PRT
<213> ORGANISM: Rattus norvegicus

<400> SEQUENCE: 61

Ile Trp Ala Pro Leu Ala Gly Ile Cys Ala Val Leu Leu Leu Ser Leu
1               5                   10                  15

Val Ile Thr Leu Ile
            20

<210> SEQ ID NO 62
<211> LENGTH: 42
<212> TYPE: PRT
<213> ORGANISM: Unknown
<220> FEATURE:
<223> OTHER INFORMATION: Description of Unknown: 4-1BB costimulatory
      signaling region

<400> SEQUENCE: 62

Lys Arg Gly Arg Lys Lys Leu Leu Tyr Ile Phe Lys Gln Pro Phe Met
1               5                   10                  15
```

-continued

```
Arg Pro Val Gln Thr Thr Gln Glu Glu Asp Gly Cys Ser Cys Arg Phe
             20                  25                  30

Pro Glu Glu Glu Gly Gly Cys Glu Leu
         35                  40

<210> SEQ ID NO 63
<211> LENGTH: 112
<212> TYPE: PRT
<213> ORGANISM: Unknown
<220> FEATURE:
<223> OTHER INFORMATION: Description of Unknown: CD3 zeta signaling
      domain

<400> SEQUENCE: 63

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
             20                  25                  30

Asp Val Leu Asp Lys Arg Gly Arg Asp Pro Glu Met Gly Gly Lys
         35                  40                  45

Pro Arg Arg Lys Asn Pro Gln Glu Gly Leu Tyr Asn Glu Leu Gln Lys
     50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110

<210> SEQ ID NO 64
<211> LENGTH: 220
<212> TYPE: PRT
<213> ORGANISM: Unknown
<220> FEATURE:
<223> OTHER INFORMATION: Description of Unknown: CD28 polypeptide

<400> SEQUENCE: 64

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
             20                  25                  30

Asp Asn Ala Val Asn Leu Ser Cys Lys Tyr Ser Tyr Asn Leu Phe Ser
         35                  40                  45

Arg Glu Phe Arg Ala Ser Leu His Lys Gly Leu Asp Ser Ala Val Glu
     50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                 85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
            115                 120                 125

Asn Gly Thr Ile Ile His Val Lys Gly Lys His Leu Cys Pro Ser Pro
        130                 135                 140

Leu Phe Pro Gly Pro Ser Lys Pro Phe Trp Val Leu Val Val Val Gly
145                 150                 155                 160
```

```
Gly Val Leu Ala Cys Tyr Ser Leu Leu Val Thr Val Ala Phe Ile Ile
            165                 170                 175

Phe Trp Val Arg Ser Lys Arg Ser Arg Leu Leu His Ser Asp Tyr Met
        180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
        210                 215                 220
```

<210> SEQ ID NO 65

<400> SEQUENCE: 65

000

<210> SEQ ID NO 66
<211> LENGTH: 48
<212> TYPE: DNA
<213> ORGANISM: Unknown
<220> FEATURE:
<223> OTHER INFORMATION: Description of Unknown: IgG1 heavy chain hinge
      sequence

<400> SEQUENCE: 66
ctcgagccca aatcttgtga caaaactcac acatgcccac cgtgcccg                48

<210> SEQ ID NO 67
<211> LENGTH: 81
<212> TYPE: DNA
<213> ORGANISM: Unknown
<220> FEATURE:
<223> OTHER INFORMATION: Description of Unknown: CD28 transmembrane
      region

<400> SEQUENCE: 67
ttttgggtgc tggtggtggt tggtggagtc ctggcttgct atagcttgct agtaacagtg    60
gcctttatta ttttctgggt g                                             81

<210> SEQ ID NO 68
<211> LENGTH: 126
<212> TYPE: DNA
<213> ORGANISM: Unknown
<220> FEATURE:
<223> OTHER INFORMATION: Description of Unknown: 4-1BB co-stimulatory
      signaling region

<400> SEQUENCE: 68
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                             126

<210> SEQ ID NO 69
<211> LENGTH: 123
<212> TYPE: DNA
<213> ORGANISM: Unknown
<220> FEATURE:
<223> OTHER INFORMATION: Description of Unknown: CD28 co-stimulatory
      signaling region

<400> SEQUENCE: 69
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                              123

<210> SEQ ID NO 70
<211> LENGTH: 339
<212> TYPE: DNA
<213> ORGANISM: Unknown
<220> FEATURE:
<223> OTHER INFORMATION: Description of Unknown: CD3 zeta signaling
      region

<400> SEQUENCE: 70
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga agataagat ggcggaggcc tacagtgaga ttgggatgaa aggcgagcgc      240
cggaggggca aggggcacga tggcctttac caggtctca gtacagccac caaggacacc     300
tacgacgccc ttcacatgca ggccctgccc cctcgctaa                            339

<210> SEQ ID NO 71
<211> LENGTH: 105
<212> TYPE: DNA
<213> ORGANISM: Unknown
<220> FEATURE:
<223> OTHER INFORMATION: Description of Unknown: ICOS costimulatory
      signaling region

<400> SEQUENCE: 71
acaaaaaaga agtattcatc cagtgtgcac gaccctaacg gtgaatacat gttcatgaga      60
gcagtgaaca cagccaaaaa atccagactc acagatgtga cccta                    105

<210> SEQ ID NO 72
<211> LENGTH: 108
<212> TYPE: DNA
<213> ORGANISM: Unknown
<220> FEATURE:
<223> OTHER INFORMATION: Description of Unknown: OX40 costimulatory
      signaling region

<400> SEQUENCE: 72
agggaccaga ggctgccccc cgatgccac aagccccctg ggggaggcag tttccggacc       60
cccatccaag aggagcaggc cgacgccac tccaccctgg ccaagatc                  108

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cgcctgtgat atctacatct gggc                                            24

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74

```
atcggcagct acagccatct                                                 20

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Gly Gly Gly Ser Gly Gly Gly Ser Gly Gly Gly Gly Ser
1               5                   10                  15

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Gly Gly Gly Ser
1               5

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Leu Lys Leu Leu Leu Leu Leu Gln Leu Gln
1               5                   10
```

CAR T-CELL THERAPY DIRECTED TO LHR FOR THE TREATMENT OF SOLID TUMORS

CROSS-REFERENCE TO RELATED APPLICATIONS

This application is a national stage entry under 35 U.S.C. § 371 of International Application No. PCT/US2016/024354, filed Mar. 25, 2016, which in turn claims priority under 35 U.S.C. § 119(e) to U.S. Provisional Application No. 62/139,623, filed Mar. 27, 2015, the content of which is hereby incorporated by reference in its entirety.

TECHNICAL FIELD

This disclosure relates to novel luteinizing hormone receptor (LHR) chimeric antigen receptor (CAR), cells or compositions comprising the same, and methods for using the same for therapy including solid tumors. Also provided herein are isolated peptides and fusion proteins containing immunogenic determinants for the luteinizing hormone receptor chimeric antigen receptor.

BACKGROUND

Ovarian carcinoma represents the most common cause of cancer death from gynecologic tumors (Siegel, R. et al. (2012) CA Cancer J. Clin. 62:10-29). Approximately 25,000 new cases and 14,000 deaths are expected to occur in the United States every year (Siegel, R. et al. (2012) CA Cancer J. Clin. 62:10-29). Overall survival of ovarian carcinoma appears to have improved in the last 30 years as median survival during the 1960s was approximately 12 months compared to the current 38 months. However, the 5-year survival for stage III ovarian cancer has not changed significantly and remains at 25%. The improvement in median survival can be explained in part due to the improvement in front line chemotherapy. The standard initial chemotherapy for patients with ovarian cancer involves a platinum-paclitaxel based regimen (Marcus, C. S. et al. (2014) J. Cancer 5:25-30). Approximately 70% of patients will achieve a clinical response to this therapy. Despite this, most women will relapse and eventually succumb to their disease. Therefore, in an attempt to decrease distant metastasis, prolong time to recurrence and improve overall survival, it is essential to identify novel therapy targets and develop new agents.

Therefore, a need exists for a safe and effective treatment of ovarian and other solid tumor cancers, e.g., prostate cancer. This disclosure satisfies this need and provides related advantages as well.

SUMMARY OF THE DISCLOSURE

Due to the unprecedented results being recently obtained in B-cell lymphomas and leukemias using autologous treatment with genetically engineered chimeric antigen receptor (CAR) T-cells, a number of laboratories have begun to apply this approach to solid tumors including ovarian cancer. CAR modified T-cells combine the HLA-independent targeting specificity of a monoclonal antibody with the cytolytic activity, proliferation, and homing properties of activated T-cells, but do not respond to checkpoint suppression. Because of their ability to kill antigen expressing targets directly, CAR T-cells are highly toxic to any antigen positive cells or tissues making it a requirement to construct CARs with highly tumor specific antibodies. To date, CAR modified T-cells to ovarian carcinomas have been constructed against the α-folate receptor, mesothelin, and MUC-CD, but all of these have some off-target expression of antigen.

This disclosure provides a new target for the treatment of solid tumors that include, but are not limited to, ovarian and prostate carcinomas. The target, LHR, is highly expressed on the majority of these tumors but has restricted off-target positivity and therefore a desirable safety profile. Thus, in one aspect, the compositions are particularly useful in the treatment of tumors or cancerous cell that express or over-express LHR.

In one aspect, the present disclosure provides an isolated antibodies, the antibodies comprising a heavy chain (HC) immunoglobulin variable domain sequence and a light chain (LC) immunoglobulin variable domain sequence, wherein the antibody binds to an epitope of a luteinizing hormone receptor (LHR). In a further aspect, this disclosure provides an isolated anti-LHR antibody or fragment thereof as disclosed herein and a detectable or purification label, alone or in combination with an LHR antigen or fragment thereof. Further provided herein is an ex vivo cell comprising this antigen/antibody complex.

Aspects of the disclosure relate to a chimeric antigen receptor (CAR) comprising: (a) an antigen binding domain of an LHR antibody; (b) a hinge domain; (c) a transmembrane domain; and (d) an intracellular domain. Further aspects of the disclosure relate to a chimeric antigen receptor (CAR) comprising: (a) an antigen binding domain of a LHR antibody; (b) a hinge domain; (c) a CD28 transmembrane domain; (d) one or more costimulatory regions selected from a CD28 costimulatory signaling region, a 4-1BB costimulatory signaling region, an ICOS costimulatory signaling region, and an OX40 costimulatory region; and (e) a CD3 zeta signaling domain and alternatives thereof.

In a further aspect, the present disclosure provides a chimeric antigen receptor (CAR) comprising: (a) an antigen binding domain of an anti-luteinizing hormone receptor ("LHR") antibody, (b) a CD8 α hinge domain; (c) a CD8 α transmembrane domain; (d) a CD28 and/or a 4-1BB costimulatory signaling region; and (e) a CD3 zeta signaling domain and alternatives thereof.

In another aspect, the present disclosure provides an isolated nucleic acid sequence encoding the anti-LHR antibody, or the anti-LHR CAR.

In another aspect, the present disclosure provides a vector comprising the isolated nucleic acid sequence encoding the anti-LHR antibody, or the anti-LHR CAR.

In another aspect, the present disclosure provides a vector comprising the isolated nucleic acid sequence encoding the anti-LHR antibody, or the anti-LHR CAR.

In another aspect, the present disclosure provides a composition comprising a carrier and one or more of: the anti-LHR antibody; and/or the anti-LHR CAR; and/or the isolated nucleic acid encoding the anti-LHR antibody or the anti-LHR CAR; and/or the vector comprising the isolated nucleic acid sequence encoding the anti-LHR antibody, or the anti-LHR CAR; and/or an isolated cell comprising the anti-LHR CAR.

In one aspect, the disclosure provides a composition comprising, or alternatively consisting essentially of, or yet further consisting of a carrier and one or more of: an antibody or fragment thereof, a nucleic acid encoding the antibody or fragment thereof, an isolated cell comprising an anti-LHR CAR; and/or the isolated nucleic acid encoding the CAR; and/or the vector comprising the nucleic acid encoding the CAR; and/or the isolated cell expressing an anti-LHR CAR; and/or the anti-LHR antibody.

BRIEF DESCRIPTION OF THE DRAWINGS

(FIG. 2B) MUC16 antibody on a Stage IIIC endometrioid adenocarcinoma; and (FIG. 2C) mesothelin antibody on a Stage 1C serous papillary adenocarcinoma.

FIG. 7 shows the alignments of the heavy chain and light chain sequences of LHR antibody subclones.

FIGS. 8A-D shows a distribution of LHR positive cancers (FIG. 8A); the distribution of LHR intensity with multiple tumor histology groups (FIG. 8B); LHR staining intensity in patients with ovarian, peritoneal, or fallopian tube cancer (FIG. 8C); and LHR staining intensity by tumor pathologic stage group (FIG. 8D).

FIGS. 9A-D LHR expression in prostate cancer, in histology (FIG. 9A), relative mRNA levels in (AD) prostate cancer and castration resistant (CR) prostate cancer (FIG. 9B) and Western blot (FIG. 9C-D).

DETAILED DESCRIPTION

Figure 1A:
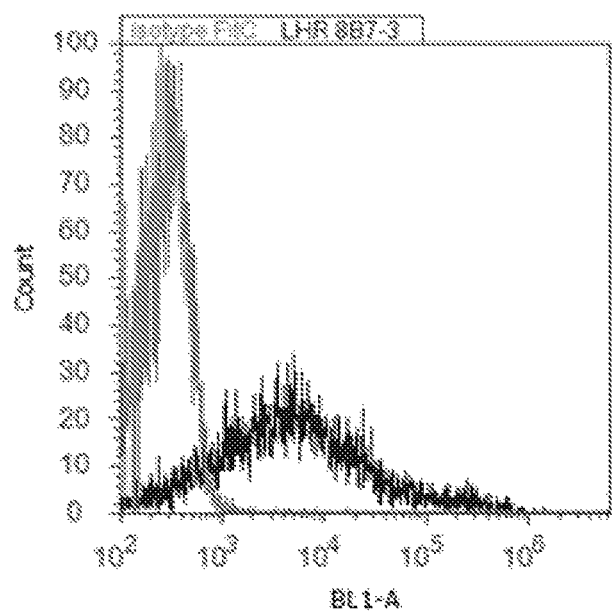
FIGS. 1A-1C show flow cytometry profiles of (FIG. 1A) LHR on TOV21G (FIG. 1B) mesothelin on SKOV3, and (FIG. 1C) MUC16 on CAOV3 cell lines.

It is to be understood that the present disclosure is not limited to particular aspects described, as such may, of course, vary. It is also to be understood that the terminology used herein is for the purpose of describing particular aspects only, and is not intended to be limiting, since the scope of the present disclosure will be limited only by the appended claims.

Unless defined otherwise, all technical and scientific terms used herein have the same meanings as commonly understood by one of ordinary skill in the art to which this technology belongs. Although any methods and materials similar or equivalent to those described herein can be used in the practice or testing of the present technology, the preferred methods, devices and materials are now described. All technical and patent publications cited herein are incorporated herein by reference in their entirety. Nothing herein is to be construed as an admission that the present technology is not entitled to antedate such disclosure by virtue of prior invention.

The practice of the present technology will employ, unless otherwise indicated, conventional techniques of tissue culture, immunology, molecular biology, microbiology, cell biology, and recombinant DNA, which are within the skill of the art. See, e.g., Sambrook and Russell eds. (2001) *Molecular Cloning: A Laboratory Manual*, 3rd edition; the series Ausubel et al. eds. (2007) *Current Protocols in Molecular Biology*; the series *Methods in Enzymology* (Academic Press, Inc., NY.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique*, 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

It is to be inferred without explicit recitation and unless otherwise intended, that when the present technology relates to a polypeptide, protein, polynucleotide or antibody, an equivalent or a biologically equivalent of such is intended within the scope of the present technology.

Definitions

As used in the specification and claims, the singular form "a", "an", and "the" include plural references unless the context clearly dictates otherwise. For example, the term "a cell" includes a plurality of cells, including mixtures thereof.

As used herein, the term "animal" refers to living multicellular vertebrate organisms, a category that includes, for example, mammals and birds. The term "mammal" includes both human and non-human mammals.

The terms "subject," "host," "individual," and "patient" are as used interchangeably herein to refer to human and veterinary subjects, for example, humans, animals, non-human primates, dogs, cats, sheep, mice, horses, and cows. In some embodiments, the subject is a human.

As used herein, the term "antibody" collectively refers to immunoglobulins or immunoglobulin-like molecules including by way of example and without limitation, IgA, IgE, IgG and IgM, combinations thereof, and similar molecules produced during an immune response in any vertebrate, for example, in mammals such as humans, goats, rabbits and mice, as well as non-mammalian species, such as shark immunoglobulins. Unless specifically noted otherwise, the term "antibody" includes intact immunoglobulins and "antibody fragments" or "antigen binding fragments" that specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4$ $M^{-1}$ greater or at least $10^5$ $M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., *Immunology*, 3$^{rd}$ Ed., W.H. Freeman & Co., New York, 1997.

In terms of antibody structure, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopts a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds LHR will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

As used herein, the term "antigen binding domain" refers to any protein or polypeptide domain that can specifically bind to an antigen target.

The term "chimeric antigen receptor" (CAR), as used herein, refers to a fused protein comprising an extracellular domain capable of binding to an antigen, a transmembrane domain derived from a polypeptide different from a polypeptide from which the extracellular domain is derived, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell. The "transmembrane domain" means any oligopeptide or polypeptide known to span the cell membrane and that can function to link the extracellular and signaling domains. A chimeric antigen receptor may optionally comprise a "hinge domain" which serves as a linker between the extracellular and transmembrane domains. Non-limiting exemplary polynucleotide sequences that encode for components of each domain are disclosed herein, e.g.:

```
Hinge domain: IgG1 heavy chain hinge sequence,
SEQ. ID NO: 66:
CTCGAGCCCAAATCTTGTGACAAAACTCACACATGCCCACCGTGCCCG
```

-continued

Transmembrane domain: CD28 transmembran region
SEQ. ID NO: 67:
TTTTGGGTGCTGGTGGTGGTTGGTGGAGTCCTGGCTTGCTATAGCTTGCT

AGTAACAGTGGCCTTTATTATTTTCTGGGTG

Intracellular domain: 4-1BB co-stimulatory
signaling region, SEQ. ID NO: 68:
AAACGGGGCAGAAAGAAACTCCTGTATATATTCAAACAACCATTTATGAG

ACCAGTACAAACTACTCAAGAGGAAGATGGCTGTAGCTGCCGATTTCCAG

AAGAAGAAGAAGGAGGATGTGAACTG

Intracellular domain: CD28 co-stimulatory
signaling region, SEQ. ID NO: 69:
AGGAGTAAGAGGAGCAGGCTCCTGCACAGTGACTACATGAACATGACTCC

CCGCCGCCCCGGGCCCACCCGCAAGGATTACCAGCCCTATGCCCCACCAC

GCGACTTCGCAGCCTATCGCTCC

Intracellular domain: CD3 zeta signaling region,
SEQ. ID NO: 70:
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGCTAA

Further embodiments of each exemplary domain component include other proteins that have analogous biological function that share at least 70%, or alternatively at least 80% amino acid sequence identity, preferably 90% sequence identity, more preferably at least 95% sequence identity with the proteins encoded by the above disclosed nucleic acid sequences. Further, non-limiting examples of such domains are provided herein.

A "composition" typically intends a combination of the active agent, e.g., compound or composition, and a naturally-occurring or non-naturally-occurring carrier, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol xylitol sorbitol (glucitol) and myoinositol.

The term "consensus sequence" as used herein refers to an amino acid or nucleic acid sequence that is determined by aligning a series of multiple sequences and that defines an idealized sequence that represents the predominant choice of amino acid or base at each corresponding position of the multiple sequences. Depending on the sequences of the series of multiple sequences, the consensus sequence for the series can differ from each of the sequences by zero, one, a few, or more substitutions. Also, depending on the sequences of the series of multiple sequences, more than one consensus sequence may be determined for the series. The generation of consensus sequences has been subjected to intensive mathematical analysis. Various software programs can be used to determine a consensus sequence.

As used herein, the term "luteinizing hormone receptor" (LHR) refers to a specific molecule associated with this name and any other molecules that have analogous biological function that share at least 70%, or alternatively at least 80% amino acid sequence identity, preferably 90% sequence identity, more preferably at least 95% sequence identity with the LHR sequence as shown herein. The protein sequences associated with GenBank Accession Nos. AAB19917.2 (*Homo sapiens*), or AAA39432.1 (*Mus musculus*), or AAA41529.1 (*Rattus norvegicus*) provide additional example sequences of LHR. Non-limiting examples of usch include:

Luteinizing hormone receptor [Homo sapiens],
SEQ. ID NO: 53:
MKQRFSALQLLKLLLLLQPPLPRALREALCPEPCNCVPDGALRCPGPTAGL

TRLSLAYLPVKVIPSQAFRGLNEVIKIEISQIDSLERIEANAFDNLLNLSE

ILIQNTKNLRYIEPGAFINLPRLKYLSICNTGIRKFPDVTKVFSSESNFIL

EICDNLHITTIPGNAFQGMNNESVTLKLYGNGFEEVQSHAFNGTTLTSLEL

KENVHLEKMHNGAFRGATGPKTLDISSTKLQALPSYGLESIQRLIATSSYS

LKKLPSRETFVNLLEATLTYPSHCCAFRNLPTKEQNFSHSISENFSKQCES

TVRKVNNKTLYSSMLAESELSGWDYEYGFCLPKTPRCAPEPDAFNPCEDIM

GYDFLRVLIWLINILAIMGNMTVLFVLLTSRYKLTVPRFLMCNLSFADFCM

GLYLLLIASVDSQTKGQYYNHAIDWQTGSGCSTAGFFTVFASELSVYTLTV

ITLERWHTITYAIHLDQKLRLRHAILIMLGGWLFSSLIAMLPLVGVSNYMK

VSICFPMDVETTLSQVYILTILILNVVAFFIICACYIKIYFAVRNPELMAT

NKDTKIAKKMAILIFTDFTCMAPISFFAISAAFKVPLITVTNSKVLLVLFY

PINSCANPFLYAIFTKTFQRDFFLLLSKFGCCKRRAELYRRKDFSAYTSNC

KNGFTGSNKPSQSTLKLSTLHCQGTALLDKTRYTEC

Luteinizing hormone receptor [Mus musculus],
SEQ. ID NO: 54:
MGRRVPALRQLLVLAMLVLKQSQLHSPELSGSRCPEPCDCAPDGALRCPGP

RAGLARLSLTYLPVKVIPSQAFRGLNEVVKIEISQSDSLERIEANAFDNLL

NLSEILIQNTKNLLYIEPGAFTNLPRLKYLSICNTGIRTLPDVSKISSSEF

NFILEICDNLYITTIPGNAFQGMNNESITLKLYGNGFEEVQSHAFNGTTLI

SLELKENIYLEKMHSGTFQGATGPSILDVSSTKLQALPSHGLESIQTLIAT

-continued

SSYSLKTLPSREKFTSLLVATLTYPSHCCAFRNLPKKEQNFSFSIFENFSK

QCESTVREANNETLYSAIFEENELSGWDYDYDFCSPKTLQCTPEPDAFNPC

EDIMGYAFLRVLIWLINILAIFGNLTVLFVLLTSRYKLTVPRFLMCNLSFA

DFCMGLYLLLIASVDSQTKGQYYNHAIDWQTGSGCSAAGFFTVFASELSVY

TLTVITLERWHTITYAVQLDQKLRLRHAIPIMLGGWIFSTLMATLPLVGVS

SYMKVSICLPMDVESTLSQVYILSILLLNAVAFVVICACYVRIYFAVQNPE

LTAPNKDTKIAKKMAILIFTDFTCMAPISFFAISAAFKVPLITVTNSKVLL

VLFYPVNSCANPFLYAVFTKAFQRDFFLLLSRFGCCKHRAELYRRKEFSAC

TFNSKNGFPRSSKPSQAALKLSIVHCQQPTPPRVLIQ

Luteinizing hormone receptor [Rattus norvegicus],
SEQ. ID NO: 55:
MGRRVPALRQLLVLAVLLLKPSQLQSRELSGSRCPEPCDCAPDGALRCPGP

RAGLARLSLTYLPVKVIPSQAFRGLNEVVKIEISQSDSLERIEANAFDNLL

NLSELLIQNTKNLLYIEPGAFTNLPRLKYLSICNTGIRTLPDVTKISSSEF

NFILEICDNLHITTIPGNAFQGMNNESVTLKLYGNGFEEVQSHAFNGTTLI

SLELKENIYLEKMHSGAFQGATGPSILDISSTKLQALPSHGLESIQTLIAL

SSYSLKTLPSKEKFTSLLVATLTYPSHCCAFRNLPKKEQNFSFSIFENFSK

QCESTVRKADNETLYSAIFEENELSGWDYDYGFCSPKTLQCAPEPDAFNPC

EDIMGYAFLRVLIWLINILAIFGNLTVLFVLLTSRYKLTVPRFLMCNLSFA

DFCMGLYLLLIASVDSQTKGQYYNHAIDWQTGSGCGAAGFFTVFASELSVY

TLTVITLERWHTITYAVQLDQKLRLRHAIPIMLGGWLFSTLIATMPLVGIS

NYMKVSICLPMDVESTLSQVYILSILILNVVAFVVICACYIRIYFAVQNPE

LTAPNKDTKIAKKMAILIFTDFTCMAPISFFAISAAFKVPLITVTNSKILL

VLFYPVNSCANPFLYAIFTKAFQRDFLLLLSRFGCCKRRAELYRRKEFSAY

TSNCKNGFPGASKPSQATLKLSTVHCQQPIPPRALTH

As used herein, the term "CD8 α hinge domain" refers to a specific protein fragment associated with this name and any other molecules that have analogous biological function that share at least 70%, or alternatively at least 80% amino acid sequence identity, preferably 90% sequence identity, more preferably at least 95% sequence identity with the CD8 α hinge domain sequence as shown herein. The example sequences of CD8 α hinge domain for human, mouse, and other species are provided in Pinto, R. D. et al. (2006) Vet. Immunol. Immunopathol. 110:169-177. Non-limiting examples of such include:

Human CD8 alpha hinge domain, SEQ. ID NO: 56:
PAKPTTTPAPRPPTPAPTIASQPLSLRPEACRPAAGGAVHTRGLDFACDIY Mouse CD8 alpha hinge domain, SEQ. ID NO: 57:
KVNSTTTKPVLRTPSPVHPTGTSQPQRPEDCRPRGSVKGTGLDFACDIY Cat CD8 alpha hinge domain, SEQ. ID NO: 58:
PVKPTTTPAPRPPTQAPITTSQRVSLRPGTCQPSAGSTVEASGLDLSCDIY As used herein, the term "CD8 α transmembrane domain" refers to a specific protein fragment associated with this name and any other molecules that have analogous biological function that share at least 70%, or alternatively at least 80% amino acid sequence identity, preferably 90% sequence identity, more preferably at least 95% sequence identity with the CD8 α transmembrane domain sequence as shown herein. The fragment sequences associated with the amino acid positions 183 to 203 of the human T-cell surface glycoprotein CD8 alpha chain (NCBI Reference Sequence: NP_001759.3), or the amino acid positions 197 to 217 of the mouse T-cell surface glycoprotein CD8 alpha chain (NCBI Reference Sequence: NP_001074579.1), and the amino acid positions 190 to 210 of the rat T-cell surface glycoprotein CD8 alpha chain (NCBI Reference Sequence: NP_113726.1) provide additional example sequences of the CD8 α transmembrane domain. The sequences associated with each of the listed NCBI are provided as follows:

Human CD8 alpha transmembrane domain,
SEQ. ID NO: 59:
IYIWAPLAGTCGVLLLSLVIT

Mouse CD8 alpha transmembrane domain,
SEQ. ID NO: 60:
IWAPLAGICVALLLSLIITLI

Rat CD8 alpha transmembrane domain,
SEQ. ID NO: 61:
IWAPLAGICAVLLLSLVITLI

As used herein, the term "CD28 transmembrane domain" refers to a specific protein fragment associated with this name and any other molecules that have analogous biological function that share at least 70%, or alternatively at least 80% amino acid sequence identity, at least 90% sequence identity, or alternatively at least 95% sequence identity with the CD28 transmembrane domain sequence as shown herein. The fragment sequences associated with the GenBank Accession Nos: XM_006712862 2 and XM_009444056.1 provide additional, non-limiting, example sequences of the CD28 transmembrane domain. The sequences associated with each of the listed accession numbers are provided as follows the sequence encoded by SEQ ID NO: 69.

As used herein, the term "4-1BB costimulatory signaling region" refers to a specific protein fragment associated with this name and any other molecules that have analogous biological function that share at least 70%, or alternatively at least 80% amino acid sequence identity, preferably 90% sequence identity, more preferably at least 95% sequence identity with the 4-1BB costimulatory signaling region sequence as shown herein. The example sequence of the 4-1BB costimulatory signaling region is provided in U.S. application Ser. No. 13/826,258. The sequence of the 4-1BB costimulatory signaling region associated disclosed in the U.S. application Ser. No. 13/826,258 is listed as follows:

The 4-1BB costimulatory signaling region,
SEQ. ID NO: 62:
KRGRKKLLYIFKQPFMRPVQTTQEEDGCSCRFPEEEEGGCEL As used herein, the term "CD28 costimulatory signaling region" refers to a specific protein fragment associated with this name and any other molecules that have analogous biological function that share at least 70%, or alternatively at least 80% amino acid sequence identity, preferably 90% sequence identity, more preferably at least 95% sequence identity with the CD28 costimulatory signaling region sequence shown herein. Exemplary CD28 costimulatory signaling domains are provided in U.S. Pat. No. 5,686,281; Geiger, T. L. et al., Blood 98: 2364-2371 (2001); Hornbach, A. et al., J Immunol 167: 6123-6131 (2001); Maher, J. et al. Nat Biotechnol 20: 70-75 (2002); Haynes, N. M. et al., J Immunol 169: 5780-5786 (2002); Haynes, N. M. et al., Blood 100: 3155-3163 (2002). Non-limiting examples include residues 114-220 of the below CD28 Sequence: MLRLLLALNL FPSIQVTGNK ILVKQSPMLV AYD-NAVNLSC KYSYNLFSRE FRASLHKGLDSAVEVCV-VYG NYSQQLQVYS KTGFNCDGKL GNESVTFYLQ NLYVNQTDIY FCKIEVMYPPPYLDNEKSNG TIIHVKGKHL CPSPLFPGPS KPFWVLVVVG GVLA-CYSLLVTVAFIIFWVR SKRSRLLHSD YMNMTPRRPG PTRKHYQPYA PPRDFAAYRS (SEQ ID NO: 64), and equivalents thereof.

As used herein, the term "ICOS costimulatory signaling region" refers to a specific protein fragment associated with this name and any other molecules that have analogous biological function that share at least 70%, or alternatively at least 80% amino acid sequence identity, preferably 90% sequence identity, more preferably at least 95% sequence identity with the ICOS costimulatory signaling region sequence as shown herein. Non-limiting example sequences of the ICOS costimulatory signaling region are provided in U.S. Publication 2015/0017141A1 the exemplary polynucleotide sequence provided below.

```
ICOS costimulatory signaling region,
SEQ ID NO: 71:
ACAAAAAAGA AGTATTCATC CAGTGTGCAC GACCCTAACG

GTGAATACAT GTTCATGAGA GCAGTGAACA CAGCCAAAAA

ATCCAGACTC ACAGATGTGA CCCTA
```

As used herein, the term "OX40 costimulatory signaling region" refers to a specific protein fragment associated with this name and any other molecules that have analogous biological function that share at least 70%, or alternatively at least 80% amino acid sequence identity, or alternativley 90% sequence identity, or alternatively at least 95% sequence identity with the OX40 costimulatory signaling region sequence as shown herein. Non-limiting example sequences of the OX40 costimulatory signaling region are disclosed in U.S. Publication 2012/20148552A1, and include the exemplary sequence provided below.

```
OX40 costimulatory signaling region,
SEQ ID NO: 72:
 AGGGACCAG AGGCTGCCCC CCGATGCCCA CAAGCCCCCT

GGGGGAGGCA GTTTCCGGAC CCCCATCCAA GAGGAGCAGG

CCGACGCCCA CTCCACCCTG GCCAAGATC
```

As used herein, the term "CD3 zeta signaling domain" refers to a specific protein fragment associated with this name and any other molecules that have analogous biological function that share at least 70%, or alternatively at least 80% amino acid sequence identity, preferably 90% sequence identity, more preferably at least 95% sequence identity with the CD3 zeta signaling domain sequence as shown herein. The example sequences of the CD3 zeta signaling domain are provided in U.S. application Ser. No. 13/826,258. The sequence associated with the CD3 zeta signaling domain is listed as follows:

```
The CD3 zeta signaling domain, SEQ. ID NO: 63:
RVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTA

TKDTYDALHMQALPPR
```

As used herein, the term "B cell," refers to a type of lymphocyte in the humoral immunity of the adaptive immune system. B cells principally function to make antibodies, serve as antigen presenting cells, release cytokines, and develop memory B cells after activation by antigen interaction. B cells are distinguished from other lymphocytes, such as T cells, by the presence of a B-cell receptor on the cell surface. B cells may either be isolated or obtained from a commercially available source. Non-limiting examples of commercially available B cell lines include lines AHH-1 (ATCC® CRL-8146™), BC-1 (TCC® CRL-2230™), BC-2 (ATCC® CRL-2231™) BC-3 (ATCC® CRL-2277™), CA46 (ATCC® CRL-1648™), DG-75 [D.G.-75] (ATCC® CRL-2625™), DS-1 (ATCC® CRL-11102™), EB-3 [EB3] (ATCC® CCL-85™), Z-138 (ATCC #CRL-3001), DB (ATCC CRL-2289), Toledo (ATCC CRL-2631), Pfiffer (ATCC CRL-2632), SR (ATCC CRL-2262), JM-1 (ATCC CRL-10421), NFS-5 C-1 (ATCC CRL-1693); NFS-70 C10 (ATCC CRL-1694), NTS-25 C-3 (ATCC CRL-1695), AND SUP-B15 (ATCC CRL-1929). Further examples include but are not limited to cell lines derived from anaplastic and large cell lymphomas, e.g., DEL, DL-40, FE-PD, JB6, Karpas 299, Ki-JK, Mac-2A Ply1, SR-786, SU-DHL-1, -2, -4,-5,-6,-7,-8,-9,-10, and -16, DOHH-2, NU-DHL-1, U-937, Granda 519, USC-DHL-1, RL; Hodgkin's lymphomas, e.g., DEV, HD-70, HDLM-2, HD-MyZ, HKB-1, KM-H2, L 428, L 540, L1236, SBH-1, SUP-HD1, SU/RH-HD-1. Non-limiting exemplary sources for such commercially available cell lines include the American Type Culture Collection, or ATCC, (www.atcc.org/) and the German Collection of Microorganisms and Cell Cultures (https://www.dsmz.de/).

As used herein, the term "T cell," refers to a type of lymphocyte that matures in the thymus. T cells play an important role in cell-mediated immunity and are distinguished from other lymphocytes, such as B cells, by the presence of a T-cell receptor on the cell surface. T-cells may either be isolated or obtained from a commercially available source. "T cell" includes all types of immune cells expressing CD3 including T-helper cells (CD4+ cells), cytotoxic T-cells (CD8+ cells), natural killer T-cells, T-regulatory cells (Treg) and gamma-delta T cells. A "cytotoxic cell" includes CD8+ T cells, natural-killer (NK) cells, and neutrophils, which cells are capable of mediating cytotoxicity responses. Non-limiting examples of commercially available T-cell lines include lines BCL2. (AAA) Jurkat (ATCC® CRL-2902™), BCL2 (S70A) Jurkat (ATCC® CRL-2900™), BCL2 (587A) Jurkat (ATCC® CRL-2901™), BCL2 Jurkat (ATCC® CRL-2899™) Neo Jurkat (ATCC® CRL-2898™), TALL-104 cytotoxic human T cell line (ATCC #CRL-11386). Further examples include but are not limited to mature T-cell lines, e.g., such as Deglis, EBT-8, HPB-MLp-W, HUT 78, HUT 102, Karpas 384, Ki 225, My-La, Se-Ax, SKW-3, SMZ-1 and T34; and immature T-cell lines, e.g., ALL-SIL, Be13, CCRF-CEM, CML-T1, DND-41, DU.528, EU-9, HD-Mar, HPB-ALL, H-SB2, HT-1, JK-T1, Jurkat, Karpas 45, KE-37, KOPT-K1, K-T1, L-KAW, Loucy, MAT, MOLT-1, MOLT 3, MOLT-4, MOLT 13, MOLT-16, MT-1, MT-ALL, P12/Ichikawa, Peer, PER0117, PER-255, PF-382, PFI-285, RPMI-8402, ST-4, SUP-T1 to T14, TALL-1, TALL-101, TALL-103/2, TALL-104, TALL-105, TALL-106, TALL-107, TALL-197, TK-6, TLBR-1, -2, -3, and -4, CCRF-HSB-2 (CCL-120.1), J.RT3-T3.5 (ATCC TIB-153), J45.01 (ATCC CRL-1990), J.CaM1.6 (ATCC CRL-2063), RS4;11 (ATCC CRL-1873), CCRF-CEM (ATCC CRM-CCL-119); and cutaneous T-cell lymphoma lines, e.g., HuT78 (ATCC CRM-TIB-161), MJ[G11] (ATCC CRL- 8294), HuT102 (ATCC TIB-162). Null leukemia cell lines, including but not limited to REH, NALL-1, KM-3, L92-221, are a another commercially available source of immune cells, as are cell lines derived from other leukemias and lymphomas, such as K562 erythroleukemia, THP-1 monocytic leukemia, U937 lymphoma, HEL erythroleukemia, HL60 leukemia, HMC-1 leukemia, KG-1 leukemia, U266 myeloma. Non-limiting exemplary sources for such commercially available cell lines include the American Type Culture Collection, or ATCC, (http://www.atcc.org/) and the German Collection of Microorganisms and Cell Cultures (https://www.dsmz.de/).

As used herein, the term "NK cell," also known as natural killer cell, refers to a type of lymphocyte that originates in the bone marrow and play a critical role in the innate immune system. NK cells provide rapid immune responses against viral-infected cells, tumor cells or other stressed cell, even in the absence of antibodies and major histocompatibility complex on the cell surfaces. NK cells may either be isolated or obtained from a commercially available source. Non-limiting examples of commercial NK cell lines include lines NK-92 (ATCC® CRL-2407™), NK-92MI (ATCC® CRL-2408™). Further examples include but are not limited to NK lines HANK1, KHYG-1, NKL, NK-YS, NOI-90, and YT. Non-limiting exemplary sources for such commercially available cell lines include the American Type Culture Collection, or ATCC, (http://www.atcc.org/) and the German Collection of Microorganisms and Cell Cultures (https://www.dsmz.de/).

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multistranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "encode" as it is applied to nucleic acid sequences refers to a polynucleotide which is said to "encode" a polypeptide if, in its native state or when manipulated by methods well known to those skilled in the art, can be transcribed and/or translated to produce the mRNA for the polypeptide and/or a fragment thereof. The antisense strand is the complement of such a nucleic acid, and the encoding sequence can be deduced therefrom.

As used herein, the term "vector" refers to a nucleic acid construct deigned for transfer between different hosts, including but not limited to a plasmid, a virus, a cosmid, a phage, a BAC, a YAC, etc. In some embodiments, plasmid vectors may be prepared from commercially available vectors. In other embodiments, viral vectors may be produced from baculoviruses, retroviruses, adenoviruses, AAVs, etc. according to techniques known in the art. In one embodiment, the viral vector is a lentiviral vector.

The term "promoter" as used herein refers to any sequence that regulates the expression of a coding sequence, such as a gene. Promoters may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors.

As used herein, the term "isolated cell" generally refers to a cell that is substantially separated from other cells of a tissue. "Immune cells" includes, e.g., white blood cells (leukocytes) which are derived from hematopoietic stem cells (HSC) produced in the bone marrow, lymphocytes (T cells, B cells, natural killer (NK) cells) and myeloid-derived cells (neutrophil, eosinophil, basophil, monocyte, macrophage, dendritic "T cell" includes all types of immune cells expressing CD3 including T-helper cells (CD4+ cells), cytotoxic T-cells (CD8+ cells), natural killer T-cells, T-regulatory cells (Treg) and gamma-delta T cells. A "cytotoxic cell" includes CD8+ T cells, natural-killer (NK) cells, and neutrophils, which cells are capable of mediating cytotoxicity responses.

The term "transduce" or "transduction" as it is applied to the production of chimeric antigen receptor cells refers to the process whereby a foreign nucleotide sequence is introduced into a cell. In some embodiments, this transduction is done via a vector.

As used herein, the term "autologous," in reference to cells refers to cells that are isolated and infused back into the same subject (recipient or host). "Allogeneic" refers to non-autologous cells.

An "effective amount" or "efficacious amount" refers to the amount of an agent, or combined amounts of two or more agents, that, when administered for the treatment of a mammal or other subject, is sufficient to effect such treatment for the disease. The "effective amount" will vary depending on the agent(s), the disease and its severity and the age, weight, etc., of the subject to be treated.

A "solid tumor" is an abnormal mass of tissue that usually does not contain cysts or liquid areas. Solid tumors can be benign or malignant. Different types of solid tumors are named for the type of cells that form them. Examples of solid tumors include sarcomas, carcinomas, and lymphomas.

The term "ovarian cancer" refers to a type of cancer that forms in issues of the ovary, and has undergone a malignant transformation that makes the cells within the cancer pathological to the host organism with the ability to invade or spread to other parts of the body. The ovarian cancer herein comprises type I cancers of low histological grade and type II cancer of higher histological grade. Particularly, the ovarian cancer includes but is not limited to epithelial carcinoma, serous carcinoma, clear-cell carcinoma, sex cord stromal tumor, germ cell tumor, dysgerminoma, mixed tumors, secondary ovarian cancer, low malignant potential tumors.

The term "prostate cancer" refers to a type of cancer that develops in the prostate, a gland in the male reproductive system. The prostate cancer herein includes but is not limited to adenocarcinoma, sarcomas, small cell carcinomas, neuroendocrine tumors, transitional cell carcinomas.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. For example, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions disclosed herein. Aspects defined by each of these transition terms are within the scope of the present disclosure.

As used herein, the term "detectable marker" refers to at least one marker capable of directly or indirectly, producing a detectable signal. A non-exhaustive list of this marker includes enzymes which produce a detectable signal, for example by colorimetry, fluorescence, luminescence, such as horseradish peroxidase, alkaline phosphatase, β-galactosidase, glucose-6-phosphate dehydrogenase, chromophores such as fluorescent, luminescent dyes, groups with electron density detected by electron microscopy or by their electrical property such as conductivity, amperometry, voltammetry, impedance, detectable groups, for example whose molecules are of sufficient size to induce detectable modifications in their physical and/or chemical properties, such detection may be accomplished by optical methods such as diffraction, surface plasmon resonance, surface variation, the contact angle change or physical methods such as atomic force spectroscopy, tunnel effect, or radioactive molecules such as $^{32}P$, $^{35}S$ or $^{125}I$.

As used herein, the term "purification marker" refers to at least one marker useful for purification or identification. A non-exhaustive list of this marker includes His, lacZ, GST, maltose-binding protein, NusA, BCCP, c-myc, CaM, FLAG, GFP, YFP, cherry, thioredoxin, poly(NANP), V5, Snap, HA, chitin-binding protein, Softag 1, Softag 3, Strep, or S-protein. Suitable direct or indirect fluorescence marker comprise FLAG, GFP, YFP, RFP, dTomato, cherry, Cy3, Cy 5, Cy 5.5, Cy 7, DNP, AMCA, Biotin, Digoxigenin, Tamra, Texas Red, rhodamine, Alexa floors, FITC, TRITC or any other fluorescent dye or hapten.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample. In one aspect, the expression level of a gene from one sample may be directly compared to the expression level of that gene from a control or reference sample. In another aspect, the expression level of a gene from one sample may be directly compared to the expression level of that gene from the same sample following administration of a compound.

As used herein, "homology" or "identical", percent "identity" or "similarity", when used in the context of two or more nucleic acids or polypeptide sequences, refers to two or more sequences or subsequences that are the same or have a specified percentage of nucleotides or amino acid residues that are the same, e.g., at least 60% identity, preferably at least 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein). Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. The terms "homology" or "identical", percent "identity" or "similarity" also refer to, or can be applied to, the complement of a test sequence. The terms also include sequences that have deletions and/or additions, as well as those that have substitutions. As described herein, the preferred algorithms can account for gaps and the like. Preferably, identity exists over a region that is at least about 25 amino acids or nucleotides in length, or more preferably over a region that is at least 50-100 amino acids or nucleotides in length. An "unrelated" or "non-homologous" sequence shares less than 40% identity, or alternatively less than 25% identity, with one of the sequences disclosed herein.

The phrase "first line" or "second line" or "third line" refers to the order of treatment received by a patient. First line therapy regimens are treatments given first, whereas second or third line therapy are given after the first line therapy or after the second line therapy, respectively. The National Cancer Institute defines first line therapy as "the first treatment for a disease or condition. In patients with cancer, primary treatment can be surgery, chemotherapy, radiation therapy, or a combination of these therapies. First line therapy is also referred to those skilled in the art as "primary therapy and primary treatment." See National Cancer institute website at www.cancer.gov, last visited on May 1, 2008. Typically, a patient is given a subsequent chemotherapy regimen because the patient did not show a positive clinical or sub-clinical response to the first line therapy or the first line therapy has stopped.

In one aspect, the term "equivalent" or "biological equivalent" of an antibody means the ability of the antibody to selectively bind its epitope protein or fragment thereof as measured by ELISA or other suitable methods. Biologically equivalent antibodies include, but are not limited to, those antibodies, peptides, antibody fragments, antibody variant, antibody derivative and antibody mimetics that bind to the same epitope as the reference antibody.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or at least 80% homology or identity and alternatively, or at least about 85%, or alternatively at least about 90%, or alternatively at least about 95%, or alternatively 98% percent homology or identity and exhibits substantially equivalent biological activity to the reference protein, polypeptide or nucleic acid. Alternatively, when referring to polynucleotides, an equivalent thereof is a polynucleotide that hybridizes under stringent conditions to the reference polynucleotide or its complement.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC. 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

A "normal cell corresponding to the tumor tissue type" refers to a normal cell from a same tissue type as the tumor tissue. A non-limiting example is a normal lung cell from a patient having lung tumor, or a normal colon cell from a patient having colon tumor.

The term "isolated" as used herein refers to molecules or biologicals or cellular materials being substantially free from other materials. In one aspect, the term "isolated" refers to nucleic acid, such as DNA or RNA, or protein or polypeptide (e.g., an antibody or derivative thereof), or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. The term "isolated" is also used herein to refer to cells or tissues that are isolated from other cells or tissues and is meant to encompass both cultured and engineered cells or tissues.

As used herein, the term "monoclonal antibody" refers to an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

The term "protein", "peptide" and "polypeptide" are used interchangeably and in their broadest sense to refer to a compound of two or more subunit amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any aspect of this technology that is a polynucleotide encompasses both the double-stranded form and each of two complementary single-stranded forms known or predicted to make up the double-stranded form.

As used herein, the term "purified" does not require absolute purity; rather, it is intended as a relative term. Thus, for example, a purified nucleic acid, peptide, protein, biological complexes or other active compound is one that is isolated in whole or in part from proteins or other contaminants. Generally, substantially purified peptides, proteins, biological complexes, or other active compounds for use within the disclosure comprise more than 80% of all macromolecular species present in a preparation prior to admixture or formulation of the peptide, protein, biological complex or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, biological complex or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

As used herein, the term "specific binding" means the contact between an antibody and an antigen with a binding affinity of at least $10^{-6}$M. In certain aspects, antibodies bind with affinities of at least about $10^{-7}$M and preferably $10^{-8}$M, $10^{-9}$M, $10^{-10}$M, $10^{-11}$M, or $10^{-12}$M.

As used herein, the term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

As used herein, the term "overexpress" with respect to a cell, a tissue, or an organ expresses a protein to an amount that is greater than the amount that is produced in a control cell, a control issue, or an organ. A protein that is overexpressed may be endogenous to the host cell or exogenous to the host cell.

As used herein the term "linker sequence" relates to any amino acid sequence comprising from 1 to 10, or alternatively, 8 amino acids, or alternatively 6 amino acids, or alternatively 5 amino acids that may be repeated from 1 to 10, or alternatively to about 8, or alternatively to about 6, or alternatively about 5, or 4 or alternatively 3, or alternatively 2 times. For example, the linker may comprise up to 15 amino acid residues consisting of a pentapeptide repeated three times. In one aspect, the linker sequence is a (Glycine4Serine)3 flexible polypeptide linker comprising three copies of gly-gly-gly-gly-ser.

As used herein, the term "enhancer", as used herein, denotes sequence elements that augment, improve or ameliorate transcription of a nucleic acid sequence irrespective of its location and orientation in relation to the nucleic acid sequence to be expressed.

An enhancer may enhance transcription from a single promoter or simultaneously from more than one promoter.

As long as this functionality of improving transcription is retained or substantially retained (e.g., at least 70%, at least 80%, at least 90% or at least 95% of wild-type activity, that is, activity of a full-length sequence), any truncated, mutated or otherwise modified variants of a wild-type enhancer sequence are also within the above definition.

As used herein, the term "WPRE" or "Woodchuck Hepatitis Virus (WHP) Post-transcriptional Regulatory Element" refers to a specific nucleotide fragment associated with this name and any other molecules that have analogous biological function that share at least 70%, or alternatively at least 80% amino acid sequence identity, preferably 90% sequence identity, more preferably at least 95% sequence identity with the WPRE sequence as shown herein. For example, WPRE refers to a region similar to the human hepatitis B virus posttranscriptional regulatory element (HBVPRE) present in the Woodchuck hepatitis virus genomic sequence (GenBank Accession No. J04514), and that the 592 nucleotides from position 1093 to 1684 of this genomic sequence correspond to the post-transcriptional regulatory region (Journal of Virology, Vol. 72, p. 5085-5092, 1998). The analysis using retroviral vectors revealed that WPRE inserted into the 3'-terminal untranslated region of a gene of interest increases the amount of protein produced by 5 to 8 folds. It has also been reported that the introduction of WPRE suppresses mRNA degradation (Journal of Virology, Vol. 73, p. 2886-2892, 1999). In a broad sense, elements such as WPRE that increase the efficiency of amino acid translation by stabilizing mRNAs are also thought to be enhancers.

LIST OF ABBREVIATIONS

CAR: chimeric antigen receptor
HLA: histocompatibility lymphocyte antigen
Ip: intraperitoneal
IRES: internal ribosomal entry site
LHR: leuteinizing hormone receptor
MFI: mean fluorescence intensity
MOI: multiplicity of infection
PBMC: peripheral blood mononuclear cells
PBS: phosphate buffered saline
scFv: single chain variable fragment
WPRE: woodchuck hepatitis virus post-transcriptional regulatory element The sequences associated with each of the above listed GenBank Accession Nos., UniProt Reference Nos., and references are herein incorporated by reference.

MODES FOR CARRYING OUT THE DISCLOSURE

CAR T-cells are genetically engineered autologous T-cells in which single chain antibody fragments (scFv) or ligands are attached to the T-cell signaling domain capable of facilitating T-cell activation (Maher, J. (2012) ISRN Oncol. 2012:278093; Curran, K. J. et al. (2012) J. Gene Med. 14:405-415; Fedorov, V. D. et al. (2014) Cancer J. 20:160-165; Barrett, D. M. et al. (2014) Annu. Rev. Med. 65:333-347). CARs combine HLA-independent targeting specificity of a monoclonal antibody with the cytolytic activity and homing properties of activated T-cells. These properties enable the recognition of target cells with reduced HLA expression or down-regulated antigen processing pathways, two common methods tumors employ to evade the host immune response (Jakobsen, M. K. et al. (1995) J. Immunother. Emphasis Tumor Immunol. 17:222-228; Lou, Y. et al. (2008) Clin. Cancer Res. 14:1494-1501; Singh, R. et al.

(2007) Cancer Res. 67:1887-1892), CAR-modified T-cells have shown great promise in preclinical and clinical settings as novel therapeutics in various diseases including ovarian carcinomas (Chu, C. S. et al (2008) Expert Rev. Anticancer Ther. 8:243-257; Chekmasova, A. A. et al. (2010) Discov. Med. 9:62-70; Porter, D. L. et al. (2011) NEJM 365:725-733). To date, CAR T-cells generated against mesothelin (Kelly, R. J. et al. (2012) Mol. Cancer Ther. 11:517-525; Beatty, G. L. et al. (2014) Cancer Immunol. Res. 2:112-120) are currently in clinical trial at the National Cancer Institute (protocol ID: 120111; NCT01583686), the University of Pennsylvania (just enrolling patients), and in China (4 patients completed). These studies are very preliminary and except for the α-folate receptor (Kandalaft, L. E. et al. (2012) J. Transl. Med. 10:157-167) and MUC16 (Chekmasova, A. A. et al. (2010) Clin. Cancer Res. 16:3594-606; Rao, T. D. et al. (2010) Appl. Immunohistochem. Mol. Morphology 18:462-472), no other targets to our knowledge are currently under development for the treatment of ovarian cancer.

Figure 1B:
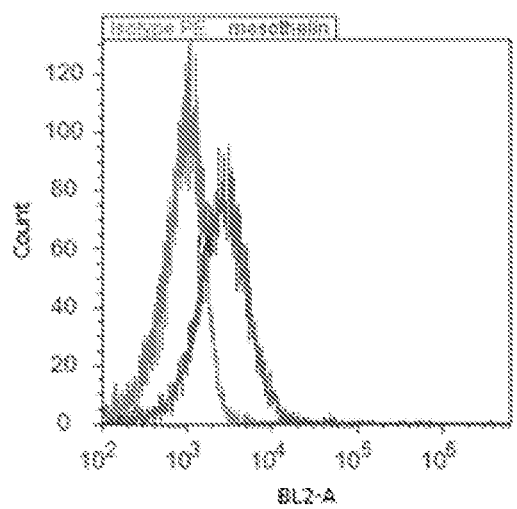
Figure 1C:
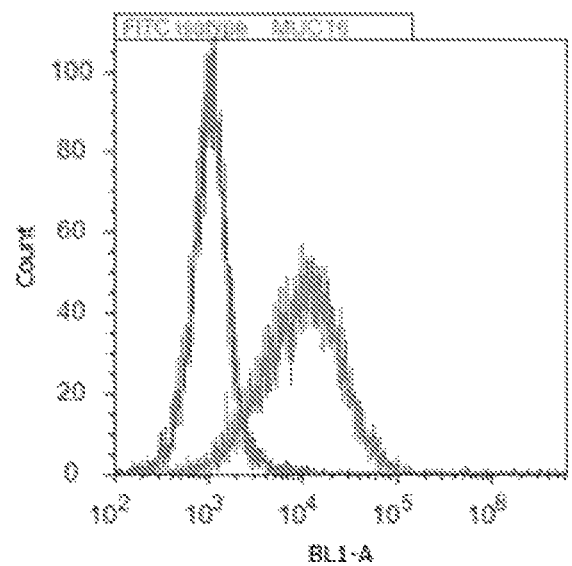
Figure 2A:
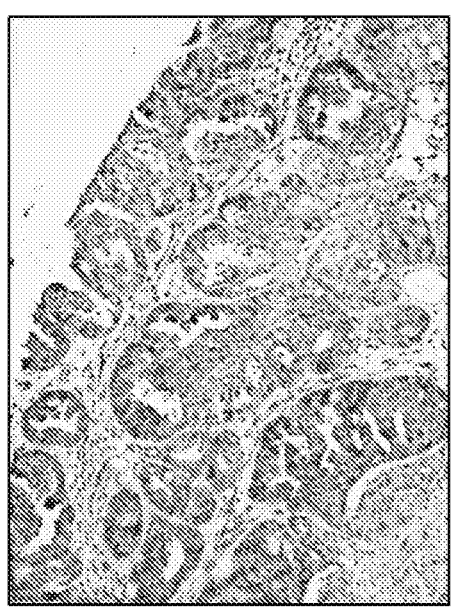
FIGS. 2A-2C show positive immunohistochemistry staining patterns of (FIG. 2A) LHR antibody on a Stage 2 serous papillary adenocarcinoma.
Figure 2B:
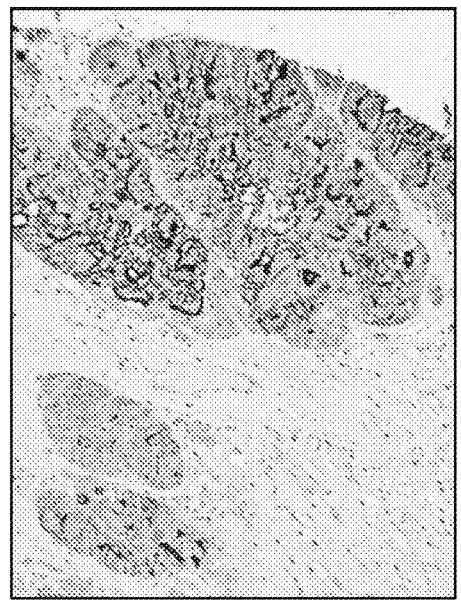
Figure 2C:
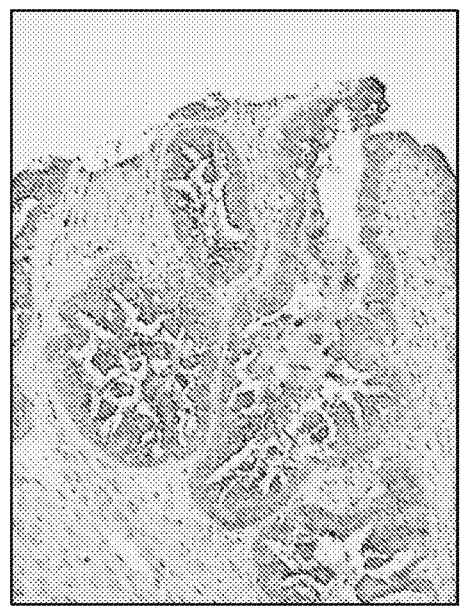

As described in more detail below, the inventors have demonstrated that LHR is a potent target for CAR T-cell therapy. As shown below in Table 1 and FIG. 1, flow cytometric studies utilizing 9 well established human ovarian cell lines showed LHR to be an excellent target compared to mesothelin and MUC16, which were only positive on half or less of the cell lines tested. These targets were also tested on a multi-block slide of human ovarian cancers by immunohistochemistry as shown in Table 2. Consistent with the flow cytometric results, LHR positivity was more consistently seen than mesothelin and MUC16 positivity by these methods regardless of the stage or grade of tumor tested. As shown in FIG. 2, the immunohistochemical staining patterns were somewhat different with each antibody. Both the MUC 16 and mesothelin antibodies tended to stain the luminal surfaces of tumor nodules and did not stain the cell surface of all cells especially those more on the periphery of tumor nodules. By contrast, the LHR antibody stained both the cytoplasm and cell surface and tended to stain all the cells of the tumor nodules. Finally, the off-target staining of each antibody was tested on multi-tissue arrays of normal tissues. The results of these studies shown in Table 3 below and show that all three targets have limited reactivity on normal tissues.

Consistent with these principles and discoveries, this disclosure provides the following embodiments.
Antibodies and Uses Thereof
 I. Compositions The general structure of antibodies is known in the art and will only be briefly summarized here. An immunoglobulin monomer comprises two heavy chains and two light chains connected by disulfide bonds. Each heavy chain is paired with one of the light chains to which it is directly bound via a disulfide bond. Each heavy chain comprises a constant region (which varies depending on the isotype of the antibody) and a variable region. The variable region comprises three hypervariable regions (or complementarity determining regions) which are designated CDRH1, CDRH2 and CDRH3 and which are supported within framework regions. Each light chain comprises a constant region and a variable region, with the variable region comprising three hypervariable regions (designated CDRL1, CDRL2 and CDRL3) supported by framework regions in an analogous manner to the variable region of the heavy chain.

The hypervariable regions of each pair of heavy and light chains mutually cooperate to provide an antigen binding site that is capable of binding a target antigen. The binding specificity of a pair of heavy and light chains is defined by the sequence of CDR1, CDR2 and CDR3 of the heavy and light chains. Thus once a set of CDR sequences (i.e. the sequence of CDR1, CDR2 and CDR3 for the heavy and light chains) is determined which gives rise to a particular binding specificity, the set of CDR sequences can, in principle, be inserted into the appropriate positions within any other antibody framework regions linked with any antibody constant regions in order to provide a different antibody with the same antigen binding specificity.

In one embodiment, the disclosure provides an isolated antibody comprising a heavy chain (HC) immunoglobulin variable domain sequence and a light chain (LC) immunoglobulin variable domain sequence, wherein the antibody binds to an epitope of a luteinizing hormone receptor (LHR).

In one aspect, the HC of the antibody comprises or alternatively consists essentially of, or yet further consists of one or more of a CDR1 comprising the amino acid sequence of GYSITSGYG (SEQ ID NO.: 16) or an equivalent of each thereof; and/or a CDR2 comprising the amino acid sequence of IHYSGST (SEQ ID NO.: 19) or an equivalent of each thereof; and/or a CDR3 comprising the amino acid sequence of ARSLRY (SEQ ID NO.: 22) or an equivalent of each thereof; and/or the LC comprises the antibody of comprises or alternatively consists essentially of, or yet further consists of a CDR1 comprising the amino acid sequence of SSVNY (SEQ ID NO.:25) or an equivalent of each thereof; and/or a CDR2 comprising the amino acid sequence of DTS (SEQ ID NO:28) or an equivalent of each thereof; and/or a CDR3 comprising the amino acid sequence of HQWSSYPYT (SEQ ID NO:31) or an equivalent of each thereof.

In one aspect, the antibody comprises a HC that comprises, or alternatively consists essentially of, or yet further consists of a one or more of: a CDR1 comprising the amino acid sequence of GFSLTTYG (SEQ ID NO.: 17) or an equivalent of each thereof; and/or a CDR2 comprising the amino acid sequence of IWGDGST (SEQ ID NO.: 20) or an equivalent of each thereof; and/or a CDR3 comprising the amino acid sequence of AEGSSLFAY (SEQ ID NO.: 23) or an equivalent of each thereof; and/or the LC of the antibody comprises, or alternatively consists essentially of, or yet further consists of a CDR1 comprising the amino acid sequence of QSLLNSGNQKNY (SEQ ID NO.:26) or an equivalent of each thereof; and/or a CDR2 comprising the amino acid sequence of WAS (SEQ ID NO:29) or an equivalent of each thereof; and/or a CDR3 comprising the amino acid sequence of QNDYSYPLT (SEQ ID NO:32) or an equivalent of each thereof.

In another aspect, the HC of the antibody comprises, or alternatively consists essentially of, or yet further consists of one or more of: a CDR1 comprising the amino acid sequence of GYSFTGYY (SEQ ID NO.: 18) or an equivalent of each thereof; and/or a CDR2 comprising the amino acid sequence of IYPYNGVS (SEQ ID NO.: 21) or an equivalent of each thereof; and/or a CDR3 comprising the amino acid sequence of ARERGLYQLRAMDY (SEQ ID NO.: 24) or an equivalent of each thereof; and/or the LC of the antibody comprises, or alternatively consists essentially of, or yet further consists of a CDR1 comprising the amino acid sequence of QSISNN (SEQ ID NO.:27) or an equivalent of each thereof; and/or a CDR2 comprising the amino acid sequence of NAS (SEQ ID NO:30) or an equivalent of each thereof; and/or a CDR3 comprising the amino acid sequence of QQSNSWPYT (SEQ ID NO:33) or an equivalent of each thereof.

In one aspect, the disclosure provides an isolated anti-LHR antibody which is generated against a LHR fragment.

In one embodiment, the LHR fragment is part of LHR G protein with the following amino acid sequence (SEQ ID NO: 42):

REALCPEPCNCVPDGALRCPGPTAGLTRLSLAYLPVKVIPSQAFRGLN
EVIKIEISQIDSLERIEANAFDNLLNLSEILIQNTK.

In another embodiment, the LHR fragment is the N-terminal of LHR protein with the following amino acid sequence (SEQ ID NO: 43):

RALREALCPEPCNCVPDGALRCPGPTAGLTRLSLAYLPVKVIPSQAFR

GLNEVIKIEISQIDSLERIEANAFDNLLNLSEILIQNTKNLRYIEPGA

FINLPRLKYLSICNTGIRKFPDVTKVFSSESNFILEICDNLHITTIPG

NAFQGMNNESVTLKLYGNGFEEVQSHAFNGTTLTSLELKENVHLEKMH

NGAFRGATGPKTLDISSTKLQALPSYGLESIQRLIATSSYSLKKLPSR

ETFVNLLEATLTYPS.

In another embodiment, the antibody is a monoclonal antibody comprising an anti-LHR heavy chain variable region comprising, or alternatively consisting essentially of, or yet further consisting of a polypeptide selected from SEQ ID NOs.:1-4 or an equivalent of each thereof, and an anti-LHR light chain variable region comprising, or alternatively consisting essentially of, or yet further consisting of a polypeptide selected from SEQ ID NOs.:5-8 or an equivalent of each thereof.

In another aspect, the antibody is a chimeric antibody or a humanized antibody.

In another aspect, the heavy chain variable region comprises, or alternatively consists essentially of, or yet further consists of a polypeptide with a consensus sequence selected from SEQ ID NOs: 9-11, and an anti-LHR light chain variable region comprises, or alternatively consists essentially of, or yet further consists of a polypeptide with a consensus sequence selected from SEQ ID NOs.:12-15.

In another aspect, the disclosure provides an isolated nucleic acid encoding the isolated anti-LHR antibody. In further embodiment, the isolated nucleic acid comprising, or alternatively consisting essentially of, or yet further consisting of a nucleic acid sequence selected from SEQ ID NOs.:16-23 of an equivalent of each therefore.

In one aspect, the HC of the antibody comprises or alternatively consists essentially of, or yet further consists of one or more of: a CDR1 comprising the amino acid sequence of GYSITSGYG (SEQ ID NO.: 16) or an equivalent of each thereof; and/or a CDR2 comprising the amino acid sequence of IHYSGST (SEQ ID NO.: 19) or an equivalent of each thereof; and/or a CDR3 comprising the amino acid sequence of ARSLRY (SEQ ID NO.: 22) or an equivalent of each thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the light chain variable regions of the antibodies comprises or alternatively consists essentially of, or yet further consists of one or more of: a CDR1 comprising the amino acid sequence of SSVNY (SEQ ID NO.:25) or an equivalent of each thereof; and/or a CDR2 comprising the amino acid sequence of DTS (SEQ ID NO:28) or an equivalent of each thereof; and/or a CDR3 comprising the amino acid sequence of HQWSSYPYT (SEQ ID NO:31) or an equivalent of each thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In one aspect, the HC of the antibody comprises, or alternatively consists essentially of, or yet further consists of one or more of a CDR1 comprising the amino acid sequence of GFSLTTYG (SEQ ID NO.: 17) or an equivalent of each thereof; and/or a CDR2 comprising the amino acid sequence of IWGDGST (SEQ ID NO.: 20) or an equivalent of each thereof; and/or a CDR3 comprising the amino acid sequence of AEGSSLFAY (SEQ ID NO.: 23) or an equivalent of each thereof; and/or the LC of the antibody comprises, or alternatively consists essentially of, or yet further consists of a CDR1 comprising the amino acid sequence of QSLLNSGNQKNY (SEQ ID NO.:26) or an equivalent of each thereof; and/or a CDR2 comprising the amino acid sequence of WAS (SEQ ID NO:29) or an equivalent of each thereof; and/or a CDR3 comprising the amino acid sequence of QNDYSYPLT (SEQ ID NO:32) or an equivalent of each thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In another aspect, the HC of the antibody comprises, or alternatively consists essentially of, or yet further consists of one or more of: a CDR1 comprising the amino acid sequence of GYSFTGYY (SEQ ID NO.: 18) or an equivalent of each thereof; and/or a CDR2 comprising the amino acid sequence of IYPYNGVS (SEQ ID NO.: 21) or an equivalent of each thereof; and/or a CDR3 comprising the amino acid sequence of ARERGLYQLRAMDY (SEQ ID NO.: 24) or an equivalent of each thereof; and/or the LC of the antibody comprises, or alternatively consists essentially of, or yet further consists of a CDR1 comprising the amino acid sequence of QSISNN (SEQ ID NO.:27) or an equivalent of each thereof; and/or a CDR2 comprising the amino acid sequence of NAS (SEQ ID NO:30) or an equivalent of each thereof; and/or a CDR3 comprising the amino acid sequence of QQSNSWPYT (SEQ ID NO:33) or an equivalent of each thereof.

In one aspect, the disclosure provides an isolated anti-LHR antibody which is generated against a LHR fragment.

In one embodiment, the LHR fragment against which the antibody is raised is part of LHR protein with the following amino acid sequence (SEQ ID NO: 42):

REALCPEPCNCVPDGALRCPGPTAGLTRLSLAYLPVKVIPSQAFRGLN
EVIKIEISQIDSLERIEANAFDNLLNLSEILIQNTK.

In another embodiment, the LHR fragment is the N-terminal of LHR protein with the following amino acid sequence (SEQ ID NO: 43):

RALREALCPEPCNCVPDGALRCPGPTAGLTRLSLAYTPVKVIPSQAFR

GLNEVIKIEISQIDSLERIEANAFDNLLNLSEILIQNTKNLRYIEPGA

FINLPRLKYLSICNTGIRKFPDVTKVFSSESNFILEICDNLHITTIPG

NAFQGMNNESVTLKLYGNGFEEVQSHAFNGTTLTSLELKENVHLEKMH

-continued

NGAFRGATGPKTLDISSTKLQALPSYGLESIQRLIATSSYSLKKLPSR

ETFVNLLEATLTYPS.

In another embodiment, the antibody is a monoclonal antibody comprising an anti-LHR heavy chain variable region comprising, or alternatively consisting essentially of, or yet further consisting of a polypeptide selected from SEQ ID NOs.:1-4 or an equivalent of each thereof.

In another embodiment, the antibody is a monoclonal antibody comprising an anti-LHR light chain variable region comprising, or alternatively consisting essentially of, or yet further consisting of a polypeptide selected from SEQ ID NOs.:5-8 or an equivalent of each thereof.

In another aspect, the anti-LHR antibody is a chimeric antibody, human or a humanized antibody.

In another aspect, the heavy chain variable region comprises, or alternatively consists essentially of, or yet further consists of a polypeptide with a consensus sequence selected from SEQ ID NOs: 9-11, and an anti-LHR light chain variable region comprises, or alternatively consists essentially of, or yet further consists of a polypeptide with a consensus sequence selected from SEQ ID NOs.:12-15, or equivalents of each thereof.

In another aspect of the present technology, the isolated antibody includes one or more of the following characteristics:

(a) the light chain immunoglobulin variable domain sequence comprises one or more CDRs that are at least 85% identical to a CDR of a light chain variable domain of any of the disclosed light chain sequences;

(b) the heavy chain immunoglobulin variable domain sequence comprises one or more CDRs that are at least 85% identical to a CDR of a heavy chain variable domain of any of the disclosed heavy chain sequences;

(c) the light chain immunoglobulin variable domain sequence is at least 85% identical to a light chain variable domain of any of the disclosed light chain sequences;

(d) the HC immunoglobulin variable domain sequence is at least 85% identical to a heavy chain variable domain of any of the disclosed light chain sequences; and (e) the antibody binds an epitope that overlaps with an epitope bound by any of the disclosed sequences.

In one aspect, the present disclosure provides an isolated antibody that is at least 85% identical to the anti-LHR antibodies, e.g., 5F4-21, 4A7-4, 8B7-3 or 138-2, as disclosed herein.

In some of the aspects of the antibodies provided herein, the antibody binds human LHR with a dissociation constant ($K_D$) of less than $10^{-4}$M, $10^{-5}$M, $10^{-6}$M, $10^{-7}$M, $10^{-8}$M, $10^{-9}$M, $10^{-10}$M, $10^{-11}$M, or $10^{-12}$M. In some of the aspects of the antibodies provided herein, the antigen binding site specifically binds to human LHR.

In some of the aspects of the antibodies provided herein, the antibody is soluble Fab.

In some of the aspects of the antibodies provided herein, the HC and LC variable domain sequences are components of the same polypeptide chain. In some of the aspects of the antibodies provided herein, the HC and LC variable domain sequences are components of different polypeptide chains.

In some of the aspects of the antibodies provided herein, the antibody is a full-length antibody. In other aspect, antigen binding fragments of the antibodies are provided.

In some of the aspects of the antibodies provided herein, the antibody is a monoclonal antibody.

In some of the aspects of the antibodies provided herein, the antibody is chimeric or humanized.

In some of the aspects of the antibodies provided herein, the antibody fragment is selected from the group consisting of Fab, F(ab)'2, Fab', scF$_v$, and F$_v$.

In other aspects, one or more amino acid residues in a CDR of the antibodies provided herein are substituted with another amino acid. The substitution may be "conservative" in the sense of being a substitution within the same family of amino acids. The naturally occurring amino acids may be divided into the following four families and conservative substitutions will take place within those families:

1) Amino acids with basic side chains: lysine, arginine, histidine;
2) Amino acids with acidic side chains: aspartic acid, glutamic acid;
3) Amino acids with uncharged polar side chains: asparagine, glutamine, serine, threonine, tyrosine;
4) Amino acids with nonpolar side chains: glycine, alanine, valine, leucine, isoleucine, proline, phenylalanine, methionine, tryptophan, cysteine.

In another aspect, one or more amino acid residues are added to or deleted from one or more CDRs of an antibody. Such additions or deletions occur at the N or C termini of the CDR or at a position within the CDR.

By varying the amino acid sequence of the CDRs of an antibody by addition, deletion or substitution of amino acids, various effects such as increased binding affinity for the target antigen may be obtained.

It is to be appreciated that antibodies of the present disclosure comprising such varied CDR sequences still bind LHR with similar specificity and sensitivity profiles as the disclosed antibodies. This may be tested by way of the binding assays.

The constant regions of antibodies may also be varied. For example, antibodies may be provided with Fc regions of any isotype: IgA (IgA1, IgA2), IgD, IgE, IgG (IgG1, IgG2, IgG3, IgG4) or IgM. Non-limiting examples of constant region sequences include:

Human IgD constant region, Uniprot: P01880
SEQ ID NO: 44
APTKAPDVFPIISGCRHPKDNSPVVLACLITGYHPTSVTVTWYMGTQS

QPQRTFPEIQRRDSYYMTSSQLSTPLQQWRQGEYKCVVQHTASKSKKE

IFRWPESPKAQASSVPTAQPQAEGSLAKATTAPATTRNTGRGGEEKKK

EKEKEEQEERETKTPECPSHTQPLGVYLLTPAVQDLWLRDKATFTCFV

VGSDLKDAHLTWEVAGKVPTGGVEEGLLERHSNGSQSQHSRLTLPRSL

WNAGTSVTCTLNHPSLPPQRLMALREPAAQAPVKLSLNLLASSDPPEA

ASWLLCEVSGFSPPNILLMWLEDQREVNTSGFAPARPPPQPGSTTFWA

WSVLRVPAPPSPQPATYTCVVSHEDSRTLLNASRSLEVSYVTDHGPMK

Human IgG1 constant region, Uniprot: P01857
SEQ ID NO: 45
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPGK

Human IgG2 constant region, Uniprot: P01859
SEQ ID NO: 46
ASTKGPSVFPLAPCSRSTSESTAALGCLVKDYFPEPVTVSWNSGALTS

GVHTFPAVLQSSGLYSLSSVVTVPSSNFGTQTYTCNVDHKPSNTKVDK

TVERKCCVECPPCPAPPVAGPSVFLFPPKPKDTLMISRTPEVTCVVVD

VSHEDPEVQFNWYVDGVEVHNAKTKPREEQFNSTFRVVSVLTVVHQDW

LNGKEYKCKVSNKGLPAPIEKTISKTKGQPREPQVYTLPPSREEMTKN

QVSLTCLVKGFYPSDISVEVVESNGQPENNYKTTPPMLDSDGSFFLYS

KLTVDKSRWQQGNVFSCSVMHEALHNHYTQKSLSLSPGK

Human IgG3 constant region, Uniprot: P01860
SEQ ID NO: 47
ASTKGPSVFPLAPCSRSTSGGTAALGCLVKDYFPEPVTVSWNSGALTS

GVHTFPAVLQSSGLYSLSSVVTVPSSSLGTQTYTCNVNHKPSNTKVDK

RVELKTPLGDTTHTCPRCPEPKSCDTPPPCPRCPEPKSCDTPPPCPRC

PEPKSCDTPPPCPRCPAPELLGGPSVFLFPPKPKDTLMISRTPEVTCV

VVDVSHEDPEVQFKWYVDGVEVHNAKTKPREEQYNSTFRVVSVLTVLH

QDWLNGKEYKCKVSNKALPAPIEKTISKTKGQPREPQVYTLPPSREEM

TKNQVSLTCLVKGFYPSDIAVEWESSGQPENNYNTTPPMLDSDGSFFL

YSKLTVDKSRWQQGNIFSCSVMHEALHNRFTQKSLSLSPGK

Human IgM constant region, Uniprot: P01871
SEQ ID NO: 48
GSASAPTLFPEVSCENSPSDTSSVAVGCLAQDFLPDSITLSWKYKNNS

DISSTRGFPSVLRGGKYAATSQVLLPSKDVMQGTDEHVVCKVQHPNGN

KEKNVPLPVIAELPPKVSVFVPPRDGFFGNPRKSKLICQATGFSPRQI

QVSWLREGKQVGSGVTTDQVQAEAKESGPTTYKVTSTLTIKESDWLGQ

SMFTCRVDHRGLTFQQNASSMCVPDQDTAIRVFAIPPSFASIFLTKST

KLTCLVTDLTTYDSVTISWTRQNGEAVKTHTNISESHPNATFSAVGEA

SICEDDWNSGERFTCTVTHTDLPSPLKQTISRPKGVALHRPDVYLLPP

AREQLNLRESATITCLVTGFSPADVFVQWMQRGQPLSPEKYVTSAPMP

EPQAPGRYFAHSILTVSEEEWNTGETYTCVAHEALPNRVTERTVDKST

GKPTLYNVSLVMSDTAGTCY

Human IgG4 constant region, Uniprot: P01861
SEQ ID NO: 49
ASTKGPSVFPLAPCSRSTSESTAALGCLVKDYFPEPVTVSWNSGALTS

GVHTFPAVLQSSGLYSLSSVVTVPSSSLGTKTYTCNVDHKPSNTKVDK

RVESKYGPPCPSCPAPEFLGGPSVFLFPPKPKDTLMISRTPEVTCVVV

DVSQEDPEVQFNWYVDGVEVHNAKTKPREEQFNSTYRVVSVLTVLHQD

WLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYS

RETVDKSRWQEGNVFSCSVMHEALFINHYTQKSLSLSLGK

Human IgA1 constant region, Uniprot: P01876
SEQ ID NO: 50
ASPTSPKVFPLSLCSTQPDGNVVIACLVQGFFPQEPLSVTWSESGQGV

TARNFPPSQDASGDLYTTSSQLTLPATQCLAGKSVTCHVKHYTNPSQD

VTVPCPVPSTPPTPSPSTPPTPSPSCCHPRLSLHRPALEDLLLGSEAN

LTCTLTGLRDASGVTFTWTPSSGKSAVQGPPERDLCGCYSVSSVLPGC

AEPWNHGKTFTCTAAYPESKTPLTATLSKSGNTFRPEVHLLPPPSEEL

ALNELVTLTCLARGFSPKDVLVRWLQGSQELPREKYLTWASRQEPSQG

TTTFAVTSILRVAAEDWKKGDTFSCMVGHEALPLAFTQKTIDRLAGKP

THVNVSVVMAEVDGTCY

Human IgA2 constant region, Uniprot: P01877
SEQ ID NO: 51
ASPTSPKVFPLSLDSTPQDGNVVVACLVQGFFPQEPLSVTWSESGQNV

TARNFPPSQDASGDLYTTSSQLTLPATQCPDGKSVTCHVKHYTNPSQD

VTVPCPVPPPPCCHPRLSLHRPALEDLLLGSEANLTCTLTGLRDASG

ATFTWTPSSGKSAVQGPPERDLCGCYSVSSVLPGCAQPWNHGETFTCT

AAHPELKTPLTANITKSGNTFRPEVHLLPPPSEELALNELVTLTCLAR

GFSPKDVLVRWLQGSQELPREKYLTWASRQEPSQGTTTFAVTSELRVA

AEDWKKGDTFSCMVGHEALPLAFTQKTIDRMAGKPTHVNVSVVMAEVD

GTCY

Human Ig kappa constant region, Uniprot: P01834
SEQ ID NO. 52
TVAAPSVFIFPPSDEQLKSGTASVVCLLNNFYPREAKVQWKVDNALQS

GNSQESVTEQDSKDSTYSLSSTLTLSKADYEKHKVYACEVTHQGLSSP

VTKSFNRGEC

In some aspects of the antibodies provided herein, the antibody contains structural modifications to facilitate rapid binding and cell uptake and/or slow release. In some aspects, the LHR antibody contains a deletion in the CH2 constant heavy chain region of the antibody to facilitate rapid binding and cell uptake and/or slow release. In some aspects, a Fab fragment is used to facilitate rapid binding and cell uptake and/or slow release. In some aspects, a F(ab)'2 fragment is used to facilitate rapid binding and cell uptake and/or slow release.

The antibodies, fragments, and equivalents thereof can be combined with a carrier, e.g., a pharmaceutically acceptable carrier or other agents to provide a formulation for use and/or storage.

Further provided is an isolated polypeptide comprising, or alternatively consisting essentially of, or yet further consisting of, the amino acid sequence of LHR or a fragment thereof, that are useful to generate antibodies that bind to LHR, as well as isolated polynucleotides that encode them. In one aspect, the isolated polypeptides or polynucleotides further comprise a label and/or contiguous polypeptide sequences (e.g., keyhole limpet haemocyanin (KLH) carrier protein) or in the case of polynucleotides, polynucleotides encoding the sequence, operatively coupled to polypeptide or polynucleotide. The polypeptides or polynucleotides can be combined with various carriers, e.g., phosphate buffered saline. Further provided are host cells, e.g., prokaryotic or eukaryotic cells, e.g., bacteria, yeast, mammalian (rat, simian, hamster, or human), comprising the isolated polypeptides or polynucleotides. The host cells can be combined with a carrier.

Yet further provided are the isolated nucleic acids encoding the antibodies and fragments thereof as disclosed herein. They can be combined with a vector or appropriate host cell, and/or a suitable carrier for diagnostic or therapeutic use. In one aspect, the nucleic acids are contained with a host cell for recombinant production of polypeptides and proteins. The host cells can be eukaryotic or prokaryotic.

II. Processes for Preparing Compositions

Antibodies, their manufacture and uses are well known and disclosed in, for example, Harlow, E. and Lane, D., *Antibodies: A Laboratory Manual*, Cold Spring Harbor Laboratory Press, Cold. Spring Harbor, N.Y., 1999. The antibodies may be generated using standard methods known in the art. Examples of antibodies include (but are not limited to) monoclonal, single chain, and functional fragments of antibodies.

Antibodies may be produced in a range of hosts, for example goats, rabbits, rats, mice, humans, and others. They may be immunized by injection with a target antigen or a fragment or oligopeptide thereof which has immunogenic properties, such as a C-terminal fragment of LHR or an isolated polypeptide. Depending on the host species, various adjuvants may be added and used to increase an immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (Bacille Calmette-Guerin) and *Corynebacterium parvum* are particularly useful. This this disclosure also provides the isolated polypeptide and an adjuvant.

In certain aspects, the antibodies of the present disclosure are polyclonal, i.e., a mixture of plural types of anti-LHR antibodies having different amino acid sequences. In one aspect, the polyclonal antibody comprises a mixture of plural types of anti-LHR antibodies having different CDRs. As such, a mixture of cells which produce different antibodies is cultured, and an antibody purified from the resulting culture can be used (see WO 2004/061104).

Monoclonal Antibody Production. Monoclonal antibodies to LHR may be prepared using any technique which provides for the production of antibody molecules by continuous cell lines in culture. Such techniques include, but are not limited to, the hybridoma technique (see, e.g., Kohler & Milstein, *Nature* 256: 495-497 (1975)); the trioma technique; the human B-cell hybridoma technique (see, e.g., Kozbor, et al., *Immunol. Today* 4: 72 (1983)) and the EBV hybridoma technique to produce human monoclonal antibodies (see, e.g., Cole, et al., in: MONOCLONAL ANTIBODIES AND CANCER THERAPY, Alan R. Liss, Inc., pp. 77-96 (1985)). Human monoclonal antibodies can be utilized in the practice of the present technology and can be produced by using human hybridomas (see, e.g., Cote, et al., *Proc. Natl. Acad. Sci.* 80: 2026-2030 (1983)) or by transforming human B-cells with Epstein Barr Virus in vitro (see, e.g., Cole, et al., in: MONOCLONAL ANTIBODIES AND CANCER THERAPY, Alan R. Liss, Inc., pp. 77-96 (1985)). For example, a population of nucleic acids that encode regions of antibodies can be isolated. PCR utilizing primers derived from sequences encoding conserved regions of antibodies is used to amplify sequences encoding portions of antibodies from the population and then reconstruct DNAs encoding antibodies or fragments thereof, such as variable domains, from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the LHR polypeptide.

Alternatively, hybridomas expressing anti-LHR monoclonal antibodies can be prepared by immunizing a subject, e.g., with an isolated polypeptide comprising, or alternatively consisting essentially of, or yet further consisting of, the amino acid sequence of LHR or a fragment thereof, and then isolating hybridomas from the subjects spleen using routine methods. See, e.g., Milstein el at., (Galfre and Milstein, *Methods Enzymol* 73: 3-46 (1981)). Screening the hybridomas using standard methods will produce monoclonal antibodies of varying specificity e., for different epitopes) and affinity. A selected monoclonal antibody with the desired properties, e.g., LHR binding, can be (i) used as expressed by the hybridoma, (ii) bound to a molecule such as polyethylene glycol (PEG) to alter its properties, or (iii) a cDNA encoding the monoclonal antibody can be isolated, sequenced and manipulated in various ways. In one aspect, the anti-LHR monoclonal antibody is produced by a hybridoma which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Harlow et al., *Antibodies: A Laboratory Manual* Cold Spring Harbor Laboratory, Cold Spring Harbor, N.Y., 349 (1988); Hammerling et al., *Monoclonal Antibodies And T-Cell Hybridomas,* 563-681 (1981).

Phage Display Technique. As noted above, the antibodies of the present disclosure can be produced through the application of recombinant DNA and phage display technology. For example, anti-LHR antibodies, can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g., human or murine) by selecting directly with an antigen, typically an antigen bound or captured to a solid surface or bead. Phage used in these methods are typically filamentous phage including fd and M13 with Fab, $F_v$ or disulfide stabilized $F_v$ antibody domains are recombinantly fused to either the phage gene III or gene VIII protein. In addition, methods can be adapted for the construction of Fab expression libraries (see, e.g., Huse, et al., *Science* 246: 1275-1281, 1989) to allow rapid and effective identification of monoclonal Fab fragments with the desired specificity for a LHR polypeptide, e.g., a polypeptide or derivatives, fragments, analogs or homologs thereof. Other examples of phage display methods that can be used to make the isolated antibodies of the present disclosure include those disclosed in Huston et al., *Proc. Natl. Acad. Sci. U.S.A.,* 85: 5879-5883 (1988); Chaudhary et al., *Proc. Natl. Acad. Sci. U.S.A.,* 87: 1066-1070 (1990); Brinkman et al., *J. Immunol. Methods* 182: 41-50 (1995); Ames et al., *J. Immunol. Methods* 184: 177-186 (1995); Kettleborough et al., *Eur. J. Immunol.* 24: 952-958 (1994); Persic et al., *Gene* 187: 9-18 (1997); Burton et at., *Advances in Immunology* 57: 191-280 (1994); PCT/GB91/01134; WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743.

Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')$_2$ fragments can also be employed using methods known in the art such as those disclosed in WO 92/22324; Mullinax et al., *BioTechniques* 12: 864-869 (1992); Sawai et al., *AJRI* 34: 26-34 (1995); and Better et al., *Science* 240: 1041-1043 (1988).

Generally, hybrid antibodies or hybrid antibody fragments that are cloned into a display vector can be selected against the appropriate antigen in order to identify variants that maintained good binding activity, because the antibody or antibody fragment will be present on the surface of the phage or phagemid particle. See e.g. Barbas III et al., *Phage Display, A Laboratory Manual* (Cold Spring Harbor Laboratory Press, Cold Spring Harbor, N.Y., 2001). However, other vector formats could be used for this process, such as cloning the antibody fragment library into a lytic phage vector or (modified T7 or Lambda Zap systems) for selection and/or screening.

Alternate Methods of Antibody Production. Antibodies may also be produced by inducing in vivo production in the lymphocyte population or by screening recombinant immunoglobulin libraries or panels of highly specific binding reagents (Orlandi et al., *PNAS* 86: 3833-3837 (1989); Winter, G. et al., *Nature*, 349: 293-299 (1991)).

Alternatively, techniques for the production of single chain antibodies may be used. Single chain antibodies (scF$_v$s) comprise a heavy chain variable region and a light chain variable region connected with a linker peptide (typically around 5 to 25 amino acids in length). In the scF$_v$, the variable regions of the heavy chain and the light chain may be derived from the same antibody or different antibodies. scF$_v$s may be synthesized using recombinant techniques, for example by expression of a vector encoding the scF$_v$ in a host organism such as *E. coli*. DNA encoding scF$_v$ can be obtained by performing amplification using a partial DNA encoding the entire or a desired amino acid sequence of a DNA selected from a DNA encoding the heavy chain or the variable region of the heavy chain of the above-mentioned antibody and a DNA encoding the light chain or the variable region of the light chain thereof as a template, by PCR using a primer pair that defines both ends thereof, and further performing amplification combining a DNA encoding a polypeptide linker portion and a primer pair that defines both ends thereof, so as to ligate both ends of the linker to the heavy chain and the light chain, respectively. An expression vector containing the DNA encoding scF$_v$ and a host transformed by the expression vector can be obtained according to conventional methods known in the art.

Antigen binding fragments may also be generated, for example the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse et al., *Science*, 256: 1275-1281 (1989)).

Antibody Modifications. The antibodies of the present disclosure may be multimerized to increase the affinity for an antigen. The antibody to be multimerized may be one type of antibody or a plurality of antibodies which recognize a plurality of epitopes of the same antigen. As a method of multimerization of the antibody, binding of the IgG CH3 domain to two scF$_v$ molecules, binding to streptavidin, introduction of a helix-turn-helix motif and the like can be exemplified.

The antibody compositions disclosed herein may be in the form of a conjugate formed between any of these antibodies and another agent (immunoconjugate). In one aspect, the antibodies disclosed herein are conjugated to radioactive material. In another aspect, the antibodies disclosed herein can be bound to various types of molecules such as polyethylene glycol (PEG).

Antibody Screening. Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between LHR, or any fragment or oligopeptide thereof and its specific antibody. A two-site, monoclonal-based immunoassay utilizing monoclonal antibodies specific to two non-interfering LHR epitopes may be used, but a competitive binding assay may also be employed (Maddox et al., *J. Exp. Med.*, 158: 1211-1216 (1983)).

Automated immunohistochemistry (IHC) screening of potential anti-LHR antibodies can be performed using a Ventana Medical Systems, Inc (VMSI) Discovery XT and formalin-fixed, paraffin-embedded human tissue on glass slides. Tissue samples first undergo deparaffinization, antigen retrieval, followed by the addition of the potential anti-LHR antibody and a detection antibody. The detection antibody is visualized using a chromogen detection reagent from VMSI. Stained slides are manually screened under a microscope. Samples having a correct primary antibody staining pattern are selected as potential anti-LHR candidates.

Antibody Purification. The antibodies disclosed herein can be purified to homogeneity. The separation and purification of the antibodies can be performed by employing conventional protein separation and purification methods.

By way of example only, the antibody can be separated and purified by appropriately selecting and combining use of chromatography columns, filters, ultrafiltration, salt precipitation, dialysis, preparative polyacrylamide gel electrophoresis, isoelectric focusing electrophoresis, and the like. *Strategies for Protein Purification and Characterization: A Laboratory Course Manual*, Daniel R. Marshak et al. eds., Cold Spring Harbor Laboratory Press (1996); *Antibodies: A Laboratory Manual*. Ed Harlow and David Lane, Cold Spring Harbor Laboratory (1988).

Examples of chromatography include affinity chromatography, ion exchange chromatography, hydrophobic chromatography, gel filtration chromatography, reverse phase chromatography, and adsorption chromatography. In one aspect, chromatography can be performed by employing liquid chromatography such as HPLC or FPLC.

In one aspect, a Protein A column or a Protein G column may be used in affinity chromatography. Other exemplary columns include a Protein A column, Hyper D, POROS, Sepharose F. F. (Pharmacia) and the like.

III. Methods of Use

General. The antibodies disclosed herein are useful in methods known in the art relating to the localization and/or quantitation of a LHR polypeptide (e.g., for use in measuring levels of the LHR polypeptide within appropriate physiological samples, for use in diagnostic methods, for use in imaging the polypeptide, and the like). The antibodies disclosed herein are useful in isolating a LHR polypeptide by standard techniques, such as affinity chromatography or immunoprecipitation. A LHR antibody disclosed herein can facilitate the purification of natural LHR polypeptides from biological samples, e.g., mammalian sera or cells as well as recombinantly-produced LHR polypeptides expressed in a host system. Moreover, LHR antibody can be used to detect a LHR polypeptide (e.g., in plasma, a cellular lysate or cell supernatant) in order to evaluate the abundance and pattern of expression of the polypeptide. The LHR antibodies disclosed herein can be used diagnostically to monitor LHR levels in tissue as part of a clinical testing procedure, e.g., to determine the efficacy of a given treatment regimen. The detection can be facilitated by coupling (i.e., physically linking) the LHR antibodies disclosed herein to a detectable substance.

In another aspect, provided herein is a composition comprising an antibody or antigen binding fragment as disclosed herein bound to a peptide comprising, for example, a human LHR protein or a fragment thereof. In one aspect, the peptide is associated with a cell. For example, the composition may comprise a disaggregated cell sample labeled with an antibody or antibody fragment as disclosed herein, which composition is useful in, for example, affinity chromatography methods for isolating cells or for flow cytometry-based cellular analysis or cell sorting. As another example, the composition may comprise a fixed tissue sample or cell smear labeled with an antibody or antibody fragment as disclosed herein, which composition is useful in, for example, immunohistochemistry or cytology analysis. In another aspect, the antibody or the antibody fragment is bound to a solid support, which is useful in, for example: ELISAs; affinity chromatography or immunoprecipitation methods for isolating LHR proteins or fragments thereof, LHR-positive cells, or complexes containing LHR and other cellular components. In another aspect, the peptide is bound to a solid support. For example, the peptide may be bound to the solid support via a secondary antibody specific for the peptide, which is useful in, for example, sandwich ELISAs. As another example, the peptide may be bound to a chromatography column, which is useful in, for example, isolation or purification of antibodies according to the present technology. In another aspect, the peptide is disposed in a solution, such as a lysis solution or a solution containing a sub-cellular fraction of a fractionated cell, which is useful in, for example, ELISAs and affinity chromatography or immunoprecipitation methods of isolating LHR proteins or fragments thereof or complexes containing LHR and other cellular components. In another aspect, the peptide is associated with a matrix, such as, for example, a gel electrophoresis gel or a matrix commonly used for western blotting (such as membranes made of nitrocellulose or polyvinylidene difluoride), which compositions are useful for electrophoretic and/or immunoblotting techniques, such as Western blotting.

Detection of LHR Polypeptide. An exemplary method for detecting the level of LHR polypeptides in a biological sample involves obtaining a biological sample from a subject and contacting the biological sample with a LHR antibody disclosed herein which is capable of detecting the LHR polypeptides.

In one aspect, the LHR antibodies 5F4-21, 4A7-4, 8B7-3, or 138-2, or fragments thereof are detectably labeled. The term "labeled", with regard to the antibody is intended to encompass direct labeling of the antibody by coupling (i.e., physically linking) a detectable substance to the antibody, as well as indirect labeling of the antibody by reactivity with another compound that is directly labeled. Non-limiting examples of indirect labeling include detection of a primary antibody using a fluorescently-labeled secondary antibody and end-labeling of a DNA probe with biotin such that it can be detected with fluorescently-labeled streptavidin.

The detection method of the present disclosure can be used to detect expression levels of LHR polypeptides in a biological sample in vitro as well as in vivo. In vitro techniques for detection of LHR polypeptides include enzyme linked immunosorbent assays (ELISAs), Western blots, flow cytometry, immunoprecipitations, radioimmunoassay, and immunofluorescence (e.g., IHC). Furthermore, in vivo techniques for detection of LHR polypeptides include introducing into a subject a labeled anti-LHR antibody. By way of example only, the antibody can be labeled with a radioactive marker whose presence and location in a subject can be detected by standard imaging techniques. In one aspect, the biological sample contains polypeptide molecules from the test subject.

Immunoassay and Imaging. A LHR antibody disclosed herein can be used to assay LHR polypeptide levels in a biological sample (e.g. human plasma) using antibody-based techniques. For example, protein expression in tissues can be studied with classical immunohistochemical (IHC) staining methods. Jalkanen, M. et al., *J. Cell. Biol.* 101: 976-985 (1985); Jalkanen, M. et al., *J. Cell. Biol.* 105: 3087-3096 (1987). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes or other radioactive agents, such as iodine ($^{125}$I, $^{121}$I, $^{131}$I), carbon ($^{14}$C), sulfur ($^{35}$S), tritium ($^{3}$H), indium ($^{112}$In), and technetium ($^{99}$mTc), and fluorescent labels, such as fluorescein and rhodamine, and biotin.

In addition to assaying LHR polypeptide levels in a biological sample, LHR polypeptide levels can also be detected in vivo by imaging. Labels that can be incorporated with anti-LHR antibodies for in vivo imaging of LHR polypeptide levels include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the LHR antibody by labeling of nutrients for the relevant scF$_v$ clone.

A LHR antibody which has been labeled with an appropriate detectable imaging moiety, such as a radioisotope (e.g., $^{131}$I, $^{112}$In, $^{99}$mTc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled LHR antibody will then preferentially accumulate at the location of cells which contain the specific target polypeptide. For example, in vivo tumor imaging is described in S. W. Burchiel et al., *Tumor Imaging: The Radiochemical Detection of Cancer* 13 (1982).

In some aspects, LHR antibodies containing structural modifications that facilitate rapid binding and cell uptake and/or slow release are useful in in vivo imaging detection methods. In some aspects, the LHR antibody contains a deletion in the CH2 constant heavy chain region of the antibody to facilitate rapid binding and cell uptake and/or slow release. In some aspects, a Fab fragment is used to facilitate rapid binding and cell uptake and/or slow release. In some aspects, a F(ab)'2 fragment is used to facilitate rapid binding and cell uptake and/or slow release.

Diagnostic Uses of LHR antibodies. The LHR antibody compositions disclosed herein are useful in diagnostic and prognostic methods. As such, the present disclosure provides methods for using the antibodies disclosed herein in the diagnosis of LHR-related medical conditions in a subject. Antibodies disclosed herein may be selected such that they have a high level of epitope binding specificity and high binding affinity to the polypeptide. In general, the higher the binding affinity of an antibody, the more stringent wash conditions can be performed in an immunoassay to remove nonspecifically bound material without removing the target polypeptide. Accordingly, LHR antibodies of the present technology useful in diagnostic assays usually have binding affinities of at least $10^{-6}$, $10^{-7}$, $10^{-8}$, $10^{-9}$, $10^{-10}$, $10^{-11}$, or $10^{-12}$ M. In certain aspects, LHR antibodies used as diagnostic reagents have a sufficient kinetic on-rate to reach equilibrium under standard conditions in at least 12 hours, at least 5 hours, at least 1 hour, or at least 30 minutes.

Some methods of the present technology employ polyclonal preparations of anti-LHR antibodies and polyclonal anti-LHR antibody compositions as diagnostic reagents, and other methods employ monoclonal isolates. In methods employing polyclonal human anti-LHR antibodies prepared in accordance with the methods described above, the preparation typically contains an assortment of LHR antibodies, e.g., antibodies, with different epitope specificities to the target polypeptide. The monoclonal anti-LHR antibodies of the present disclosure are useful for detecting a single antigen in the presence or potential presence of closely related antigens.

The LHR antibodies of the present disclosure can be used as diagnostic reagents for any kind of biological sample. In one aspect, the LHR antibodies disclosed herein are useful as diagnostic reagents for human biological samples. LHR antibodies can be used to detect LHR polypeptides in a variety of standard assay formats. Such formats include immunoprecipitation, Western blotting, ELISA, radioimmunoassay, flow cytometry, IHC and immunometric assays. See Harlow & Lane, *Antibodies, A Laboratory Manual* (Cold Spring Harbor Publications, New York, 1988); U.S. Pat. Nos. 3,791,932; 3,839,153; 3,850,752; 3,879,262; 4,034,074, 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Biological samples can be obtained from any tissue (including biopsies), cell or body fluid of a subject.

Prognostic Uses of LHR antibodies. The present disclosure also provides for prognostic (or predictive) assays for determining whether a subject is at risk of developing a medical disease or condition associated with increased LHR polypeptide expression or activity (e.g., detection of a precancerous cell). Such assays can be used for prognostic or predictive purpose to thereby prophylactically treat an individual prior to the onset of a medical disease or condition characterized by or associated with LHR polypeptide expression.

Another aspect of the present disclosure provides methods for determining LHR expression in a subject to thereby select appropriate therapeutic or prophylactic compounds for that subject.

Alternatively, the prognostic assays can be utilized to identify a subject having or at risk for developing prostate cancer and ovary cancer. Thus, the present disclosure provides a method for identifying a disease or condition associated with increased LHR polypeptide expression levels in which a test sample is obtained from a subject and the LHR polypeptide detected, wherein the presence of increased levels of LHR polypeptides compared to a control sample is predictive for a subject having or at risk of developing a disease or condition associated with increased LHR polypeptide expression levels. In some aspects, the disease or condition associated with increased LHR polypeptide expression levels is selected from the group consisting of prostate cancer and ovary cancer.

In another aspect, the present disclosure provides methods for determining whether a subject can be effectively treated with a compound for a disorder or condition associated with increased LHR polypeptide expression wherein a biological sample is obtained from the subject and the LHR polypeptide is detected using the LHR antibody. The expression level of the LHR polypeptide in the biological sample obtained from the subject is determined and compared with the LHR expression levels found in a biological sample obtained from a subject who is free of the disease. Elevated levels of the LHR polypeptide in the sample obtained from the subject suspected of having the disease or condition compared with the sample obtained from the healthy subject is indicative of the LHR-associated disease or condition in the subject being tested.

There are a number of disease states in which the elevated expression level of LHR polypeptides is known to be indicative of whether a subject with the disease is likely to respond to a particular type of therapy or treatment. Thus, the method of detecting a LHR polypeptide in a biological sample can be used as a method of prognosis, e.g., to evaluate the likelihood that the subject will respond to the therapy or treatment. The level of the LHR polypeptide in a suitable tissue or body fluid sample from the subject is determined and compared with a suitable control, e.g., the level in subjects with the same disease but who have responded favorably to the treatment.

In one aspect, the present disclosure provides for methods of monitoring the influence of agents (e.g., drugs, compounds, or small molecules) on the expression of LHR polypeptides. Such assays can be applied in basic drug screening and in clinical trials. For example, the effectiveness of an agent to decrease LHR polypeptide levels can be monitored in clinical trials of subjects exhibiting elevated expression of LHR, e.g., patients diagnosed with cancer. An agent that affects the expression of LHR polypeptides can be identified by administering the agent and observing a response. In this way, the expression pattern of the LHR polypeptide can serve as a marker, indicative of the physiological response of the subject to the agent. Accordingly, this response state may be determined before, and at various points during, treatment of the subject with the agent.

Further aspects of the present disclosure relate to methods for determining if a patient is likely to respond or is not likely to LHR CAR therapy. In specific embodiments, this method comprises contacting a tumor sample isolated from the patient with an effective amount of an LHR antibody and detecting the presence of any antibody bound to the tumor sample. In further embodiments, the presence of antibody bound to the tumor sample indicates that the patient is likely to respond to the LHR CAR therapy and the absence of antibody bound to the tumor sample indicates that the patient is not likely to respond to the LHR therapy. In some embodiments, the method comprises the additional step of administering an effective amount of the LHR CAR therapy to a patient that is determined likely to respond to the LHR CAR therapy.

Automated Embodiments. A person of ordinary skill in the art will appreciate that aspects of the methods for using the LHR antibodies disclosed herein can be automated. Particular aspects of LHR staining procedures can be conducted using various automated processes.

IV. Kits

As set forth herein, the present disclosure provides diagnostic methods for determining the expression level of LHR. In one particular aspect, the present disclosure provides kits for performing these methods as well as instructions for carrying out the methods of the present disclosure such as collecting tissue and/or performing the screen, and/or analyzing the results.

The kit comprises, or alternatively consists essentially of, or yet further consists of, a LHR antibody composition (e.g., monoclonal antibodies) disclosed herein, and instructions for use. The kits are useful for detecting the presence of LHR polypeptides in a biological sample e.g., any body fluid including, but not limited to, e.g., sputum, serum, plasma, lymph, cystic fluid, urine, stool, cerebrospinal fluid, acitic fluid or blood and including biopsy samples of body tissue. The test samples may also be a tumor cell, a normal cell adjacent to a tumor, a normal cell corresponding to the tumor tissue type, a blood cell, a peripheral blood lymphocyte, or combinations thereof. The test sample used in the above-described method will vary based on the assay format, nature of the detection method and the tissues, cells or extracts used as the sample to be assayed. Methods for preparing protein extracts or membrane extracts of cells are known in the art and can be readily adapted in order to obtain a sample which is compatible with the system utilized.

In some aspects, the kit can comprise: one or more LHR antibodies capable of binding a LHR polypeptide in a biological sample (e.g., an antibody or antigen-binding fragment thereof having the same antigen-binding specificity of LHR antibody B7H4 5F6, B7H4 #33-14, or B7H4 #36-1); means for determining the amount of the LHR polypeptide in the sample; and means for comparing the amount of the LHR polypeptide in the sample with a standard. One or more of the LHR antibodies may be labeled. The kit components, (e.g., reagents) can be packaged in a suitable container. The kit can further comprise instructions for using the kit to detect the LHR polypeptides. In certain aspects, the kit comprises a first antibody, e.g., attached to a solid support, which binds to a LHR polypeptide; and, optionally; 2) a second, different antibody which binds to either the LHR polypeptide or the first antibody and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present disclosure may contain a written product on or in the kit container. The written product describes how to use the reagents contained in the kit.

As amenable, these suggested kit components may be packaged in a manner customary for use by those of skill in the art. For example, these suggested kit components may be provided in solution or as a liquid dispersion or the like.

V. Carriers

The antibodies or LHR CARS also can be bound to many different carriers. Thus, this disclosure also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the disclosure. Those skilled in the art will know of other suitable carriers for binding antibodies, or will be able to ascertain such, using routine experimentation.

Chimeric Antigen Receptors and Uses Thereof

I. Compositions

The present disclosure provides chimeric antigen receptors (CAR) that bind to LHR comprising, or consisting essentially of, an extracellular and intracellular domain. The extracellular domain comprises a target-specific binding element otherwise referred to as the antigen binding domain. The intracellular domain or cytoplasmic domain comprises a costimulatory signaling region and a zeta chain portion. The CAR may optionally further comprise a spacer domain of up to 300 amino acids, preferably 10 to 100 amino acids, more preferably 25 to 50 amino acids.

Antigen Binding Domain. In certain aspects, the present disclosure provides a CAR that comprises, or alternatively consists essentially thereof, or yet consists of an antigen binding domain specific to LHR. In some embodiments, the antigen binding domain comprises, or alternatively consists essentially thereof, or yet consists of the antigen binding domain of an anti-LHR antibody. In further embodiments, the heavy chain variable region and light chain variable region of an anti-LHR antibody comprises, or alternatively consists essentially thereof, or yet consists of the antigen binding domain the anti-LHR antibody. These antibodies and their sequences are disclosed herein. As is apparent to the skilled artisan, the antibody fragments against LHR as disclosed herein can be used to generate a CAR. Thus, the relevant disclosure is incorporated herein.

In some embodiments, the heavy chain variable region of the antibody comprises, or consists essentially thereof, or consists of the sequences disclosed herein, including an equivalent of each thereof and/or comprises one or more CDR regions as disclosed herein or an equivalent of each thereof. In one aspect, the HC of the antibody comprises or alternatively consists essentially of, or yet further consists of one or more of: a CDR1 comprising the amino acid sequence of GYSITSGYG (SEQ ID NO.: 16) or an equivalent of each thereof; and/or a CDR2 comprising the amino acid sequence of IHYSGST (SEQ ID NO.: 19) or an equivalent of each thereof, and/or a CDR3 comprising the amino acid sequence of ARSLRY (SEQ ID NO.: 22) or an equivalent of each thereof; and/or the LC comprises the antibody of comprises or alternatively consists essentially of, or yet further consists of a CDR1 comprising the amino acid sequence of SSVNY (SEQ ID NO.:25) or an equivalent of each thereof; and/or a CDR2 comprising the amino acid sequence of DTS (SEQ ID NO:28) or an equivalent of each thereof; and/or a CDR3 comprising the amino acid sequence of HQWSSYPYT (SEQ ID NO:3) or an equivalent of each thereof.

In one aspect, the HC comprises, or alternatively consists essentially of, or yet further consists of one or more of: a CDR1 comprising the amino acid sequence of GFSLTTYG (SEQ ID NO.: 17) or an equivalent of each thereof; and/or a CDR2 comprising the amino acid sequence of IWGDGST (SEQ ID NO.: 20) or an equivalent of each thereof; and/or a CDR3 comprising the amino acid sequence of AEGSSLFAY (SEQ ID NO.: 23) or an equivalent of each thereof; and/or the LC of the antibody comprises, or alternatively consists essentially of, or yet further consists of a CDR1 comprising the amino acid sequence of QSLLNSGNQKNY (SEQ ID NO.:26) or an equivalent of each thereof; and/or a CDR2 comprising the amino acid sequence of WAS (SEQ ID NO:29) or an equivalent of each thereof; and/or a CDR3 comprising the amino acid sequence of QNDYSYPLT (SEQ ID NO:32) or an equivalent of each thereof.

In another aspect, the HC of the antibody comprises, or alternatively consists essentially of, or yet further consists of one or more of: a CDR1 comprising the amino acid sequence of GYSFTGYY (SEQ ID NO.: 18) or an equivalent of each thereof; and/or a CDR2 comprising the amino acid sequence of IYPYNGVS (SEQ ID NO.: 21) or an equivalent of each thereof; and/or a CDR3 comprising the amino acid sequence of ARERGLYQLRAMDY (SEQ ID NO.: 24) or an equivalent of each thereof; and/or the LC of the antibody comprises, or alternatively consists essentially of, or yet further consists of a CDR1 comprising the amino acid sequence of QSISNN (SEQ ID NO.:27) or an equivalent of each thereof; and/or a CDR2 comprising the amino acid sequence of NAS (SEQ ID NO:30) or an equivalent of each thereof; and/or a CDR3 comprising the amino acid sequence of QQSNSWPYT (SEQ ID NO:33) or an equivalent of each thereof.

Transmembrane Domain. The transmembrane domain may be derived either from a natural or from a synthetic source. Where the source is natural, the domain may be derived from any membrane-bound or transmembrane protein. Transmembrane regions of particular use in this invention may be derived from CD8, CD28, CD3, CD45, CD4, CD5, CDS, CD9, CD 16, CD22, CD33, CD37, CD64, CD80, CD86, CD 134, CD137, CD 154, TCR. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Cytoplasmic Domain. The cytoplasmic domain or intracellular signaling domain of the CAR is responsible for activation of at least one of the traditional effector functions of an immune cell in which a CAR has been placed. The intracellular signaling domain refers to a portion of a protein which transduces the effector function signal and directs the immune cell to perform its specific function. An entire signaling domain or a truncated portion thereof may be used so long as the truncated portion is sufficient to transduce the effector function signal. Cytoplasmic sequences of the TCR and co-receptors as well as derivatives or variants thereof can function as intracellular signaling domains for use in a CAR. Intracellular signaling domains of particular use in this invention may be derived from FcR, TCR, CD3, CDS, CD22, CD79a, CD79b, CD66d. Since signals generated through the TCR are alone insufficient for full activation of a T cell, a secondary or co-stimulatory signal may also be required. Thus, the intracellular region of a co-stimulatory signaling molecule, including but not limited CD27, CD28, 4-IBB (CD 137), OX40, CD30, CD40, PD-1, ICOS, lymphocyte function-associated antigen-1 (LFA-1), CD2, CD7, LIGHT, NKG2C, B7-H3, or a ligand that specifically binds with CD83, to may also be included in the cytoplasmic domain of the CAR.

In some embodiments, the cell activation moiety of the chimeric antigen receptor is a T-cell signaling domain comprising, or alternatively consisting essentially of, or yet further consisting of, one or more proteins or fragments thereof selected from the group consisting of CD8 protein, CD28 protein, 4-1BB protein, and CD3-zeta protein.

In specific embodiments, the CAR comprises, or alternatively consists essentially thereof, or yet consists of an antigen binding domain of an anti-LHR antibody, a CD8 α hinge domain, a CD8 α transmembrane domain, a costimulatory signaling region, and a CD3 zeta signaling domain. In further embodiments, the costimulatory signaling region comprises either or both a CD28 costimulatory signaling region and a 4-1BB costimulatory signaling region.

In some embodiments, the CAR can further comprise a detectable marker or purification marker.

II. Process for Preparing CARS

Aspects of the present disclosure relate to an isolated cell comprising a LHR CAR and methods of producing such cells. The cell is a prokaryotic or a eukaryotic cell. In one aspect, the cell is a T cell or an NK cell. The eukaryotic cell can be from any preferred species, e.g., an animal cell, a mammalian cell such as a human, a feline or a canine cell.

In specific embodiments, the isolated cell comprises, or alternatively consists essentially of, or yet further consists of an exogenous CAR comprising, or alternatively consisting essentially of, or yet further consisting of, an antigen binding domain of an anti-LHR antibody, a CD8 α hinge domain, a CD8 α transmembrane domain, a CD28 costimulatory signaling region and/or a 4-1BB costimulatory signaling region, and a CD3 zeta signaling domain. In certain embodiments, the isolated cell is a T-cell, e.g., an animal T-cell, a mammalian T-cell, a feline T-cell, a canine T-cell or a human T-cell. In certain embodiments, the isolated cell is an NK-cell, e.g., an animal NK-cell, a mammalian NK-cell, a feline NK-cell, a canine NK-cell or a human NK-cell.

In certain embodiments, methods of producing LHR CAR expressing cells are disclosed comprising, or alternatively consisting essentially of: (i) transducing a population of isolated cells with a nucleic acid sequence encoding a LHR CAR and (ii) selecting a subpopulation of cells that have been successfully transduced with said nucleic acid sequence of step (i). In some embodiments, the isolated cells are T-cells, an animal T-cell, a mammalian T-cell, a feline T-cell, a canine T-cell or a human T-cell, thereby producing LHR CAR T-cells. In certain embodiments, the isolated cell is an NK-cell, e.g., an animal NK-cell, a mammalian NK-cell, a feline NK-cell, a canine NK-cell or a human NK-cell, thereby producing LHR CAR NK-cells.

Sources of T Cells or NK Cells. Prior to expansion and genetic modification of the T cells of the invention, a source of T or NK cells is obtained may be obtain from a subject or a culture. T or NK cells can be obtained from a number of sources in a subject, including peripheral blood mononuclear cells, bone marrow, lymph node tissue, cord blood, thymus tissue, tissue from a site of infection, ascites, pleural effusion, spleen tissue, and tumors.

Methods of isolating relevant cells are well known in the art and can be readily adapted to the present application; an exemplary method is described in the examples below. Isolation methods for use in relation to this disclosure include, but are not limited to Life Technologies Dynabeads® system; STEMcell Technologies EasySep™, RoboSep™, RosetteSep™, SepMate™; Miltenyi Biotec MACS™ cell separation kits, and other commercially available cell separation and isolation kits. Particular subpopulations of immune cells may be isolated through the use of beads or other binding agents available in such kits specific to unique cell surface markers. For example, MACS™ CD4+ and CD8+ MicroBeads may be used to isolate CD4+ and CD8+ T-cells.

Alternatively, cells may be obtained through commercially available cell cultures, including but not limited to, for T-cells, lines BCL2 (AAA) Jurkat (ATCC® CRL-2902™), BCL2 (S70A) Jurkat (ATCC® CRL-2900™), BCL2 (S87A) Jurkat (ATCC® CRL-2901™), BCL2 Jurkat (ATCC® CRL-2899™) Neo Jurkat (ATCC® CRL-2898™); and, for NK cells, lines NK-9 (ATCC® CRL-2407™), NK-92MI (ATCC® CRL-2408™).

Vectors. CARs may be prepared using vectors. The preparation of exemplary vectors and the generation of CAR expressing cells using said vectors is discussed in detail in the examples below. In summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes.

Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In some embodiments, the isolated nucleic acid sequence encodes for a CAR comprising, or alternatively consisting essentially of, or yet further consisting of an antigen binding domain of an anti-LHR antibody, a CD8 α hinge domain, a CD8 α transmembrane domain, a CD28 costimulatory signaling region and/or a 4-1BB costimulatory signaling region, and a CD3 zeta signaling domain. In specific embodiments, the isolated nucleic acid sequence comprises, or alternatively consisting essentially thereof, or yet further consisting of, sequences encoding (a) an antigen binding domain of an anti-LHR antibody followed by (b) a CD8 α hinge domain, (c) a CD8 α transmembrane domain followed by (d) a CD28 costimulatory signaling region and/or a 4-1BB costimulatory signaling region followed by (e) a CD3 zeta signaling domain.

In some embodiments, the isolated nucleic acid sequence comprises, or alternatively consists essentially thereof, or yet further consists of, a Kozak consensus sequence upstream of the sequence encoding the antigen binding domain of the anti-LHR antibody. In some embodiments, the isolated nucleic acid comprises a polynucleotide conferring antibiotic resistance.

In some embodiments, the isolated nucleic acid sequence is comprised in a vector. In certain embodiments, the vector is a plasmid. In other embodiments, the vector is a viral vector. In specific embodiments, the vector is a lentiviral vector.

The preparation of exemplary vectors and the generation of CAR expressing cells using said vectors is discussed in detail in the examples below. In summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

In one aspect, the term "vector" intends a recombinant vector that retains the ability to infect and transduce non-dividing and/or slowly-dividing cells and integrate into the target cell's genome. In several aspects, the vector is derived from or based on a wild-type virus. In further aspects, the vector is derived from or based on a wild-type lentivirus. Examples of such, include without limitation, human immunodeficiency virus (HIV), equine infectious anemia virus (EIAV), simian immunodeficiency virus (SIV) and feline immunodeficiency virus (FIV). Alternatively, it is contemplated that other retrovirus can be used as a basis for a vector backbone such murine leukemia virus (MLV). It will be evident that a viral vector according to the disclosure need not be confined to the components of a particular virus. The viral vector may comprise components derived from two or more different viruses, and may also comprise synthetic components. Vector components can be manipulated to obtain desired characteristics, such as target cell specificity.

The recombinant vectors of this disclosure are derived from primates and non-primates. Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anemia virus (EIAV) and the more recently described feline immunodeficiency virus (FIV) and bovine immunodeficiency virus (BIV). Prior art recombinant lentiviral vectors are known in the art, e.g., see U.S. Pat. Nos. 6,924,123; 7,056,699; 7,07,993; 7,419,829 and 7,442,551, incorporated herein by reference.

U.S. Pat. No. 6,924,123 discloses that certain retroviral sequence facilitate integration into the target cell genome. This patent teaches that each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome. The LTRs themselves are identical sequences that can be divided into three elements, which are called U3, R and U5. U3 is derived from the sequence unique to the 3' end of the RNA. R is derived from a sequence repeated at both ends of the RNA, and U5 is derived from the sequence unique to the 5' end of the RNA. The sizes of the three elements can vary considerably among different retroviruses. For the viral genome and the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome.

For the production of viral vector particles, the vector RNA genome is expressed from a DNA construct encoding it, in a host cell. The components of the particles not encoded by the vector genome are provided in trans by additional nucleic acid sequences "packaging system", which usually includes either or both of the gag/pol and env genes) expressed in the host cell. The set of sequences required for the production of the viral vector particles may be introduced into the host cell by transient transfection, or they may be integrated into the host cell genome, or they may be provided in a mixture of ways. The techniques involved are known to those skilled in the art.

Retroviral vectors for use in this disclosure include, but are not limited to Invitrogen's pLenti series versions 4, 6, and 6.2 "ViraPower" system. Manufactured by Lentigen Corp.; pHIV-7-GFP, lab generated and used by the City of Hope Research Institute; "Lenti-X" lentiviral vector, pLVX, manufactured by Clontech; pLKO.1-puro, manufactured by Sigma-Aldrich; pLemiR, manufactured by Open Biosystems; and pLV, lab generated and used by Charité Medical School, institute of Virology (CBF), Berlin, Germany.

Regardless of the method used to introduce exogenous nucleic acids into a host cell or otherwise expose a cell to the inhibitor of the present disclosure, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the disclosure.

Packaging vector and cell lines. CARs can be packaged into a retroviral packaging system by using a packaging vector and cell lines. The packaging plasmid includes, but is not limited to retroviral vector, lentiviral vector, adenoviral vector, and adeno-associated viral vector. The packaging vector contains elements and sequences that facilitate the delivery of genetic materials into cells. For example, the retroviral constructs are packaging plasmids comprising at least one retroviral helper DNA sequence derived from a replication-incompetent retroviral genome encoding in trans all virion proteins required to package a replication incompetent retroviral vector, and for producing virion proteins capable of packaging the replication-incompetent retroviral vector at high titer, without the production of replication-competent helper virus. The retroviral DNA sequence lacks the region encoding the native enhancer and/or promoter of the viral 5' LTR of the virus, and lacks both the psi function sequence responsible for packaging helper genome and the 3' LTR, but encodes a foreign polyadenylation site, for example the SV40 polyadenylation site, and a foreign enhancer and/or promoter which directs efficient transcription in a cell type where virus production is desired. The retrovirus is a leukemia virus such as a Moloney Murine Leukemia Virus (MMLV), the Human Immunodeficiency Virus (HIV), or the Gibbon Ape Leukemia virus (GALV). The foreign enhancer and promoter may be the human cytomegalovirus (HCMV) immediate early (IE) enhancer and promoter, the enhancer and promoter (U3 region) of the Moloney Murine Sarcoma Virus (MMSV), the U3 region of Rous Sarcoma Virus (RSV), the U3 region of Spleen Focus Forming Virus (SFFV), or the HCMV IE enhancer joined to the native Moloney Murine Leukemia Virus (MMLV) promoter. The retroviral packaging plasmid may consist of two retroviral helper DNA sequences encoded by plasmid based expression vectors, for example where a first helper sequence contains a cDNA encoding the gag and pol proteins of ecotropic MMLV or GALV and a second helper sequence contains a cDNA encoding the env protein. The Env gene, which determines the host range, may be derived from the genes encoding xenotropic, amphotropic, ecotropic, polytropic (mink focus forming) or 10A1 murine leukemia virus env proteins, or the Gibbon Ape Leukemia Virus (GALV env protein, the Human Immunodeficiency Virus env (gp160) protein, the Vesicular Stomatitus Virus (VSV) G protein, the Human T cell leukemia (HTLV) type I and II env gene products, chimeric envelope gene derived from combinations of one or more of the aforementioned env genes or chimeric envelope genes encoding the cytoplasmic and transmembrane of the aforementioned env gene products and a monoclonal antibody directed against a specific surface molecule on a desired target cell.

In the packaging process, the packaging plasmids and retroviral vectors expressing the LHR are transiently cotransfected into a first population of mammalian cells that are capable of producing virus, such as human embryonic kidney cells, for example 293 cells (ATCC No. CRL1573, ATCC, Rockville, Md.) to produce high titer recombinant retrovirus-containing supernatants. In another method of the invention this transiently transfected first population of cells is then cocultivated with mammalian target cells, for example human lymphocytes, to transduce the target cells with the foreign gene at high efficiencies. In yet another method of the invention the supernatants from the above described transiently transfected first population of cells are incubated with mammalian target cells, for example human lymphocytes or hematopoietic stem cells, to transduce the target cells with the foreign gene at high efficiencies.

In another aspect, the packaging plasmids are stably expressed in a first population of mammalian cells that are capable of producing virus, such as human embryonic kidney cells, for example 293 cells. Retroviral or lentiviral vectors are introduced into cells by either cotransfection with a selectable marker or infection with pseudotyped virus. In both cases, the vectors integrate. Alternatively, vectors can be introduced in an episomally maintained plasmid. High titer recombinant retrovirus-containing supernatants are produced.

Activation and Expansion of T Cells. Whether prior to or after genetic modification of the T cells to express a desirable CAR, the T cells can be activated and expanded generally using generally known methods such as those described in U.S. Pat. Nos. 6,352,694; 6,534,055; 6,905, 680; 6,692,964; 5,858,358; 6,887,466; 6,905,681; 7,144, 575; 7,067,318; 7,172,869; 7,232,566; 7,175,843; 5,883, 223; 6,905,874; 6,797,514; 6,867,041. Stimulation with the B7-4 antigen ex vivo can activate and expand the selected CAR expressing T-cell subpopulation. Alternatively, the T-cells may be activated in vivo by interaction with LHR antigen.

Methods of activating relevant cells are well known in the art and can be readily adapted to the present application; an exemplary method is described in the examples below. Isolation methods for use in relation to this disclosure include, but are not limited to Life Technologies Dynabeads® system activation and expansion kits; BD Biosciences Phosflow™ activation kits, Miltenyi Biotec MACS™ activation/expansion kits, and other commercially available cell kits specific to activation moieties of the relevant cell. Particular subpopulations of immune cells may be activated or expanded through the use of beads or other agents available in such kits. For example, α-CD³/α-CD28 Dynabeads® may be used to activate and expand a population of isolated T-cells As disclosed above, chimeric antigen receptors comprise an antigen recognition moiety and a cell activation moiety. Aspects of the present disclosure related to a chimeric antigen receptor (CAR) comprising an antigen binding domain specific to LHR.

In one embodiment, the CAR of the present disclosure is characterized in that it comprises, or alternatively consists essentially of, or yet further consists an antigen binding domain of an anti-luteinizing hormone receptor ("LHR") antibody, a CD8 α hinge domain; a CD8 α transmembrane domain; a CD28 and/or a 4-1BB costimulatory signaling region; and a CD3 zeta signaling domain.

In another embodiment, the antigen binding domain of the anti-LHR antibody comprises an anti-LHR heavy chain variable region and an anti-LHR light chain variable region. As apparent to the skilled artisan, antibodies having the detailed elements are also within the scope of this disclosure.

In one aspect, the heavy chain variable region comprises, or alternatively consists essentially of, or yet further consists of an heavy chain amino acid sequence from any LHR antibody subclones of 5F4-21, 4A7-4, 138-2, and 8B7-3, and the light chain variable region comprises, or alternatively consists essentially of, or yet further consists of the light chain amino acid sequence from any LHR antibody subclones of 5F4-21, 4A7-4, 138-2, and 8B7-3, or equivalents thereof, as follows:

```
LHR Antibody #5F4-21 Heavy Chain Amino Acid
Sequence,
                                   SEQ ID NO.: 1
EVQLQESGPDLVKPSQSLSLTCTVTGYSITSGYGWHWIRQFPGNKLEWMG

YIHYSGSTTYNPSLKSRISISRDTSKNQFFLQLNSVTTEDTATYYCARSL

RYWGQGTTLTVSS

LHR Antibody #4A7-4 Heavy Chain Amino Acid
Sequence,
                                   SEQ ID NO.: 2
QVQLKESGPGLVAPSQSLSITCTVSGFSLTTYGVSWVRQPPGKGLEWLGV

IWGDGSTYYHSALISRLSISKDNSKSQVFLKLNSLQTDDTATYYCAEGSS

LFAYWGQGTLVTVSA

LHR Antibody #138-2 Heavy Chain Amino Acid
Sequence,
                                   SEQ ID NO.: 3
EVQLEQSGGGLVQPGGSRKLSCAASGFTFSSFGMHWVRQAPEKGLEWVAY

ISSGSSTLHYADTVKGRFTISRDNPKNTLFLQMKLPSLCYGLLGSRNLSH

RLL

LHR Antibody #8B7-3 Heavy Chain Amino Acid
Sequence,
                                   SEQ ID NO.: 4
QVKLQQSGPELVKPGASVKISCKASGYSFTGYYMHWVKQSHGNILDWIGY

IYPYNGVSSYNQKFKGKATLTVDKSSSTAYMELRSLTSEDSAVYYCARER

GLYQLRAMDYWGQGTSVTVSS

LHR Antibody #5F4-21 Light Chain Amino Acid
Sequence,
                                   SEQ ID NO : 5
DIVMTQTPAIMSASPGQKVTITCSASSSVNYMHWYQQKLGSSPKLWIYDT

SKLAPGVPARFSGSGSGTSYSLTISSMEAEDAASYFCHQWSSYPYTFGSG

TKLEIK

LHR Antibody #4A7-4 Light Chain Amino Acid
Sequence,
                                   SEQ ID NO: 6
DIVMTQSPSSLTVTAGEKVTMSCKSSQSLLNSGNQKNYLTWYQQKPGQPP

KLLIYWASTRQSGVPDRFTGSGSGTDFTLTISSVQAEDXAVYYCQNDYSY

PLTFGSGTKLEIK

LHR Antibody #138-2 Light Chain Amino Acid
Sequence,
                                   SEQ ID NO. 7
DIVLTQTPSSLSASLGDTITITCHASQNINVWLFWYQQKPGNIPKLLIYK

ASNLLTGVPSRFSGSGSGTGFTLTISSLQPEDIATYYCQQGQSFPWTFGG

GTKLEIK

LHR Antibody #8B7-3 Light Chain Amino Acid
Sequence,
                                   SEQ ID NO: 8
DIVLTQTPATLSVTPGDSVSLSCRASQSISNNLHWYQQKSHESPRLLIKN

ASQSISGIPSKFSGSGSGTDFTLRINSVETEDFGMYFCQQSNSWPYTFGS

GTKLEIK
```

In another aspect, the heavy chain and light chain amino acid sequences of antibody subclones of 5F4-21, 4A7-4, 138-2, and 8B7-3 are aligned with ClustalW2 (http://www.ebi.ac.uk/Tools/msa/clustalw2/) to determine the consensus sequences for heavy chain and light chain by using Boxshade (http://www.ch.embnet.org.software/BOX_form-.html). The alignment and consensus sequence analysis results are shown in FIG. 7. Accordingly the heavy chain variable region comprises, or alternatively consists essentially of, or yet further consists of a polypeptide with a consensus sequence selected from SEQ NOs: 9-11, and an anti-LHR light chain variable region comprises, or alternatively consists essentially of, or yet further consists of a polypeptide with a consensus sequence selected from SEQ NOs.:12-15 (or an equivalent thereof) as follows:

```
                                   SEQ ID NO: 9
            ISISRDNSK

SEQ ID NO: 10
            VFLQLNSLTTEDTATYYCARGS

SEQ ID NO: 11
            LRYWGQGTLVTV

SEQ ID NO: 12
            SPGDKVTITCHASQSINN

SEQ ID NO: 13
            YLHWYQQKPGNSPKILLY

SEQ ID NO: 14
            LSGVPSRFSGSGSGTDFTLTISSV
```

QSYPYTFGSGTKLEIK

SEQ ID NO: 15

In one aspect, the heavy chain variable region comprises or alternatively consists essentially of, or yet further consists of a CDR1 comprising the amino acid sequence of GYSITSGYG (SEQ ID NO.: 16) or an equivalent of each thereof; and/or a CDR2 comprising the amino acid sequence of IHYSGST (SEQ ID NO.: 19) or an equivalent of each thereof; and/or a CDR3 comprising the amino acid sequence of ARSLRY (SEQ ID NO.: 22) or an equivalent of each thereof; and/or the light chain variable region comprises or alternatively consists essentially of, or yet further consists of a CDR1 comprising the amino acid sequence of SSVNY (SEQ ID NO.:25) or an equivalent of each thereof; and/or a CDR2 comprising the amino acid sequence of DTS (SEQ ID NO:28) or an equivalent of each thereof; and/or a CDR3 comprising the amino acid sequence of HQWSSYPYT (SEQ ID NO:31) or an equivalent of each thereof. Additional amino acids, as disclosed herein, can be added to the carboxy terminus.

In another aspect, the heavy chain variable region comprises, or alternatively consists essentially of, or yet further consists of a CDR1 comprising the amino acid sequence of GFSLTTYG (SEQ ID NO: 17) or an equivalent of each thereof; and/or a CDR2 comprising the amino acid sequence of IWGDGST (SEQ ID NO.: 20) or an equivalent of each thereof; and/or a CDR3 comprising the amino acid sequence of AEGSSLFAY (SEQ ID NO.: 23) or an equivalent of each thereof; and/or the light chain variable region comprises, or alternatively consists essentially of, or yet further consists of a CDR1 comprising the amino acid sequence of QSLLNSGNQKNY (SEQ ID NO.:26) or an equivalent of each thereof; and/or a CDR2 comprising the amino acid sequence of WAS (SEQ ID NO:29) or an equivalent of each thereof; and/or a CDR3 comprising the amino acid sequence of QNDYSYPLT (SEQ ID NO:32) or an equivalent of each thereof. Additional amino acids, as disclosed herein, can be added to the carboxy terminus.

In another aspect, the heavy chain variable region comprises, or alternatively consists essentially of, or yet further consists of a CDR1 comprising the amino acid sequence of GYSFTGYY (SEQ ID NO.: 18) or an equivalent of each thereof; and/or a CDR2 comprising the amino acid sequence of IYPYNGVS (SEQ ID NO.: 21) or an equivalent of each thereof; and/or a CDR3 comprising the amino acid sequence of ARERGLYQLRAMDY (SEQ ID NO.: 24) or an equivalent of each thereof; and/or the light chain variable region comprises, or alternatively consists essentially of, or yet further consists of a CDR1 comprising the amino acid sequence of QSISNN (SEQ ID NO.:27) or an equivalent of each thereof; and/or a CDR2 comprising the amino acid sequence of NAS (SEQ ID NO:30) or an equivalent of each thereof; and/or a CDR3 comprising the amino acid sequence of QQSNSWPYT (SEQ ID NO:33) or an equivalent of each thereof. Additional amino acids, as disclosed herein, can be added to the carboxy terminus.

In another embodiment, the CAR comprises, or alternatively consists essentially of, or yet further consists of a linker polypeptide located between the anti-LHR heavy chain variable region and the anti-LHR light chain variable region.

In some aspects of the disclosure, the LHR CAR further comprises, or alternatively consists essentially of, or yet further consists of a detectable marker or a purification marker.

In some embodiment, the LHR CAR, further comprises, or alternatively consists essentially of, or yet further consists of antigen binding domain derived from an antibody against MUC-16 or mesothelin.

In one embodiment, the disclosure provides an isolated nucleic acid sequence comprising, or alternatively consisting essentially of, or yet further consisting of a nucleic acid sequence, or an equivalent thereof, of one or more than one of a polynucleotide selected from LHR antibody #5F4-21 heavy chain DNA sequence, LHR antibody #5F4-21 light chain DNA sequence, LHR antibody #4A7-4 heavy chain DNA sequence, LHR antibody #4A7-4 light chain DNA sequence, LHR antibody #138-2 heavy chain DNA sequence, LHR antibody #138-2 light chain DNA sequence, LHR antibody #8B7-3 heavy chain DNA sequence, LHR Antibody #8B7-3 light chain DNA sequence as follow:

LHR Antibody #5F4-21 Heavy Chain DNA Sequence,
SEQ ID NO: 34
GAAGTGCAGCTGCAGGAGTCAGGACCTGACCTGGTGAAACCTTCTCAGTC

ACTTTCACTCACCTGCACTGTCACCGGCTACTCCATCACCAGTGGTTATG

GCTGGCACTGGATCCGGCAGTTTCCAGGAAACAAACTGGAGTGGATGGGC

TACATACACTACAGTGGTAGCACTACCTACAACCCATCTCTCAAAAGTCG

AATCTCTATCTCTCGAGACACATCCAAGAATCAGTTCTTCCTGCAGTTGA

ATTCTGTGACTACTGAGGACACAGCCACATATTACTGTGCAAGATCCTTA

CGCTACTGGGGCCAAGGCACCACTCTCACAGTCTCCTCA

LHR Antibody #5F4-21 Light Chain DNA Sequence,
SEQ ID NO: 35
GATATTGTGATGACACAGACTCCAGCAATCATGTCTGCATCTCCAGGGCA

GAAAGTCACCATAACCTGCAGTGCCAGTTCAAGTGTAAATTACATGCACT

GGTACCAGCAGAAGCTAGGATCCTCCCCCAAACTCTGGATTTATGACACA

TCCAAACTGGCTCCTGGAGTCCCTGCTCGCTTCAGTGGCAGTGGGTCTGG

GACCTCTTACTCTCTCACAATCAGCAGCATGGAGGCTGAAGATGCTGCCT

CTTATTTCTGCCATCAGTGGAGTAGTTACCCATATACGTTCGGATCGGGG

ACCAAGCTGGAAATAAAA

LHR Antibody #4A7-4 Heavy Chain DNA Sequence,
SEQ ID NO. 36
CAGGTGCAGCTGAAGGAGTCAGGACCTGGCCTGGTGGCGCCCTCACAGAG

CCTGTCCATCACATGCACTGTCTCAGGGTTCTCATTAACCACCTATGGTG

TAAGCTGGGTTCGCCAGCCTCCAGGAAAGGGTCTGGAGTGGCTGGGAGTA

ATATGGGGTGACGGGAGCACATATTATCATTCAGCTCTCATATCCAGACT

GAGCATCAGCAAGGATAACTCCAAGAGCCAAGTTTTCTTAAAACTGAACA

GTCTGCAAACTGATGACACAGCCACTTACTACTGTGCGGAAGGTAGTAGC

CTCTTTGCTTACTGGGGCCAAGGGACTCTGGTCACTGTCTCTGCG

LHR Antibody #4A7-4 Light Chain DNA Sequence,
SEQ ID NO: 37
GACATTGTGATGACACAGTCTCCATCCTCCCTGACTGTGACAGCAGGAGA

GAAGGTCACTATGAGCTGCAAGTCCAGTCAGAGTCTGTTAAACAGTGGAA

ATCAAAAGAACTACTTGACCTGGTACCAACAGAAACCAGGGCAGCCTCCT

AAACTGTTGATCTACTGGGCATCCACTAGGCAATCTGGGGTCCCTGATCG

CTTCACAGGCAGTGGATCTGGAACAGACTTCACTCTCACCATCAGCAGTG

-continued
TGCAGGCTGAAGACCNGGCAGTTTATTACTGTCAGAATGATTATAGTTAT

CCTCTCACGTTCGGATCGGGGACCAAGCTGGAAATAAAA

LHR Antibody #138-2 Heavy Chain DNA Sequence,
SEQ ID NO: 38
GAGGTGCAGCTGGAGCAGTCTGGGGGAGGCTTAGTGCAGCCTGGAGGGTC

CCGGAAACTCTCCTGTGCAGCCTCTGGATTCACTTTCAGTAGCTTTGGAA

TGCACTGGGTTCGTCAGGCTCCAGAGAAGGGGCTGGAGTGGGTCGCATAC

ATTAGTAGTGGCAGTAGTACCCTCCACTATGCAGACACAGTGAAGGGCCG

ATTCACCATCTCCAGAGACAATCCCAAGAACACCCTGTTCCTGCAAATGA

AACTACCCTCACTATGCTATGGACTACTGGGGTCAAGGAACCTCAGTCAC

CGTCTCCTC

LHR Antibody #138-2 Light Chain DNA Sequence,
SEQ ID NO: 39
GACATTGTGCTGACACAGACTCCATCCAGTCTGTCTGCATCCCTTGGAGA

CACAATTACCATCACTTGCCATGCCAGTCAGAACATTAATGTTTGGTTAT

TCTGGTACCAGCAGAAACCAGGAAATATTCCTAAACTTTTGATCTATAAG

GCTTCCAATTTGCTCACAGGCGTCCCATCAAGGTTTAGTGGCAGTGGATC

TGGAACAGGTTTCACATTAACCATCAGCAGCCTGCAGCCTGAAGACATTG

CCACTTACTACTGTCAACAGGGTCAAAGTTTTCCGTGGACGTTCGGTGGA

GGCACCAAGCTGGAAATCAAA

LHR Antibody #8B7-3 Heavy Chain DNA Sequence,
SEQ ID NO. 40
CAGGTTAAGCTGCAGCAGTCTGGACCTGAGCTGGTGAAGCCTGGGGCTTC

AGTGAAGATATCCTGCAAGGCTTCTGGTTACTCATTCACTGGCTACTACA

TGCACTGGGTGAAGCAGAGCCATGGAAATATCCTCGATTGGATTGGATAT

ATTTATCCTTACAATGGTGTTTCTAGCTACAACCAGAAATTCAAGGGCAA

GGCCACATTGACTGTAGACAAGTCCTCTAGCACAGCCTACATGGAGCTCC

GCAGCCTGACATCTGAGGACTCTGCAGTCTATTACTGTGCAAGAGAGAGG

GGATTATATCAACTACGGGCTATGGACTACTGGGGTCAAGGAACCTCAGT

CACCGTCTCCTCA

LHR Antibody #8B7-3 Light Chain DNA Sequence,
SEQ ID NO: 41
GACATTGTGCTGACACAGACTCCAGCCACCCTGTCTGTGACTCCAGGAGA

TAGCGTCAGTCTTTCCTGCAGGGCCAGCCAAAGTATTAGCAACAACCTAC

ACTGGTATCAACAAAAATCACATGAGTCTCCAAGGCTTCTCATCAAGAAT

GCTTCCCAGTCCATCTCTGGGATCCCCTCCAAGTTCAGTGGCAGTGGATC

AGGGACAGATTTCACTCTCAGAATCAACAGTGTGGAGACTGAAGATTTTG

GAATGTATTTCTGTCAACAGAGTAACAGCTGGCCGTATACGTTCGGATCG

GGGACCAAGCTGGAAATAAAA

In some embodiments, the isolated nucleic acid further comprises, or alternatively consists essentially of, or yet further consists of a Kozak consenus sequence located upstream of the antigen binding domain of the anti-LHR antibody.

In some aspect of the disclosure, the isolated nucleic sequence further comprises, or alternatively consists essentially of, or yet further consists of polynucleotide encoding an antibiotic resistance marker.

In another embodiment, the disclosure provides a vector comprising, or alternatively consisting essentially of, or yet further consisting of the isolated nucleic acid sequence encoding the anti-LHR CAR polypeptide as disclosed above or a complement thereof. In a further aspect, the polynucleotide can be incorporated into a vector. Non-limiting examples of such include a retroviral vector, a plasmid, a lentiviral vector, an adenoviral vector, and an adeno-associated viral vector.

In one embodiment, the disclosure is an isolated cell comprising, or alternatively consisting essentially of, or yet further consisting of an exogenously added polynucleotide encoding the anti-LHR CAR as described above alone or in combination with a vector as described above; and/or the exogenously added the anti-LHR CAR; as describe above.

In one aspect of the disclosure, the isolated cell can be a T-cell or a natural killer (NK) cell.

III. Methods of Use

Therapeutic Application. The CAR T-cells of the present invention may be used to treat tumors and cancers. The CAR-T cells of the present invention may be administered either alone or in combination with diluents, known anti-cancer therapeutics, and/or with other components such as cytokines or other cell populations that are immunostimulatory.

Method aspects of the present disclosure relate to methods for inhibiting the growth of a tumor in a subject in need thereof and/or for treating a cancer patient in need thereof. In some embodiments, the tumor is a solid tumor. In some embodiments, the tumors/cancer is thyroid, breast, ovarian or prostate tumors/cancer. In some embodiments, the tumor or cancer expresses or overexpresses LHR. In certain embodiments, these methods comprise, or alternatively consist essentially of, or yet further consist of, administering to the subject or patient an effective amount of the isolated cell. In further embodiments, this isolated cell comprises a LHR CAR. In still further embodiments, the isolated cell is a T-cell or an NK cell. In some embodiments, the isolated cell is autologous to the subject or patient being treated. In a further aspect, the tumor expresses LHR antigen and the subject has been selected for the therapy by a diagnostic, such as the one described herein.

The CAR cells as disclosed herein may be administered either alone or in combination with diluents, known anti-cancer therapeutics, and/or with other components such as cytokines or other cell populations that are immunostimulatory. They may be first line, second line, third line, fourth line, or further therapy. The can be combined with other therapies. Non-limiting examples of such include chemotherapies or biologics. Appropriate treatment regimes will be determined by the treating physician or veterinarian.

Pharmaceutical compositions comprising the LHR CAR of the present invention may be administered in a manner appropriate to the disease to be treated or prevented. The quantity and frequency of administration will be determined by such factors as the condition of the patient, and the type and severity of the patient's disease, although appropriate dosages may be determined by clinical trials.

In another aspect, the disclosure provides a method of inhibiting the growth of a solid tumor in a subject in need thereof, comprising administering to the subject an effective amount of the isolated cell of anti-LHR CAR T-cell. In one embodiment, the isolated T-cells are autologous to the subject being treated. In another embodiment, the tumor is ovarian tumor or a prostate cancer tumor. The method of inhibiting the growth of a tumor can be applied to a subject including but not limited to human, dog, cat, horse, and other species.

In another aspect, the disclosure provides a method of treating a cancer patient in need thereof, comprising, or alternatively consisting essentially of, or yet further consisting of administering to the subject an effective amount of the isolated cell of anti-LHR T-cell. The isolated T-cells can be autologous to the subject being treated. The tumor is ovarian cancer or a prostate cancer. In one embodiment, the subject treated for cancer is a human patient.

In one embodiment, the disclosure provides a method for determining if a patient is likely to respond or is not likely to anti-LHR CAR therapy, comprising, or alternatively consisting essentially of, or yet further consisting of contacting a tumor sample isolated from the patient with an effective amount of an anti-LHR antibody and detecting the presence of any antibody bound to the tumor sample, wherein the presence of antibody bound to the tumor sample indicates that the patient is likely to respond to the anti-LHR CAR therapy and the absence of antibody bound to the tumor sample indicates that the patient is not likely to respond to the anti-CAR therapy. In another embodiment, the method further comprises administering an effective amount of the anti-LHR CAR therapy to the patient that is determined likely to respond to the anti-LHR CAR therapy. In this method, the patient can suffer from ovarian cancer or prostate cancer.

The present disclosure also provides diagnostic methods for determining the expression level of LHR. In one particular aspect, the present disclosure provides kits for performing these methods as well as instructions for carrying out the methods of the present disclosure such as collecting tissue and/or performing the screen, and/or analyzing the results.

In one embodiment, the disclosure provides a method of detecting LHR in a biological sample comprising, or alternatively consisting essentially of, or yet further consisting of contacting the sample with an anti-LHR antibody or an antigen binding fragment capable of binding a peptide comprising SEQ ID NOs: 42 and 43, and detecting a complex formed by the binding of the antibody or antigen binding fragment to LHR.

In one aspect, the sample comprises a cell sample or a tissue sample.

In one aspect, the sample is obtained from a subject that is diagnosed as having, suspected as having, or at risk of having cancer.

In another aspect, the cancer is prostate cancer or ovarian cancer. In a further aspect, the cancer cell or tumor cell expresses or overexpresses LHR.

In one aspect, the detection comprises, or alternatively consists essentially of, or yet further consists of one or more of immunohistochemistry (IHC), Western blotting, Flow cytometry or ELISA.

In one aspect, the method comprises, or alternatively consists essentially of, or yet further consists of isolating the biological sample from the subject.

In one aspect, the subject is a mammal.

In another aspect, the mammal is selected from the group of: a human, an animal, a non-human primate, a dog, cat, a sheep, a mouse, a horse, or a cow.

In one embodiment, the disclosure provides a method of detecting a pathological cell in a sample isolated from a subject, comprising, or alternatively consisting essentially of, or yet further consisting of (a) detecting the level of LHR in a biological sample from the subject by detecting a complex formed by an anti-LHR antibody or an antigen binding fragment capable of binding a peptide comprising SEQ ID NOs: 42 and 43; and (b) comparing the levels of LHR observed in step (a) with the levels of LHR observed in a control biological sample; wherein the pathological cell is detected when the level of LHR is elevated compared to that observed in the control biological sample.

In one aspect, the biological sample of the subject comprises, or alternatively consists essentially of, or yet further consists of one or more of a sample isolated from prostate and ovary.

In another aspect, the detection comprises, or alternatively consists essentially of, or yet further consists of one or more of immunohistochemistry (IHC), Western Blotting, Flow cytometry or ELISA.

In one aspect, the method comprises, or alternatively consists essentially of, or yet further consists of isolating the biological sample from the subject.

In one aspect, the subject is a mammal.

In another aspect, the mammal is selected from the group of: a human, an animal, a non-human primate, a dog, cat, a sheep, a mouse, a horse, or a cow.

I. Carriers

Additional aspects of the invention relate to compositions comprising a carrier and one or more of the products—e.g., an isolated cell comprising a HLA-G CAR, an isolated nucleic acid, a vector, an isolated cell of any anti-HLA-G antibody or CAR cell, an anti-HLA-G—described in the embodiments disclosed herein.

Briefly, pharmaceutical compositions of the present invention including but not limited to any one of the claimed compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for oral, intravenous, topical, enteral, and/or parenteral administration. In certain embodiments, the compositions of the present disclosure are formulated for intravenous administration.

Briefly, pharmaceutical compositions of the present invention including but not limited to any one of the claimed compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine;antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated or prevented. The quantity and frequency of administration will be determined by such factors as the condition of the patient, and the type and severity of the patient's disease, although appropriate dosages may be determined by clinical trials.

The following examples are provided to illustrate, and not limit the disclosure.

EXAMPLES

Example 1

Generation of Mouse Anti-LHR Monoclonal Antibodies

Figure 3:
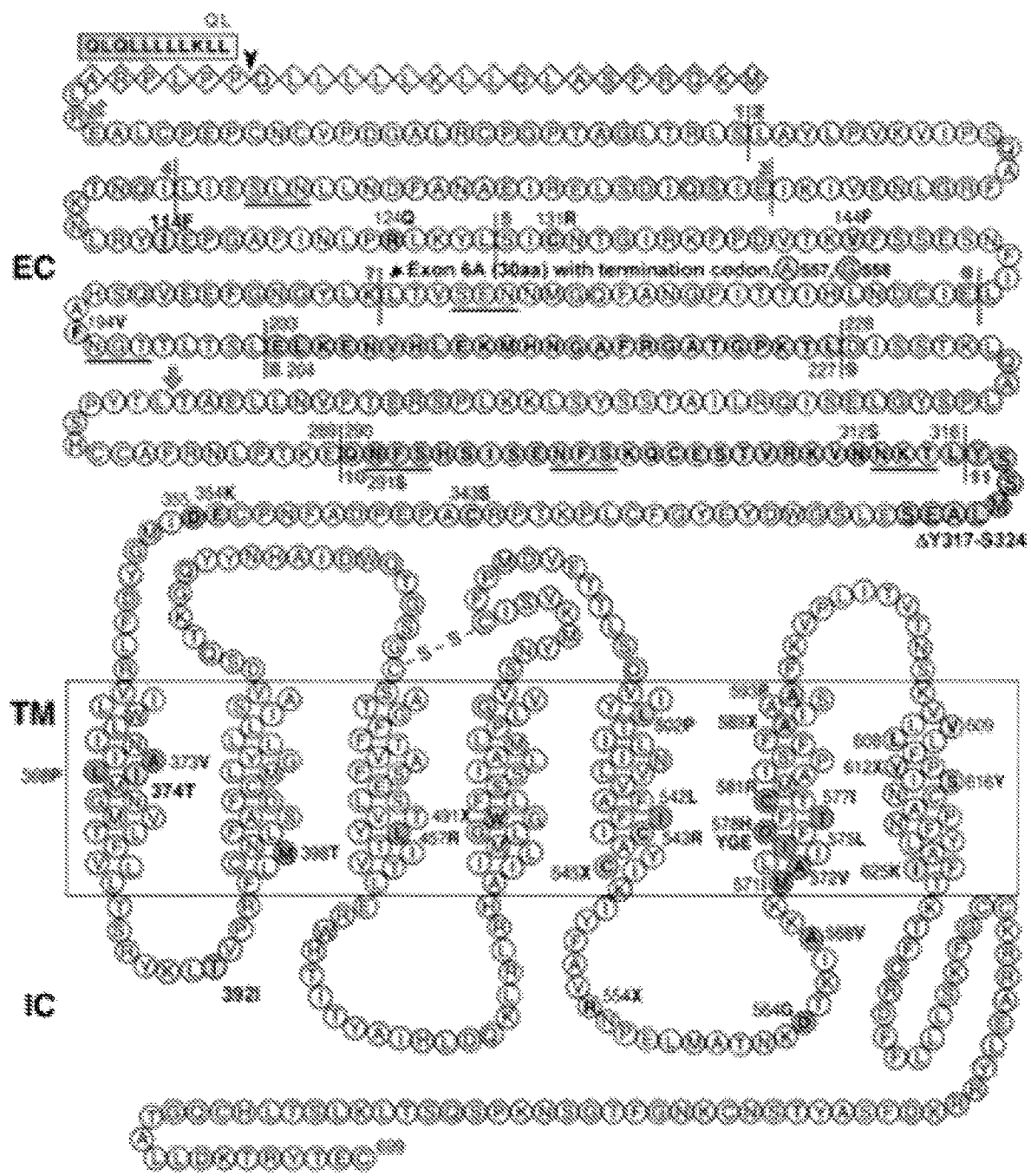
FIG. 3 shows the sequence used to generate LHR-Fc Amino acid structure of LHR G-protein showing sequence (outlined area) used to generate a LHR-Fc used in immunization and screening methods to identify potential LHR binding antibodies useful for the generation of LHR CARS.
Figure 4:
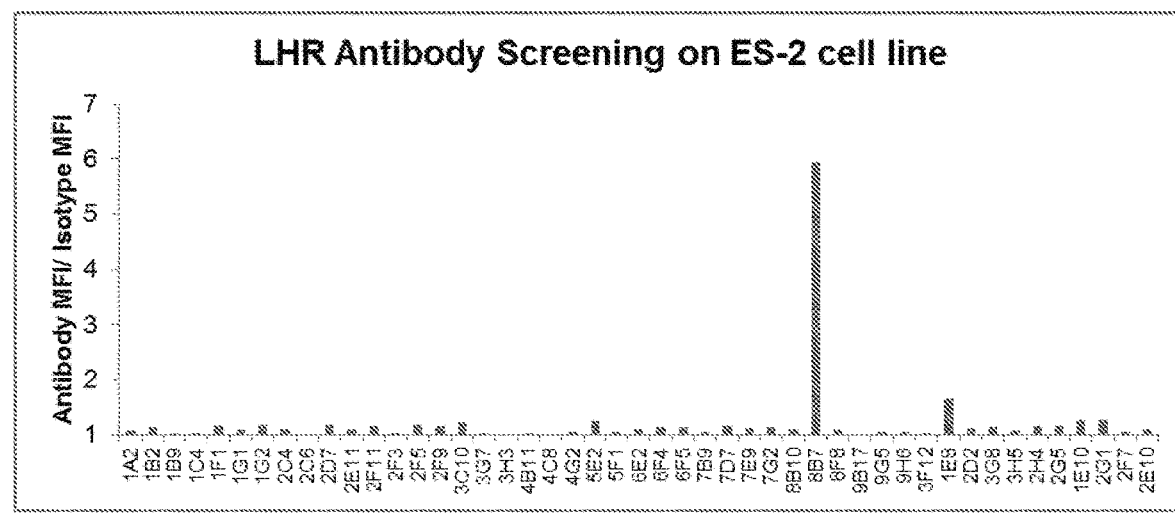
FIG. 4 shows typical flow cytometry screen of LHR-Fc ELISA positive antibodies on the ES-2 ovarian carcinoma cell line demonstrating strong reactivity by hybridoma 8B7 only.
Figure 5:
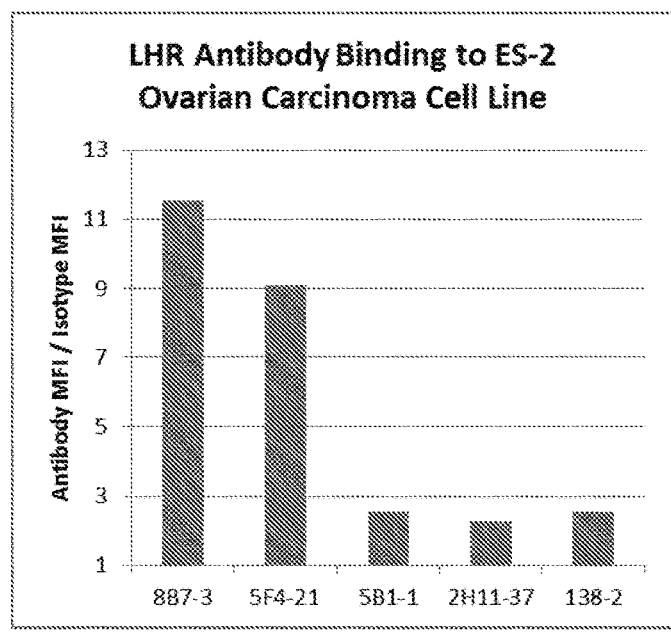
FIG. 5 shows flow cytometry of 5 candidate LHR antibody subclones with highest MFI values on ES-2 human ovarian carcinoma cells.

Antibodies against the lysine rich extracellular hormone binding domain of LHR were generated by repeated immunization of 4 week-old-BALB/c and NIH Swiss mice with genetically engineered LHR-Fc. As shown below in FIG. 3, the leader sequence and first part of the human LHR G-protein was used to generate the LHR-Fc used in the immunization and screening methods to generate and identify high binding antibodies. Since flow cytometry has previously been shown to be the best predictor of functional antibodies for CAR generation, this method was used to identify potential candidate antibodies from over 7 fusions performed in the laboratory. A typical flow cytometry screen of hybridomas positive by initial ELISA screen using LHR-Fc coated plates is shown below in FIG. 4 using the ES-2 ovarian carcinoma cell line. As seen in this figure with hybridoma 8B7, only rare LHR hybridomas were shown to produce high MFI by flow cytometry. These few candidate hybridomas were then subcloned by dilution in 96 well plates and expanded for freezing in vials. After further screening by flow cytometry, specific subclones were selected for large scale production using 2L vessels (GRrex, 100L, Wolfson). Filtered supernatants were then subjected to antibody purification using tandon protein A or G and ion exchange chromatography methods performed routinely in the laboratory. Once purified, five antibody subclones designated 8B7-3, 5F4-21, 5B1-1, 2H11-37, and 138-2 were sequenced to facilitate the engineering of single chain genes used for the construction of LHR CARs described below. For comparison, the 5 selected hybridoma subclones were tested on the ES-2 human ovarian carcinoma cell line by flow cytometry to demonstrated their relative mean fluorescence intensity (MFI) (FIG. 5).

Example 2

Anti-LHR Monoclonal Antibodies Detecting the Expression of LHR in Ovarian Cancer The overall hypothesis is that ovarian cancer can be treated effectively and safely with LHR chimeric antigen receptor modified T-cells. As a target, LHR has significant advantages over other targets due to its common expression on ovarian cancers and its lack of expression on normal human tissues. LHR CAR T-cells are produced in vitro and in vivo to identify a potential clinical candidate for subsequent clinical trials or use with dual targeting CAR modified T-cells.

Construction and Synthesis Single Chain LHR Antibody Genes

Figure 6:
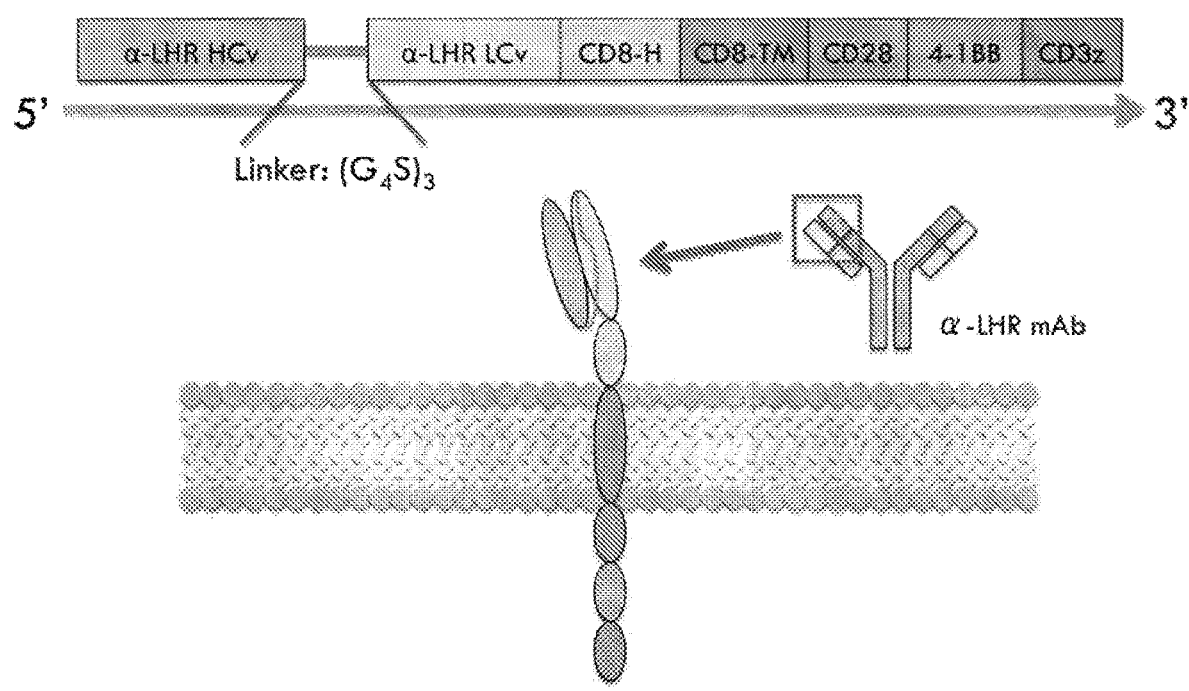
FIG. 6 shows a schematic diagram of the DNA sequence for, and the theoretical structure of an anti-LHR CAR in the plasma membrane.
Figure 8A:
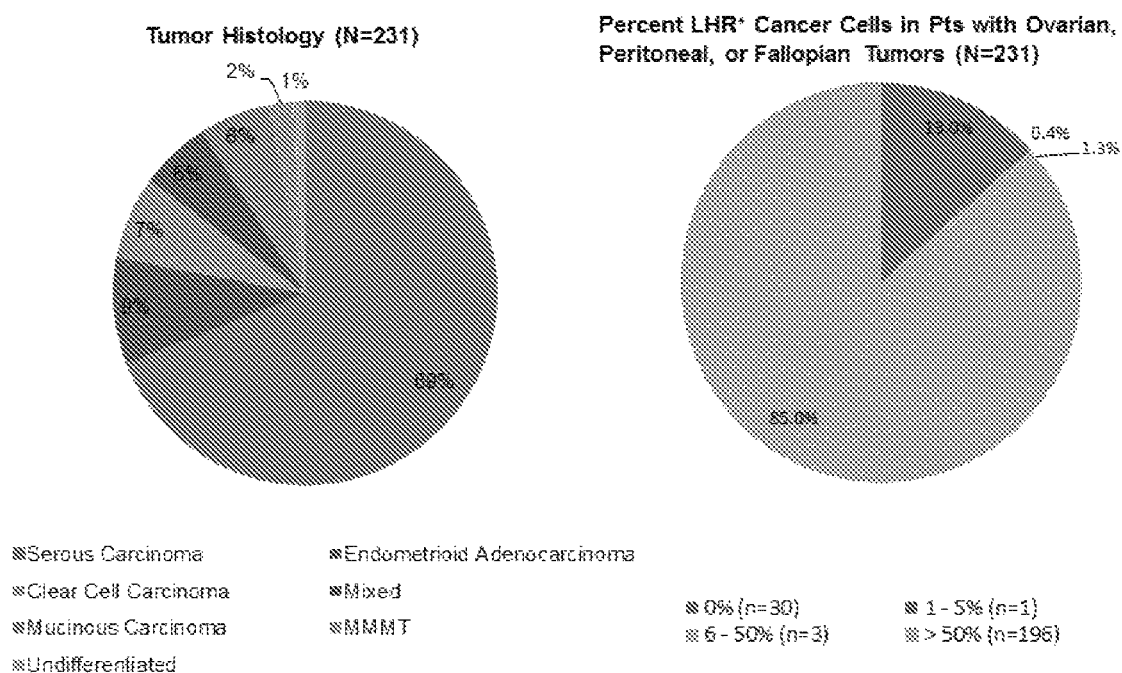
Figure 8B:
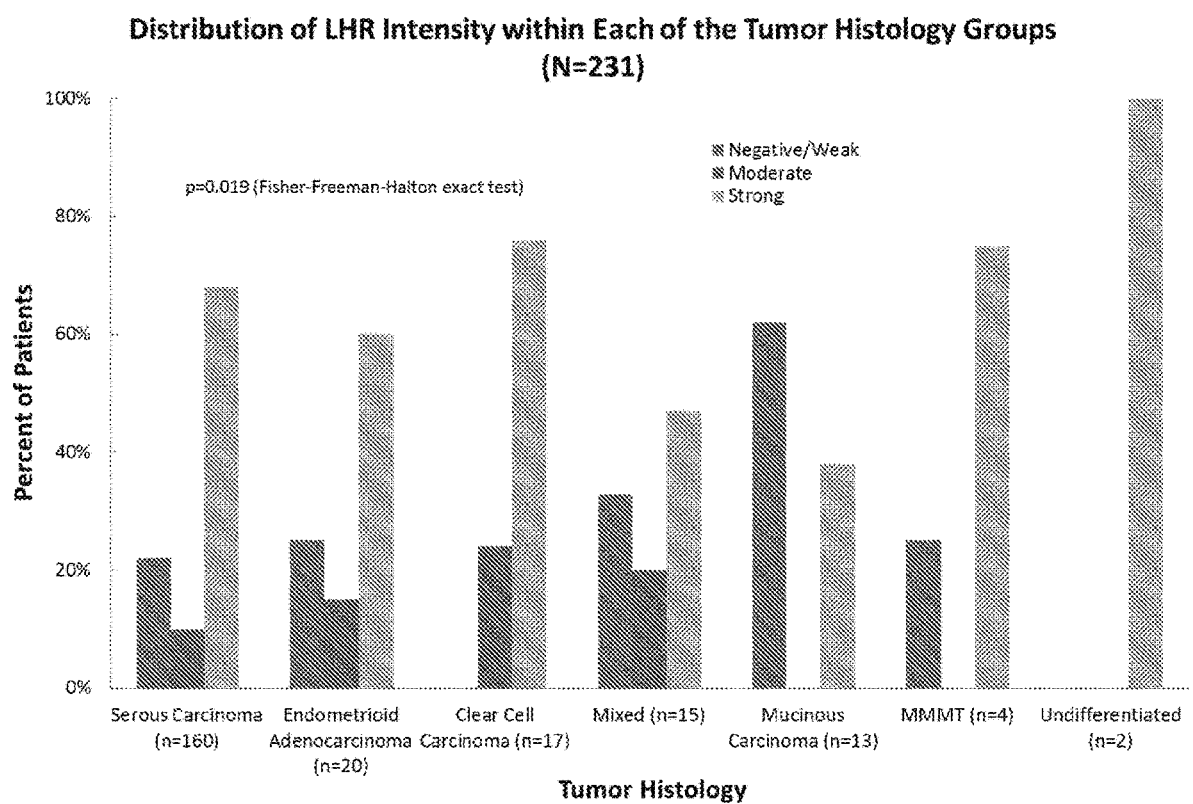

The DNA sequences for the 5 high binding anti-LHR antibodies (8B7-3, 5F4-21, 5B1-1, 2H11-37, and 138-2) were sequenced by MCLAB (South San Francisco, Calif.). All five antibodies are tested to determine which one produces the most effective CAR in assays described below. As shown below in FIG. 6, third generation CAR vectors were constructed consisting of the following tandem genes: a kozak consensus sequence; the CD8 signal peptide; the anti-LHR heavy chain variable region; a (Glycine4Serine)$_3$ flexible polypeptide linker; the respective anti-LHR light chain variable region; CD8 hinge and transmembrane domains; and the CD28, 4-1BB, and CD3ζ intracellular co-stimulatory signaling domains. Hinge, transmembrane, and signaling domain DNA sequences were known in the art (see US Patent Application No. 20130287748 A1). Anti-LHR CAR genes can be synthesized within a pUC57 vector backbone containing a beta-lactamase ("bla") gene, which confers ampicillin resistance to the vector host. The pUC57 vector sequence is disclosed herein by referring to GeneBank accession No. Y14837 with the sequence of the beta-lactamase gene disclosed in the listed GeneBank accession No. The sequence associated with the listed GeneBank Accession number is herein incorporated by reference.

Subcloning of CAR Genes into Lentiviral Plasmids

NovaBlue Singles™ chemically-competent E. coli cells were transformed with anti-LHR plasmid cDNA. Following growth of the transformed E. coli cells, the CAR plasmids were purified and digested with the appropriate restriction enzymes inserted into an HIV-1-based lentiviral vector containing HIV-1 long terminal repeats (LTRs), packaging signal (Ψ), EF1α promoter, internal ribosome entry site (IRES), and woodchuck hepatitis virus post-transcriptional regulatory element (WPRE) via overnight T$_4$ DNA ligase reaction (New England Biosciences; Ipswich, Mass.). NovaBlue Singles™ chemically-competent E. coli cells are then transformed with the resulting anti-LHR containing lentiviral plasmid.

Production of Lentiviral Particles

Prior to transfection, HEK293T cells were seeded at $4.0 \times 10^6$ cells/100 mm tissue-culture-treated plate in 10 mL complete-Tet-DMEM and incubated overnight at 37° C. in a humidified 5% CO$_2$ incubator. Once 80-90% confluent, HEK293T cells were co-transfected with CAR-gene lentiviral plasmids and lentiviral packaging plasmids containing genes necessary to form lentiviral envelope and capsid components to facilitate the formation of plasmid-containing nanoparticles that bind HEK293T cells. After incubating transfected-HEK293T cell cultures for 4 hours at 37° C., the transfection medium was replaced with 10 mL fresh complete Tet DMEM. HEK293T cells are then incubated for an additional 48 hours, after which cell supernatants are harvested and tested for lentiviral particles via sandwich ELISA against p24, the main lentiviral capsid protein. Lentivirus-containing supernatants were aliquoted and stored at −80° C. until use for transduction of target CD4$^+$ and CD8$^+$ T cells.

Purification, Activation, and Enrichment of Human CD4$^+$ and CD8$^+$ Peripheral Blood T-Cells Peripheral blood mononuclear cells (PBMCs) enriched by density gradient centrifugation with Ficoll-Paque Plus (GE Healthcare; Little Chalfont, Buckinghamshire, UK) were recovered and washed by centrifugation with PBS containing 0.5% bovine serum albumin (BSA) and 2 mM EDTA. MACS CD4$^+$ and CD8$^+$ MicroBeads (Miltenyi Biotec; San Diego, Calif.) kits can be used to isolate these human T-cell subsets using magnetically activated LS columns to positive select for CD4$^+$ and CD8$^+$ T-cells. Magnetically-bound T-cells were then removed from the magnetic MACS separator, flushed from the LS column, and washed in fresh complete medium. The purity of CD4$^+$ and CD8$^+$ T-cell populations were assessed by flow cytometry using Life Technologies Acoustic Attune® Cytometer, and were enriched by Fluorescence-Activated Cell Sorting performed at USC's flow cytometry core facilities if needed. CD4$^+$ and CD8$^+$ T-cells were maintained at a density of $1.0 \times 10^6$ cells/mL in complete medium supplemented with 100 IU/mL IL-2 in a suitable cell culture vessel, to which α-CD3/α-CD28 Human T-cell Dynabeads (Life Technologies; Carlsbad, Calif.) were added to activate cultured T cells. T-cells were incubated at 37° C. in a 5% $CO_2$ incubator for 2 days prior to transduction with CAR-lentiviral particles.

Lentiviral Transduction of $CD4^+$ $CD8^+$ T-Cells

Activated T-cells are collected and dead cells were removed by Ficoll-Hypaque density gradient centrifugation or the use of MACS Dead Cell Removal Kit (Miltenyi Biotec; San Diego, Calif.). In a 6-well plate, activated. T-cells were plated at a concentration of $1.0 \times 10^6$ cells/mL complete medium. To various wells, LHR CAR-containing lentiviral particles were added to cell suspensions at varying multiplicity of infections (MOIs), such as 1, 5, 10, and 50. Polybrene, a cationic polymer that aids transduction by facilitating interaction between lentiviral particles and the target cell surface, was added at a final concentration of 4 μg/mL. Plates are centrifuged at 800×g for 1 hour at 32° C. Following centrifugation, lentivirus-containing medium was aspirated and cell pellets are re-suspended in fresh complete medium with 100 IU/mL IL-2. Cells were placed in a 5% $CO_2$ humidified incubator at 37° C. overnight. Three days post-transduction, cells were pelleted and re-suspended in fresh complete medium with IL-2 and 400 μg/mL Geneticin (G418 sulfate) (Life Technologies; Carlsbad, Calif.). LHR CAR modified T-cells are assessed by flow cytometry and southern blot analysis to demonstrate successful transduction procedures. Prior to in vitro and in vivo assays, LHR CAR T-cells were enriched by FACS and mixed 1:1 for the in vivo studies.

In Vitro Assessment of CAR Efficacy by Calcein-Release Cytotoxicity Assays

LHR antigen positive and negative target cells were collected, washed, and re-suspended in complete medium at a concentration of $1.0 \times 10^6$ cells/mL. Calcein-acetoxymethyl (AM) was added to target cell samples at 15 which was then incubated at 37° C. in a 5% $CO_2$ humidified incubator for 30 minutes. Dyed positive and negative target cells were washed twice and re-suspended in complete medium by centrifugation and added to a 96-well plate at $1.0 \times 10^4$ cells/well. LHR CAR T-cells was added to the plate in complete medium at effector-to-target cell ratios of 50:1, 5:1, and 1:1. Dyed-target cells suspended in complete medium and complete medium with 2% triton X-100 serves as spontaneous and maximal release controls, respectively. The plates were centrifuged at 365×g and 20° C. for 2 minutes before being placed back in the incubator for 3 hours. The plates were then centrifuged for 10 minutes and cell supernatants were aliquoted to respective wells on a black polystyrene 96-well plate and assessed for fluorescence on a Bio-Tek® Synergy™ HT microplate reader at excitation and emissions of 485/20 nm and 528/20 nm, respectively.

Quantification of Human Cytokines by Luminex Bioassay.

Supernatants of LHR CAR modified T-cells and LHR positive and negative tumor cell lines were measured for cytokine secretion as a measure of CAR T-cell activation using standard procedures known in the art. Data were compared to medium alone and to cultures using unactivated human T-cells to identify background activity. The concentration of IL-2, IFN-g, IL-12, and other pertinent cytokines are measured over time during the incubation process.

In Vivo Assessment of CAR T-Cell Efficacy in Two Xenograft Ovarian Cancer Models LHR CAR T-cells are further evaluated in vivo using two different human ovarian cell xenograft tumor models. In the first model, solid human ovarian tumors are established subcutaneously in nude mice by injection of $5 \times 10^6$ LHR positive ovarian cancer cell lines or LHR negative solid tumor cell lines. When the tumors reach 0.5 cm in diameter, groups of mice (n=5) are treated intravenously with 1 or $3 \times 10^7$ human T-cells as negative controls or LHR CARs constructed from the most active LHR antibodies based upon the in vitro study results. Tumor volumes are then be measured by caliper 3×/week and volume growth curves are generated to demonstrate the effectiveness of experimental treatments over controls. In the second tumor model which is modified from Chekmasova et al. (Chekmasova, A. A. et al. (2010) Clin. Cancer Res. 16:3594-606), groups (n=5) of NOD/SCID/γ-chain −/−6-8 week old female mice (Jackson Laboratories, Inc.) are injected intraperitoneally with $3 \times 10^6$ GFP transfected tumor cells from LHR positive or negative (control) human cell lines. Unlike Chekmasova et al. (Chekmasova, A. A. et al. (2010) Clin. Cancer Res. 16:3594-606) who treated mice 7 days after implantation, however, CAR T-cell therapy is not be initiated until the establishment of ascites at 3 weeks after implantation. At this time, 1 or $3 \times 10^7$ LHR CAR T-cell preparations are injected intraperitoneally and tumor volume is then monitored by fluorescent imaging weekly thereafter. Mice showing tumor progression are sacrificed at the appropriate time to alleviate morbidity. Kaplan Meier plots of mouse survival are generated from the data in order to compare the survival of control and experimental treatment groups. At sacrifice, blood and ascites are analyzed for the presence of CAR T-cells using human specific antibodies and flow cytometry. In addition, cytokine secretion is quantified by Luminex bead assay (Life Technologies, Inc.) for type 1 and 2 cytokines as a measure of CAR T-cell activation.

Studies with Dual Expressing CAR Modified T-Cells

In order to increase the specificity of LHR CAR modified T-cells, dual LHR CAR T-cells with either MUC-CD or mesothelin single chains are prepared. The principal of dual targeting CAR T-cells has successfully been tested in breast cancer using ERB/2 and MUC1 (Wilkie, S. et al. (2012) J. Clin. Immunol. 32:1059-1070), mesothelin and α-folate receptor (Lanitis, E. et al. (2013) Cancer Immunol. Res. 1:45-53), and PSMA and PSCA for the treatment of prostate cancer (Kloss, C. C. et al. (2013) Nat. Biotechnol, 31:71-75). MUC16, a mucin family member is over expressed on most ovarian cancers and is an established surrogate serum marker (CA125) for the progression and detection of ovarian cancers. MUC16 is composed of CA125, a large domain that gets cleaved, and a retained domain (MUC-CD) which contains an extracellular fragment, a transmembrane domain and cytoplasmic tail (Rao, T. D. et al. (2010) Appl. Immunohistochem. Mol. Morphology 18:462-472). MUC16 is also expressed at low levels in the uterus, endometrium, fallopian, tubes, ovaries and serosa of the abdominal and thoracic cavities. CAR modified MUC-CD targeted T cells exhibited efficient MUC-CD specific cytolytic activity against human ovarian cancer cell lines in vitro as well as successful eradication of established peritoneal ovarian tumors in SCID-Beige mice (Chekmasova, A. A. et al. (2010) Clin. Cancer Res. 16:3594-606). Hence, MUC-CD is a viable target for CAR therapy and an excellent choice for dual targeting CAR modified T-cells to reduce the potential on-target off-tumor effects. Both MUC-CD and mesothelin CAR modified T-cells have been shown to be effective, and in combination with LHR, may provide a safer alternative if required for optimal clinical use.

Data and Statistical Analysis Plan

For the in vitro calcein-release assays, the percent of target cells lysed are compared using a one-way ANOVA, followed by an appropriate multiple comparisons test if significance ($p<0.05$) is found in the one-way ANOVA. In order to compare survival between CAR T-cells used in experimental and control groups in the ascites xenograft model, Kaplan Meier plots are constructed and a log rank test used to test for significance ($p<0.05$). For the subcutaneous tumor model, an ANOVA is used to compare tumor volume curves, followed by an appropriate multiple comparison test if significance ($p<0.05$) is found in the ANOVA.

TABLE 1

Expression of Three Potential Cell Surface Targets (LHR, mesothelin, MUC16) on Nine Human Ovarian Cell Lines Using Flow Cytometry.

| Ovarian Cell Line | LHR | Mesothelin | MUC16 |
|---|---|---|---|
| EFO-27 | + | − | − |
| EFO-21 | + | + | + |
| ES-2 | + | − | − |
| HEY | + | + | − |
| SKOV3 | + | + | − |
| TOV21G | + | + | − |
| NIHOVCAR3 | + | − | + |
| CAOV3 | + | − | + |
| SW626 | + | − | − |

TABLE 2

Immunohistochemical expression of LHR, MUC16, and Mesothelin on Panel of Human Ovarian Tumors and Tissue Microarrays.

| Position | Pathology Diagnosis | Grade | Stage | Type | LHR | MUC16 | Mesothelin |
|---|---|---|---|---|---|---|---|
| A1 | Serous papillary adenocarcinoma | 1 | Ic | Malignant | + | + | + |
| A2 | Serous papillary adenocarcinoma | 2 | I | Malignant | + | + | + |
| A3 | Serous papillary adenocarcinoma | 2 | Ib | Malignant | + | − | − |
| A4 | Mucinous adenocarcinoma | 1 | Ia | Malignant | + | − | − |
| A5 | Serous papillary adenocarcinoma with necrosis | 1 | Ic | Malignant | + | + | + |
| A6 | Serous papillary adenocarcinoma | 2 | I | Malignant | + | + | + |
| A7 | Serous papillary adenocarcinoma | 2 | Ib | Malignant | + | − | − |
| A8 | Mucinous adenocarcinoma | 1 | Ia | Malignant | + | − | − |
| B1 | Mucinous adenocarcinoma | 1-2 | Ib | Malignant | + | − | − |
| B2 | Clear cell carcinoma | — | I | Malignant | + | + | − |
| B3 | Clear cell carcinoma | — | Ia | Malignant | + | − | − |
| B4 | Endometrioid adenocarcinoma | 1-2 | Ib | Malignant | + | − | − |
| B5 | Mucinous adenocarcinoma | 1-2 | Ib | Malignant | + | − | − |
| B6 | Clear cell carcinoma | — | I | Malignant | + | + | − |
| B7 | Clear cell carcinoma | — | Ia | Malignant | + | − | − |
| B8 | Endometrioid adenocarcinoma with necrosis | 1-2 | Ib | Malignant | + | − | − |
| C1 | Endometrioid adenocarcinoma | 2 | IIIc | Malignant | + | + | + |
| C2 | Granular cell tumor | — | I | Malignant | − | − | − |
| C3 | Ovary tissue | — | — | Normal | − | − | − |
| C4 | Ovary tissue | — | — | Normal | + | − | − |
| C5 | Endometrioid adenocarcinoma | 2 | IIIc | Malignant | + | + | + |
| C6 | Granular cell tumor | — | I | Malignant | − | − | − |
| C8 | Ovary tissue | — | — | Normal | − | − | − |
| Adrenal glad | Pheochromocytoma (tissue marker) | — | — | Malignant | − | − | − |

TABLE 3

Normal tissue reactivity of LHR, Mesothelin, and MUC-16 by Immunohistochemistry

| Position | Organ | Pathology Diagnosis | Type | LHR | MUC16 | Mesothelin |
|---|---|---|---|---|---|---|
| A1 | Cerebellum | Normal | Normal | − | − | − |
| A2 | Small intestine | Normal | Normal | − | − | − |

TABLE 3-continued

Normal tissue reactivity of LHR, Mesothelin, and MUC-16 by Immunohistochemistry

| Position | Organ | Pathology Diagnosis | Type | LHR | MUC16 | Mesothelin |
|---|---|---|---|---|---|---|
| A3 | Lung | Normal | Normal | − | − | − |
| A4 | Pituitary Gland | Normal | Normal | − | − | − |
| A5 | Spleen | Normal | Normal | − | − | − |
| A6 | Umbilical cord | Normal | Normal | − | − | − |
| B1 | Cerebral cortex | Normal | Normal | − | − | − |
| B2 | Stomach | Normal | Normal | − | − | − |
| B3 | Liver | Cirrhosis | Normal | − | − | − |
| B4 | Parathyroid | Adenoma | Normal | − | − | − |
| B5 | Spinal cord | Normal | Normal | − | − | − |
| B6 | Thyroid | Normal | Normal | − | − | − |
| B7 | Tonsil | Reactive | Inflammation | − | − | − |
| C1 | Bone marrow | Normal | Normal | − | − | − |
| C2 | Fallopian tube | Normal | Normal | − | − | − |
| C3 | Kidney | Normal | Normal | +? tubules | +? tubules? | +? tubules |
| C4 | Pancreas | Normal | Normal | − | − | − |
| C5 | Skin | Normal | Normal | − | − | − |
| C6 | Thymus | Normal | Normal | − | − | − |
| C7 | Uterus | Normal endometrium | Normal | − | + | − |
| D1 | Bladder | Normal epithelial | Normal | − | − | − |
| D2 | Breast | Normal | Normal | − | − | − |
| D3 | Heart | Normal | Normal | − | − | − |
| D4 | Ovary | Normal | Normal | − | − | − |
| D5 | Prostate | Normal | Normal | − | − | − |
| D6 | Testis | Normal | Normal | − | − | − |
| D7 | Uterus | Normal cervix | Normal | + | + | − |
| E1 | Adrenal Gland | Normal | Normal | − | − | − |
| E2 | Breast | Normal | Normal | − | − | − |
| E3 | Colon | Normal | Normal | − | − | − |
| E4 | Lymph node | Reactive | Inflammation | − | − | − |
| E5 | Placenta | Normal | Normal | + | − | − |
| E6 | Stratified muscle | Normal | Normal | − | − | − |
| E7 | Urethra | Normal | Normal | +/− | − | − |

TABLE 4

| Antibody | CDR1 | CDR2 | CDR3 |
|---|---|---|---|
| Heavy chain variable region | | | |
| 5F4 | GYSITSGYG (SEQ ID NO: 16) | IHYSGST (SEQ ID NO: 19) | ARSLRY (SEQ ID NO: 22) |
| 4A7 | GFSLTTYG (SEQ ID NO: 17) | IWGDGST (SEQ ID NO: 20) | AEGSSLFAY (SEQ ID NO: 23) |
| 8B7 | GYSFTGYY (SEQ ID NO: 18) | IYPYNGVS (SEQ ID NO: 21) | ARERGLY QLRAMDY (SEQ ID NO: 24) |
| Light chain variable region | | | |
| 5F4 | SSVNY (SEQ ID NO: 25) | DTS (SEQ ID NO: 28) | HQWSSYPYT (SEQ ID NO: 31) |
| 4A7 | QSLLNSG NQKNY (SEQ ID NO: 26) | WAS (SEQ ID NO: 29) | QNDYSYPLT (SEQ ID NO: 32) |
| 8B7 | QSISNN (SEQ ID NO: 27) | NAS (SEQ ID NO: 30) | QQSNSWPYT (SEQ ID NO: 33) |

TABLE 5

LHR Staining in Normal Tissues

| Site | total cases | staining (positive/total) |
|---|---|---|
| Testis | 3 | 3/3 |
| Ovary | 3 | 3/3 |
| Appendix | 3 | 0/3 |
| Aorta | 3 | 0/3 |
| Bladder | 3 | 0/3 |
| Brain | 1 | 0/1 |
| Esophagus | 3 | 0/3 |
| Gallbladder | 3 | 0/3 |
| Heart | 3 | 0/3 |
| Kidney | 3 | 0/3 |
| Large intestine | 3 | 0/3 |
| Liver | 3 | 0/3 |
| Lung | 3 | 0/3 |
| Rectum | 3 | 0/3 |

TABLE 5-continued

LHR Staining in Normal Tissues

| Site | total cases | staining (positive/total) |
| --- | --- | --- |
| Small intestine | 3 | 0/3 |
| Spleen | 3 | 0/3 |
| Thyroid | 3 | 3/3 |
| Urethra | 3 | 0/3 |
| Vena cava | 3 | 0/3 |

Example 3

Anti-LHR CAR T-Cells

Construction of the CAR Lentiviral Constructs

Figure 10:
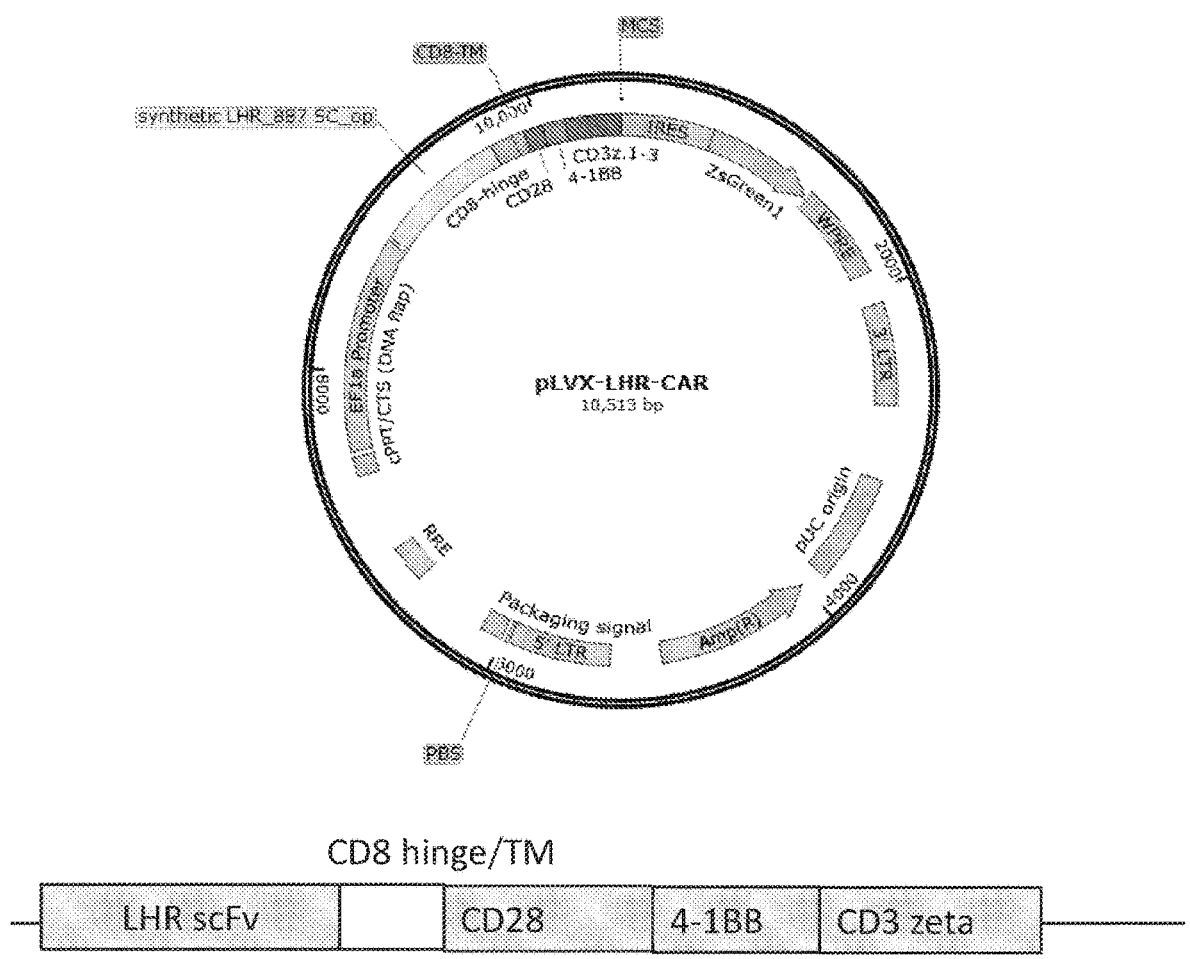
FIG. 10 shows the backbone of the gene transfer vector is an HIV-based, bicistronic lentiviral vector, pLVX-IRES-ZsGreen containing HIV-1 5' and 3' long terminal repeats (LTRs), packaging signal (Ψ), EF1α promoter, internal ribosome entry site (IRES), ZsGreen, a green fluorescent protein, woodchuck hepatitis virus post-transcriptional regulatory element (WPRE), and simian virus 40 origin (SV40). Constitutive expression of the transgene comprising of a scFv specific to LHR, a CD8 hinge and transmembrane region and CD28, 4-1BB and CD3ζ signaling domain, is insured by the presence of the EF1α promoter. Expression of the detection protein, ZsGreen is carried out by the IRES region. Integration of the vector was assayed by the presence of ZsGreen in the cells, via fluorescent microscopy.

The CAR consists of an extracellular antigen binding moiety or scFV which binds LHR. The scFV is connected via a CD8 hinge region to the cytoplasmic signaling domain, comprised of the CD8 transmembrane region, and the signaling domains from CD28, 4-1BB and CD3z. The entire CAR sequence including the signaling domains, were synthetically synthesized by Genewiz Gene Synthesis Services (Piscataway, N.J.) (FIG. 10). The plasmids are purified and digested with the appropriate restriction enzymes to be inserted into an HIV-1-based, bicistronic lentiviral vector (pLVX-IRES-ZsGreen, Clontech, Signal Hill, Calif.) containing HIV-1 5' and 3' long terminal repeats (LTRs), packaging signal (Ψ), EF1α promoter, internal ribosome entry site (IRES), woodchuck hepatitis virus post-transcriptional regulatory element (WPRE), and simian virus 40 origin (SV40) via overnight $T_4$ DNA ligase reaction (New England Biosciences; Ipswich, Mass.). NovaBlue Singles™ chemically-competent $E.$ $coli$ cells are then transformed with the resulting LHR-CAR-containing lentiviral plasmid.

Production of Lentiviral Particles

Prior to transfection, HEK 293T cells are seeded at $4.0 \times 10^6$ cells/150 cm² tissue-culture-treated flask in 20 mL DMEM supplemented with 10% dialyzed FCS and incubated overnight at 37° C. in a humidified 5% $CO_2$ incubator. Once 80-90% confluent, HEK 293T cells are incubated in 20 ml DMEM supplemented with 1-% dialyzed FCS without penicillin/streptamycin for two hours in a 37° C. humidified 5% $CO_2$ incubator. HEK293T cells are co-transfected with the specific pLVX-CAR plasmid and lentiviral packaging plasmids containing genes necessary to form the lentiviral envelope & capsid components. A proprietary reaction buffer and polymer to facilitate the formation of plasmid-containing nanoparticles that bind HEK 293T cells are also added. After incubating the transfected-HEK 293T cell cultures for 24 hours at 37° C., the transfection medium is replaced with 20 mL fresh complete DMEM. Lentivirus supernatants are collected every 24 hours for three days and the supernatants will be spun down at 1,250 rpm for 5 minutes at 4° C., followed by filter sterilization and centrifugation in an ultracentrifuge at 20,000 g for 2 hrs at 4° C. The concentrated lentivirus is re-suspended in PBS containing 7% trehalose and 1% BSA for long term storage. The lentivirus is aliquoted and stored at −80° C. until use for transduction of target CD4⁺ and CD8⁺ T cells. The cell supernatants harvested after 24 hours are tested for lentiviral particles via sandwich ELISA against p24, the main lentiviral capsid protein. Transfection efficiency as determined by the expression of the protein marker ZsGreen, was estimated between 20%-50%, by visualization under a fluorescent microscope.

Purification, Activation, and Enrichment of Human CD4⁺ and CD8⁺ Peripheral Blood T-Cells Peripheral blood mononuclear cells (PBMCs) enriched by density gradient centrifugation with Ficoll-Paque Plus (GE Healthcare; Little Chalfont, Buckinghamshire, UK) are recovered and washed by centrifugation with PBS containing 0.5% bovine serum albumin (BSA) and 2 mM EDTA. T-cell enrichment kits (Stem Cell Technologies) are used to magnetically isolate these human T-cell subsets using negative selection for CD4⁺ and CD8⁺ T-cells. The purity of CD4⁺ and CD8⁺ T-cell populations are assessed by flow cytometry using Life Technologies Acoustic Attune® Cytometer, and are enriched by Fluorescence-Activated Cell Sorting. CD4⁺ and CD8⁺ T-cells mixed 1:1 are maintained at a density of $1.0 \times 10^6$ cells/mL in complete 50% Click's medium/50% RPMI-1640 medium supplemented with 100 IU/mL IL-2 in a suitable cell culture vessel, to which α-CD3/α-CD28 Human T-cell activator beads (Stem Cell Technologies) are added to activate cultured T cells. T-cells are incubated at 37° C. in a 5% $CO_2$ incubator for 2 days prior to transduction with CAR lentiviral particles.

Lentiviral Transduction of CD4⁺ CD8⁺ T-Cells

Activated T-cells are collected and dead cells are removed by Ficoll-Hypaque density gradient centrifugation or the use of MACS Dead Cell Removal Kit (Miltenyi Biotec; San Diego, Calif.). In a 6-well plate, activated. T-cells are plated at a concentration of $1.0 \times 10^6$ cells/mL in complete medium. Cells are transduced with the lentiviral particles supplemented with Lentiblast, a transfection aid (Oz Biosciences, San Diego, Calif.) to the cells. Transduced cells are incubated for 24 hours at 37° C. in a humidified 5% $CO_2$ incubator. The cells are then pelleted by centrifugation and the media changed, followed by addition of the T-cell activator beads (Stem Cell Technologies, San Diego, Calif.).

RT-PCR for mRNA Expression mRNA from transduced T-cells are isolated using the Nucleospin RNA kit (Clontech, Signal Hill, Calif.). RT-PCR is run using the OneTaq One Step RNA kit (New England Biolabs, Boston, Mass.), using the following primers, 5' CGCCTGATATCTACATCTGGGC 3' (SEQ ID NO: 73) and 5' ATCGGCAGCTACAGCCATCT 3' (SEQ ID NO: 74). Samples are run on a 1% agarose gel.

Cell Cytotoxicity Assays

Cytotoxicity of the CAR T-cells are determined using the lactate dehydrogenase (LDH) cytotoxicity kit (Thermo Scientific, Carlsbad, Calif.). Activated. T-cells are collected and $1 \times 10^6$ cells are transduced with the appropriate CAR lentiviral construct as described above. Cells are activated used the T-cell activator beads (Stem Cell Technologies, San Diego, Calif.) for two days prior to cytotoxicity assays. The optimal number of target cells is determined as per the manufacturer's protocol. For the assays, the appropriate target cells are plated in triplicate in a 96 well plate for 24 hours at 37° C. in a 5% $CO_2$ incubator, followed by the addition of activated CAR T-cells in ratios of 20:1, 10:1, 5:1 and 1:1, and incubated for 24 hours at 37° C. in a 5% $CO_2$ incubator. Cells are then lysed at 37° C. for 45 mins and centrifuged at 1,250 rpm for 5 mins. The supernatant is transferred to a fresh 96 well plate, followed by the addition of the reaction mixture for 30 minutes. The reaction is the stopped using the stop solution and the plate read at 450 nm with an absorbance correction at 650 nm.

In Vivo Tumor Regression Assay

Foxn1 null mice are injected with SKOV3, an ovarian tumor cell line which expresses LHR. Two×106 cells in 200 ul of phosphate buffered saline are injected into the left flank of the mice using a 0.2 mL inoculum. Naive T-cells are activated for 2 days using the αCD3/CD28 activator complex (Stem Cell Technologies, San Diego, Calif.). The activated T-cells are then transduced with the pLVX-LHR-CAR lentiviral particles as described above, and activated for 2 days. 2.5×106 of the activated T-cells expressing the LHR CAR are injected intravenously into the mice on day 7 after tumor inoculation. Tumor sizes are assessed twice a week using Vernier calipers and the volume calculated.

Cytotoxicity for LHR CAR T-Cells

Figure 11:
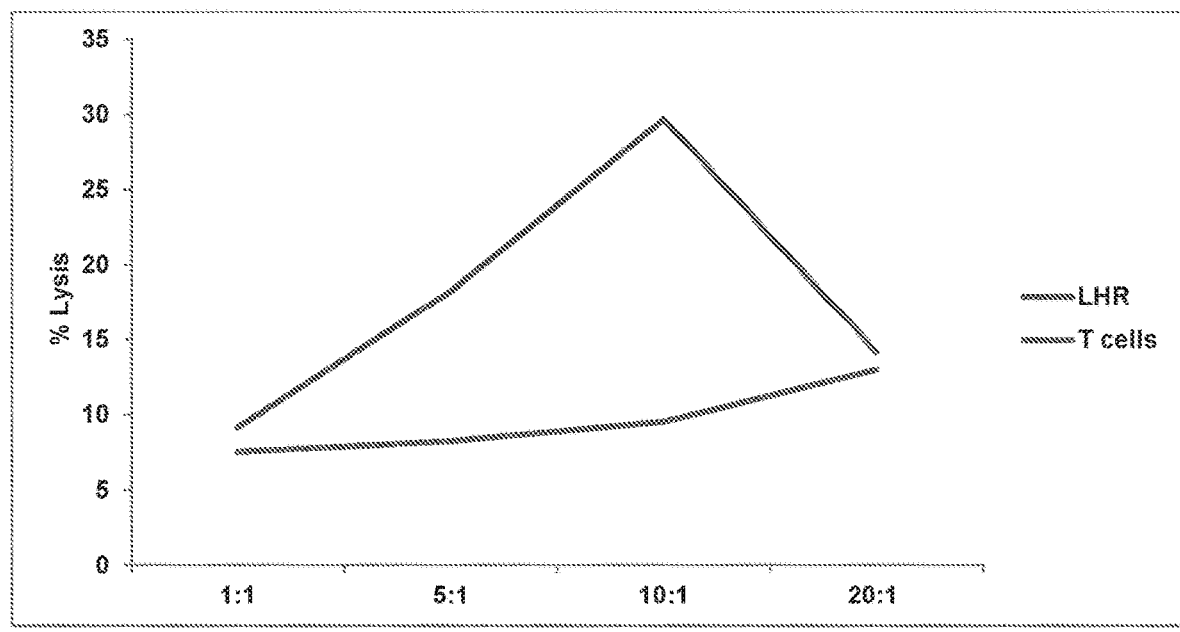
FIG. 11 depicts the results of the cytotoxicity assay of LHR CAR T-cells. Cytotoxicity of the LHR CAR expressing T-cells was determined using an LDH cytotoxicity kit as described in the Methods. Prior to the assay, T-cells were activated using αCD3/CD8 beads (Stem Cell Technologies, 30 ul to 2 ml of media). The activated T-cells were transduced with LHR lentiviral particles, following which the T cells were activated for using the αCD3/CD8 beds. Untransduced, activated T-cells were used as a control. 3,000 SKOV3 cells were plated per well. LHR transduced T cells were added in ratios of 20:1, 10:1, 5:1 and 1:1 (60,000-3000) to the wells. Each data point represents the average of triplicate measurements.

The cytolytic activity of the LHR CAR-T-cells was examined using the SKOV3 ovarian cancer cell line as target cells. SKOV3 was shown to express LHR by FACS analysis. CAR T-cells were added in ratios of 20:1, 10:1, 5:1 and 1:1 of effector cells to target cells. After 24 hours of incubation, the LHR CAR T-cells effectively lysed. SKOV3 at a ratio of 10:1, showing a 30% lysis rate (FIG. 11). In comparison, uninduced T-cells did not show any cytotoxic activity at any of the ratios of effector cells to target cells used.

RNA Expression for LHR CAR

Figure 12:
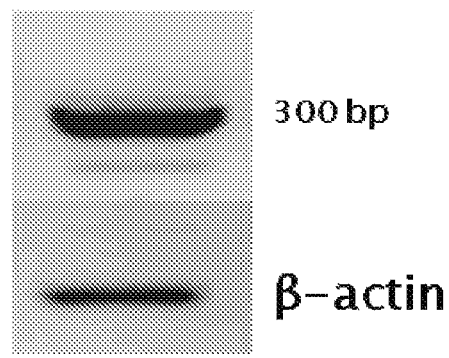
FIG. 12 depicts mRNA expression of the LHR CAR in primary T-cells. Primary T-cells transduced with the LHR CAR show expression of the LHR mRNA. Primers used spanned the area between the CD8 hinge and the 4-1BB signaling domain (300 bp).

RT-PCR using mRNA isolated from T-cells transduced with the LHR CAR show mRNA expression of the chimeric CAR (FIG. 12). The RT-PCR was performed with primers that span the chimeric CAR between the CD8 hinge and the 4-1BB signaling domain, and is therefore highly specific to the expression of the CAR.

Equivalents

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

What is claimed is:

1. A chimeric antigen receptor (CAR) comprising:
   (a) an antigen binding domain of an anti-luteinizing hormone receptor ("LHR") antibody comprising an anti-LHR heavy chain (HC) variable region and an anti-LHR light chain (LC) variable region, wherein the HC comprises:
      (i) a CDR1 comprising the amino acid sequence of GYSFTGYY (SEQ ID NO.: 18);
      (ii) a CDR2 comprising the amino acid sequence of IYPYNGVS (SEQ ID NO.: 21); and
      (iii) a CDR3 comprising the amino acid sequence of ARERGLYQLRAMDY (SEQ ID NO.: 24); and
   the LC comprises
      (i) a CDR1 comprising the amino acid sequence of QSISNN (SEQ ID NO.:27);
      (ii) a CDR2 comprising the amino acid sequence of NAS (SEQ ID NO:30); and
      (iii) a CDR3 comprising the amino acid sequence of QQSNSWPYT (SEQ ID NO:33);
   (b) a CD8 α hinge domain;
   (c) a CD8 α transmembrane domain;
   (d) a 4-1BB costimulatory signaling region; and
   (e) a CD3 zeta signaling domain.

2. The CAR of claim 1, further comprising a linker polypeptide located between the anti-LHR HC variable region and the anti-LHR LC variable region.

3. The CAR of claim 1, wherein the anti-LHR heavy chain variable region comprises a polypeptide having SEQ ID NO.:4 or a polypeptide having at least 90% sequence identity to SEQ ID NO: 4.

4. The CAR of claim 1, wherein the anti-LHR light chain variable region comprises a polypeptide having SEQ ID NO.:8 or a polypeptide having at least 90% sequence identity to SEQ ID NO: 8.

5. The CAR of claim 1, further comprising a detectable marker or a purification marker.

6. An isolated cell comprising the CAR of claim 1.

7. The isolated cell of claim 6, wherein the cell is a T-cell.

8. The isolated cell of claim 6, which is a natural killer (NK) cell.

9. A composition comprising the cell of claim 6 and a carrier.

10. A method of inhibiting the growth of an ovarian tumor or prostate cancer tumor in a subject in need thereof, comprising administering to the subject an effective amount of the isolated T-cell of claim 7.

11. The method of claim 10, wherein the isolated T-cells are autologous to the subject being treated.

12. The method of claim 10, wherein the tumor expresses or overexpresses LHR.

13. The method of claim 10, wherein the subject is selected from a human, an animal, a non-human primate, a dog, cat, a sheep, a mouse, a horse, or a cow.

14. A method of treating ovarian cancer or prostate cancer in a subject in need thereof, comprising administering to the subject an effective amount of the isolated T-cell of claim 7.

15. The method of claim 14, wherein the isolated T-cells are autologous to the subject being treated.

16. The method of claim 14, wherein the subject is selected from a human, an animal, a non-human primate, a dog, cat, a sheep, a mouse, a horse, or a cow.

\* \* \* \* \*